(12) United States Patent
Spiegelman et al.

(10) Patent No.: US 8,969,519 B2
(45) Date of Patent: Mar. 3, 2015

(54) COMPOSITIONS AND METHODS FOR BROWN FAT INDUCTION AND ACTIVITY USING FNDC5

(75) Inventors: Bruce M. Spiegelman, Waban, MA (US); Pontus Bostrom, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/611,641

(22) Filed: Sep. 12, 2012

(65) Prior Publication Data

US 2013/0074199 A1 Mar. 21, 2013

Related U.S. Application Data

(60) Provisional application No. 61/534,016, filed on Sep. 13, 2011, provisional application No. 61/612,535, filed on Mar. 19, 2012.

(51) Int. Cl.
| | | |
|---|---|---|
| *A61K 38/00* | (2006.01) | |
| *C07K 14/435* | (2006.01) | |
| *C07K 14/78* | (2006.01) | |
| *C07K 19/00* | (2006.01) | |
| *C07K 16/18* | (2006.01) | |
| *C07K 14/575* | (2006.01) | |
| *C07K 14/47* | (2006.01) | |

(52) U.S. Cl.
CPC ............... *C07K 14/435* (2013.01); *C07K 14/78* (2013.01); *C07K 19/00* (2013.01); *C07K 16/18* (2013.01); *C07K 14/575* (2013.01); *C07K 14/47* (2013.01)
USPC ............................. 530/350; 435/377; 514/1.1

(58) Field of Classification Search
None
See application file for complete search history.

(56) References Cited

U.S. PATENT DOCUMENTS

| | | | |
|---|---|---|---|
| 6,943,241 B2 * | 9/2005 | Isogai et al. | 536/23.1 |
| 7,745,391 B2 | 6/2010 | Mintz et al. | |
| 2003/0236392 A1 | 12/2003 | Isogai et al. | |
| 2007/0099251 A1 * | 5/2007 | Zhang et al. | 435/7.23 |

OTHER PUBLICATIONS

International Search Report dated Feb. 25, 2013, from PCT/US2012/054797.
Boström et al., "A PGC1-α-dependent myokine that drives brown-fat-like development of white fat and thermogenesis," Nature, 481:463-468 (2012).
Ferrer-Martínez et al., "Mouse Pep: A Novel Peroxisomal Protein Linked to Myoblast Differentiation and Development," Developmental Dynamics, 224:154-167 (2002).
Smorlesi et al., "The adipose organ: white-brown adipocyte plasticity and metabolic inflammation," Obesity Reviews, 13:83-96 (2012).
Teufel et al., "*Frcp1* and *Frcp2*, two novel fibronetcin type III repeat containing genes," Gene, 297:79-83 (2002).
Tiraby et al., "Acquirement of Brown Fat Cell Features by Human White Adipocytes," The Journal of Biological Chemistry, 278(35):33370-33376 (2003).

* cited by examiner

*Primary Examiner* — Daniel C Gamett
(74) *Attorney, Agent, or Firm* — Foley Hoag LLP

(57) ABSTRACT

The invention provides compositions and methods for brown fat induction and activity through modulation of Fndc5 activity and/or expression. Also provided are methods for preventing or treating metabolic disorders in a subject through modulation of Fndc5 activity and/or expression. Further provided are methods for identifying compounds that are capable of modulating Fndc5 activity and/or expression.

20 Claims, 14 Drawing Sheets

Figure 5

| gene | FC | p= |
|---|---|---|
| Ucp1: uncoupling protein 1 (mitochondrial. proton carrier) | 80,41 | 8,62E-05 |
| Otop1: otopetrin 1 | 25,98 | 6,87E-05 |
| Aadac: arylacetamide deacetylase (esterase) | 10,52 | 0,000211 |
| Cox7a1: cytochrome c oxidase. subunit VIIa 1 | 7,73 | 1,01E-08 |
| Acaa1b: acetyl-Coenzyme A acyltransferase 1B | 7,50 | 5,36E-05 |
| Ubd: ubiquitin D | 7,03 | 3,45E-05 |
| Ncan: neurocan | 7,02 | 0,000319 |
| Elovl3: elongation of very long chain fatty acids-like 3 | 6,91 | 0,000219 |
| Plin5: perilipin 5 | 6,57 | 1,23E-05 |
| Cox8b: cytochrome c oxidase. subunit VIIIb | 6,48 | 5,62E-07 |
| Scd3: stearoyl-coenzyme A desaturase 3 | 6,17 | 0,011329 |
| carnitine palmitoyltransferase 1b. Muscle | 6,14 | 0,000143 |
| Itih4: inter alpha-trypsin inhibitor. heavy chain 4 | 5,65 | 0,000318 |
| Car4: carbonic anhydrase 4 | 5,59 | 0,000885 |
| Cyp2e1: cytochrome P450. family 2. subfamily e. polypeptide 1 | 5,34 | 0,000716 |
| Slc25a34: solute carrier family 25. member 34 | 5,21 | 3,17E-05 |
| Arg1: arginase. liver | 5,02 | 0,013321 |
| Car4: carbonic anhydrase 4 | 4,80 | 0,000302 |
| Sptlc3: serine palmitoyltransferase. long chain base subunit 3 | 4,63 | 0,00014 |
| Acaa2: acetyl-Coenzyme A acyltransferase 2 | 4,48 | 0,00187 |
| Mpzl2: myelin protein zero-like 2 | 4,36 | 0,000588 |
| Reep1: receptor accessory protein 1 | 4,31 | 0,000319 |
| Acer2: alkaline ceramidase 2 | 4,30 | 0,000991 |
| Gys2: glycogen synthase 2 | 4,14 | 3,59E-07 |
| Gpr120: G protein-coupled receptor 120 | 4,01 | 0,000986 |
| Gpld1: glycosylphosphatidylinositol specific phospholipase D1 | 0,39 | 0,031602 |
| Asb4: ankyrin repeat and SOCS box-containing 4 | 0,39 | 0,019371 |
| Mm.207312.1 | 0,38 | 0,001832 |
| Cyp2f2: cytochrome P450. family 2. subfamily f. polypeptide 2 | 0,37 | 0,000688 |
| Odz3: odd Oz/ten-m homolog 3 (Drosophila) | 0,37 | 0,000236 |
| Zfp207: zinc finger protein 207 | 0,36 | 0,039105 |
| Ntn4: netrin 4 | 0,36 | 0,001783 |
| Higd1b: HIG1 domain family. member 1B | 0,35 | 0,000626 |
| Myh11: myosin. heavy polypeptide 11. smooth muscle | 0,34 | 0,000105 |
| Serpina1b: serine (or cysteine) preptidase inhibitor. clade A. member 1B | 0,32 | 7,31E-06 |
| Aplnr: apelin receptor | 0,31 | 5,19E-06 |
| Mtx3: metaxin 3 | 0,28 | 0,001888 |
| Serpina1a | 0,27 | 1,95E-05 |
| Oxtr: oxytocin receptor | 0,24 | 6,85E-05 |
| 4921521F21Rik: RIKEN cDNA 4921521F21 gene | 0,24 | 0,000241 |
| Rgs5: regulator of G-protein signaling 5 | 0,19 | 0,00216 |
| Lep: leptin | 0,15 | 0,000173 |
| Mup5: major urinary protein 5 | 0,12 | 0,00016 |
| Mup3: major urinary protein 1 | 0,07 | 1,64E-06 |

Figure 9

```
1_human  .....MRRWLGCVCFALVQADSPSAPVNTVRHLKANSAVVSNDVLEDEVVI
2_mouse  MPPGPCAWPPAALRLWLGCVCFALVQADSPSAPVNTVRHLKANSAVVSNDVLEDEVVI 1_human  GPAISQQKKDVRMLRPIQEVNTTRSCALWDLEEDTEYIVHVQAISIQGQSPASEPVLFK
2_mouse  GPAISQQYKDVRMLRPIQEVNTTRSCALWDLEEDTEYIVHVQAISIQGQSPASEPVLFK 1_human  TPREAEKMASKNKDEVTMKEMGRNQQLRTGEVLIVVLFMWAGVIALFCRQYDIKDNE
2_mouse  TPREAEKMASKNKDEVTMKEMGRNQQLRTGEVLIVVLFMWAGVIALFCRQYDIKDNE 1_human  PNNNKEKTKSASETSTPEHQGGGLLRSKI
2_mouse  PNNNKEKTKSASETSTPEHQGGGLLRSKI
```

COMPOSITIONS AND METHODS FOR BROWN FAT INDUCTION AND ACTIVITY USING FNDC5

RELATED APPLICATIONS

This application claims the benefit of U.S. Provisional Application No. 61/612,535, filed on Mar. 19, 2012 and 61/534,016, filed on Sep. 13, 2011; the entire content of each of said applications is incorporated herein in its entirety by this reference.

STATEMENT OF RIGHTS

This invention was made with government support under Grants NIH RO1 DK54477, DK31405, and DK61562 awarded by the National Institutes of Health. The U.S. government has certain rights in the invention. This statement is included solely to comply with 37 C.F.R. §401.14(a)(f)(4) and should not be taken as an assertion or admission that the application discloses and/or claims only one invention.

BACKGROUND OF THE INVENTION

Metabolic disorders comprise a collection of health disorders or risks that increase the risk of morbidity and loss of qualify of life. For example, diabetes, obesity, including central obesity (disproportionate fat tissue in and around the abdomen), atherogenic dyslipidemia (including a family of blood fat disorders, e.g., high triglycerides, low HDL cholesterol, and high LDL cholesterol that can foster plaque build-ups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are all metabolic disorders collectively afflicting greater than 50 million people in the United States.

PGC1α (PPARγ coactivator-1α) is a transcriptional coactivator that mediates many biological programs related to energy metabolism. Originally described as a coactivator of PPARγ that modulated expression of uncoupling protein 1 (UCP1) and thermogenesis in brown fat, it has also been shown to control mitochondrial biogenesis and oxidative metabolism in many cell types. PGC1α is induced in muscle by exercise and stimulates many of the known beneficial effects of exercise in muscle: mitochondrial biogenesis, angiogenesis and fiber-type switching (Handschin and Spiegelman (2008) *Nature* 454, 463-469). It also provides resistance to muscular dystrophy and denervation-linked muscular atrophy (Sandri et al. (2006) *Proc. Natl. Acad. Sci. USA* 103, 16260-16265). The healthful benefits of elevated muscle expression of PGC1α may go beyond the muscle tissue itself. Transgenic mice with mildly elevated muscle PGC1α are dramatically resistant to age-related obesity and diabetes and have a prolonged life-span (Wenz et al. (2009) *Proc. Natl. Acad. Sci. USA* 106, 20405-20410), which suggests that PGC1α might stimulate the secretion of factors from skeletal muscle that affects the health and function of other tissues.

Despite decades of scientific research, such factors have not been identified and few effective therapies have emerged to treat metabolic disorders and related cardiovascular disease (cardiovascular disease remains the main cause of mortality in the Western world). Accordingly, there is a great need to identify molecular regulators of metabolic disorders, including the generation of diagnostic, prognostic, and therapeutic agents to effectively control metabolic disorders in subjects.

SUMMARY OF THE INVENTION

The present invention is based in part on the discovery that Fndc5 and biologically active fragments thereof are secreted polypeptides that have the ability, even at nanomolar concentrations, to induce significant induction of brown fat cells.

In one aspect, an isolated polypeptide is provided which a) comprises amino acid residues 73-140 of SEQ ID NO:2 but which lacks an Fndc5 signal peptide; b) comprises amino acid residues 30-140 of SEQ ID NO:2 but which does not encode the full-length amino acid sequence of an Fndc5 protein; or c) comprises amino acid residues 29-140 of SEQ ID NO:2 but which does not encode the full-length amino acid sequence of an Fndc5 protein. In one embodiment, the isolated polypeptide comprises amino acid residues 73-140 of SEQ ID NO:2, but which lacks an Fndc5 signal peptide (e.g., lacks the C-terminal residue of SEQ ID NO:2 or comprises amino acid residues 29-140 of SEQ ID NO:2 or comprises amino acid residues 30-140 of SEQ ID NO:2). In another embodiment, the isolated polypeptide comprises amino acid residues 30-140 of SEQ ID NO:2 and does not encode the full-length amino acid sequence of an Fndc5 protein. In still another embodiment, the isolated polypeptide comprises amino acid residues 29-140 of SEQ ID NO:2 but which does not encode the full-length amino acid sequence of an Fndc5 protein. In yet another embodiment, the isolated polypeptide has a molecular weight of about 20 kilodaltons (e.g., as determined by gel electrophoresis under deglycosylated, reduced, and denatured conditions).

In some embodiments, the polypeptide lacks an Fndc5 hydrophobic domain, lacks an Fndc5 C-terminal domain, and/or lacks the C-terminal sequence of SEQ ID NO:2. In another embodiment, the polypeptide comprises at least one fibronectin domain. In still another embodiment, the polypeptide comprises at least one fibronectin domain but lacks one or more functional domain(s) selected from the group consisting of signal peptide, hydrophobic, and C-terminal domains. In yet another embodiment, the polypeptide consists essentially of amino acid residues 73-140 of SEQ ID NO:2. In another embodiment, the polypeptide consists essentially of amino acid residues 29-140 of SEQ ID NO:2. In still another embodiment, the polypeptide consists essentially of amino acid residues 30-140 of SEQ ID NO:2. In yet another embodiment, the polypeptide has the sequence of human Irisin.

In other embodiments, the polypeptide has the ability to promote one or more biological activities selected from the group consisting of: a) expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio2; b) thermogenesis in adipose cells; c) differentiation of adipose cells; d) insulin sensitivity of adipose cells; e) basal respiration or uncoupled respiration; f) hepatosteatosis reduction; g) appetite reduction; h) insulin secretion of pancreatic beta cells; i) cardiac function reduction; j) cardiac hypertrophy; and k) muscle hypoplasia reduction. In another embodiment, the polypeptide has the ability to promote the expression of fgf21, to promote the expression of ucp1, and/or to promote the expression of both fgf21 and ucp1. In still another embodiment, the polypeptide has the ability to induce brown fat differentiation. In yet another embodiment, the polypeptide is less than 195 amino acids in length. In another embodiment, the polypeptide is between 70 and 125 amino acids in length. In still another embodiment, the polypeptide is more than 65 amino acids in length and less than 135 amino acids in length. In yet another embodiment, at least one amino acid residue of the polypeptide is glycosylated and/or pegylated. In another embodiment, the polypeptide is secreted by a mammalian cell. In still another embodiment, the polypeptide further comprises a heterologous polypeptide (e.g., a dimerization domain, an oligomerization domain, an agent that promotes plasma solubility, a signal peptide, a peptide tag, an antibody, and/or an antibody fragment, such as an Fc domain, and the like). In yet another embodiment, the polypeptide is at least 75% pure.

In another aspect, pharmaceutical composition is provided comprising a polypeptide comprising amino acid residues 73-140 of SEQ ID NO:2, and a pharmaceutically acceptable agent selected from the group consisting of excipients, diluents, and carriers. In one embodiment, the polypeptide is a polypeptide of the present invention described herein. In another embodiment, the pharmaceutical composition comprises the polypeptide at a purity of at least 75%.

In still another aspect, an isolated nucleic acid molecule is provided selected from the group consisting of: a) an isolated nucleic acid molecule which encodes at least one fibronectin domain of an Fndc5 protein and which does not encode full-length Fndc5; b) an isolated nucleic acid molecule which encodes at least one fibronectin domain of an Fndc5 protein and which does not encode one or more functional domain(s) of an Fndc5 protein selected from the group consisting of signal peptide, hydrophobic, and C-terminal domains; c) an isolated nucleic acid molecule which encodes a polypeptide comprising an amino acid sequence of residues 73-140 of SEQ ID NO:2, and which does not encode one or more functional domain(s) of an Fndc5 protein selected from the group consisting of signal peptide, hydrophobic, and C-terminal domains; d) an isolated nucleic acid molecule which encodes a polypeptide comprising an amino acid sequence of residues 30-140 of SEQ ID NO:2 and which does not encode one or more functional domain(s) of an Fndc5 protein selected from the group consisting of signal peptide, hydrophobic, and C-terminal domains; e) an isolated nucleic acid molecule which encodes a polypeptide comprising an amino acid sequence of residues 29-140 of SEQ ID NO:2 and which does not encode one or more functional domain(s) of an Fndc5 protein selected from the group consisting of signal peptide, hydrophobic, and C-terminal domains; f) an isolated nucleic acid molecule which encodes a polypeptide comprising amino acid residues 73-140 of SEQ ID NO:2, 30-140 of SEQ ID NO:2 or 29-140 of SEQ ID NO:2 and which is less than 630 nucleotides in length; g) an isolated nucleic acid molecule which encodes a polypeptide consisting essentially of the amino acid sequence of residues 73-140 of SEQ ID NO:2; h) an isolated nucleic acid molecule which encodes a polypeptide consisting essentially of the amino acid sequence of residues 30-140 of SEQ ID NO:2; i) an isolated nucleic acid molecule which encodes a polypeptide consisting essentially of the amino acid sequence of residues 29-140 of SEQ ID NO:2; j) an isolated nucleic acid molecule which encodes a polypeptide comprising amino acid residues 73-140 of SEQ ID NO:2 but which does not encode a full-length Fndc5 amino acid sequence; k) an isolated nucleic acid molecule which encodes a polypeptide comprising amino acid residues 30-140 of SEQ ID NO:2 but which does not encode a full-length Fndc5 amino acid sequence; l) an isolated nucleic acid molecule which encodes a polypeptide comprising amino acid residues 29-140 of SEQ ID NO:2 but which does not encode a full-length Fndc5 amino acid sequence; m) an isolated nucleic acid molecule which encodes a polypeptide comprising the amino acid sequence of residues 30-140 of SEQ ID NO:2 but which does not encode the full-length amino acid sequence of SEQ ID NO:2; and n) an isolated nucleic acid molecule which encodes a polypeptide comprising the amino acid sequence of residues 29-140 of SEQ ID NO:2 but which does not encode the full-length amino acid sequence of SEQ ID NO:2.

In some embodiments, the nucleic acid molecule further comprises a nucleic acid sequence encoding a heterologous polypeptide. In another embodiment, the heterologous polypeptide is selected from the group consisting of a signal peptide, a peptide tag, a dimerization domain, an oligomerization domain, an antibody, or an antibody fragment.

In yet another aspect, a pharmaceutical composition is provided comprising a nucleic acid molecule of the present invention described herein, or full length human Fndc5, and a pharmaceutically acceptable agent selected from the group consisting of excipients, diluents, and carriers.

In another aspect, a vector is provided comprising a nucleic acid molecule described herein. In some embodiments, the vector is an expression vector.

In still another aspect, a host cell is provided transfected with an expression vector described herein.

In yet another aspect, a method of producing a polypeptide is provided comprising culturing host cells described herein in an appropriate culture medium to, thereby, produce the polypeptide. In some embodiments, the host cell is a bacterial cell or a eukaryotic cell. In other embodiments, the host cell is genetically engineered to express a selectable marker. In still other embodiments, the method further comprises the step of isolating the polypeptide from the medium or host cell.

In another aspect, a method for modulating a metabolic response is provided comprising, contacting a cell with an agent, wherein the agent comprises Fndc5 selected from the group consisting of SEQ ID NO:2, 4, 6, 8, 10, 12, or 14 or an active fragment thereof, or a nucleic acid that encodes Fndc5 of SEQ ID NO:2, 4, 6, 8, 10, 12, or 14 or an active fragment thereof, to thereby modulate the metabolic response. In one embodiment, the agent comprises Fndc5 of SEQ ID NO:2, 4, 6, 8, or 14, and/or an active fragment thereof. In another embodiment, the agent comprises a polypeptide of the present invention described herein. In still another embodiment, the agent comprises a nucleic acid that encodes Fndc5 of SEQ ID NO:2, 4, 6, 8, or 14 or an active fragment thereof. In yet another embodiment, the agent comprises a nucleic acid of the present invention described herein. In another embodiment, the method further comprises contacting the cell with an additional agent that increases the metabolic response. In still another embodiment, the step of contacting occurs in vivo. In yet another embodiment, the step of contacting occurs in vitro. In another embodiment, the cell is selected from the group consisting of fibroblasts, myoblasts, myocytes, adipoblasts, adipocytes, hepatocytes, and neural cells. In still another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio2; b) modified thermogenesis in adipose cells; c) modified differentiation of adipose cells; d) modified insulin sensitivity of adipose cells; e) modified basal respiration or uncoupled respiration; f) modified hepatosteatosis; g) modified obesity or appetite; h) modified insulin secretion of pancreatic beta cells; i) modified cardiac function; j) modified cardiac hypertrophy; and k) modified muscle hypoplasia. In yet another embodiment, the agent has the ability to promote the expression of fgf21, to promote the expression of ucp1, and/or to promote the expression of both fgf21 and ucp1. In another embodiment, the method further comprises evaluating a metabolic response selected from a)-k). In still another embodiment, the agent has the ability to induce brown fat differentiation.

In still another aspect, a method for modulating a metabolic response is provided comprising, contacting a cell with an agent that down regulates the activity of Fndc5 to thereby modulate the metabolic response. In one embodiment, the agent is selected from the group consisting of an anti-FNDC5 antisense nucleic acid molecule, an anti-FNDC5 RNA interference molecule, a blocking anti-FNDC5 antibody, a non-activating form of FNDC5 polypeptide or fragment thereof, and a small molecule that binds to FNDC5. In another embodiment, the method further comprises contacting the cell with an additional agent that decreases the metabolic response. In still another embodiment, the step of contacting occurs in vivo. In yet another embodiment, the step of contacting occurs in vitro. In another embodiment, the cell is selected from the group consisting of fibroblasts, myoblasts, myocytes, adipoblasts, adipocytes, hepatocytes, and neural cells. In still another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio2; b) modified thermogenesis in adipose cells; c) modified differentiation of adipose cells; d) modified insulin sensitivity of adipose cells; e) modified basal respiration or uncoupled respiration; f) modified hepatosteatosis; g) modified obesity or appetite; h) modified insulin secretion of pancreatic beta cells; i) modified cardiac function; j) modified cardiac hypertrophy; and k) modified muscle hypoplasia. In yet another embodiment, the method further comprises evaluating a metabolic response selected from a)-k).

In yet another aspect, a method for preventing or treating a metabolic disorder in a subject is provided comprising, administering to the subject, an agent, wherein the agent comprises Fndc5 of SEQ ID NO:2, 4, 6, 8, 10, 12, or 14, or an active fragment thereof, or a nucleic acid that encodes Fndc5 of SEQ ID NO:2, 4, 6, 8, 10, 12, or 14, or an active fragment thereof, thereby preventing or treating the metabolic disorder in the subject. In one embodiment, the agent comprises Fndc5 of SEQ ID NO:2, 4, 6, 8, or 14, or an active fragment thereof. In another embodiment, the agent comprises a polypeptide of the present invention described herein. In still another embodiment, the agent comprises a nucleic acid that encodes Fndc5 of SEQ ID NO:2, 4, 6, 8, or 14, or an active fragment thereof. In yet another embodiment, the agent comprises a nucleic acid of the present invention described herein. In another embodiment, the agent is administered by intravenous or subcutaneous injection. In still another embodiment, the agent is administered in a pharmaceutically acceptable formulation. In yet another embodiment, the metabolic disorder is selected from the group consisting of insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, muscle hypoplasia, neurodegenerative diseases, and Alzheimer's disease. In another embodiment, the subject is a human. In still another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio2; b) modified thermogenesis in adipose cells; c) modified differentiation of adipose cells; d) modified insulin sensitivity of adipose cells; e) modified basal respiration or uncoupled respiration; f) modified hepatosteatosis; g) modified obesity or appetite; h) modified insulin secretion of pancreatic beta cells; i) modified cardiac function; j) modified cardiac hypertrophy; and k) modified muscle hypoplasia. In yet another embodiment, the agent has the ability to promote the expression of fgf21, to promote the expression of ucp1, and/or to promote the expression of both fgf21 and ucp1. In another embodiment, the agent has the ability to induce brown fat differentiation.

In another aspect, a method for preventing or treating a metabolic disorder in a subject is provided comprising administering to the subject an agent that inhibits Fndc5 expression and/or activity in the subject, thereby preventing or treating the metabolic disorder in the subject. In one embodiment, the agent is selected from the group consisting of an anti-FNDC5 antisense nucleic acid molecule, an anti-FNDC5 RNA interference molecule, a blocking anti-FNDC5 antibody, and a non-activating form of FNDC5 polypeptide or fragment thereof. In another embodiment, the agent is administered by intravenous or subcutaneous injection. In still another embodiment, the agent is administered in a pharmaceutically acceptable formulation. In yet another embodiment, the metabolic disorder is selected from the group consisting of obesity-associated cancer, anorexia, and cachexia. In another embodiment, the subject is a human.

In still another aspect, a method of identifying a binding partner to a polypeptide of the present invention described herein, or biologically active portion thereof, is provided comprising: a) contacting the polypeptide or biologically active portion thereof, or a cell expressing the polypeptide or biologically active portion thereof, with a test compound; and b) determining whether the polypeptide or biologically active portion thereof binds to the test compound.

In yet another aspect, a cell-based assay for screening for compounds which modulate the expression and/or activity of a polypeptide described herein or biologically active portion thereof is provided comprising contacting a cell expressing the polypeptide or biologically active portion thereof with a test compound and determining the ability of the test compound to modulate the expression and/or activity of the polypeptide or biologically active portion thereof.

In another aspect, a method for identifying a compound which modulates the expression and/or activity of a polypeptide described herein or biologically active portion thereof comprising: a) contacting the polypeptide or biologically active portion thereof with a test compound; and b) determining the effect of the test compound on the expression and/or activity of the polypeptide or biologically active portion thereof to thereby identify a compound which modulates the activity of the polypeptide or biologically active portion thereof.

In still another aspect, an isolated monoclonal antibody or antigen binding portion thereof that specifically binds to a polypeptide of the present invention described herein is provided.

In yet another aspect, a non-human animal model engineered to express a polypeptide of the present invention described herein is provided.

In another aspect, a method for assessing the efficacy of an agent that modulates FNDC5 expression and/or activity for modulating a metabolic response in a subject, comprising: a) detecting in a subject sample at a first point in time, the expression and/or activity of FNDC5; b) repeating step a) during at least one subsequent point in time after administration of the agent; and c) comparing the expression and/or activity detected in steps a) and b), wherein a significantly lower expression and/or activity of FNDC5 expression and/or activity in the first subject sample relative to at least one subsequent subject sample, indicates that the agent increases the metabolic response in the subject and/or wherein a significantly higher expression and/or activity of a marker listed in Table 2 in the first subject sample relative to at least one subsequent subject sample, indicates that the test agent decreases the metabolic response in the subject.

BRIEF DESCRIPTION OF FIGURES

FIGS. 1A-1B show the results of quantitative PCR (qPCR) analyses of brown fat genes in epidydimal, brown adipose tissue (BAT; FIG. 1A) and inguinal (FIG. 1B) fat depots in MCK-PGC1α transgenics or littermate controls (n=7 for each group, repeated in a separate cohort with similar results). FIG. 1C shows representative immunohistochemistry against UCP1 in the inguinal depot from indicated mice. FIG. 1D shows results of Western blot analyses against UCP1 in the inguinal fat depot (n=3 and repeated in an independent cohort with similar results). FIG. 1E shows the results of RT-PCR analyses of the indicated genes in primary stromo vascular fraction (SVF), differentiated to adipocytes for 6 days in the presence of conditioned media from GFP or PGC1α over expressing primary myocytes (representative for 3 independent experiments). Data is presented as mean±SEM. * p<0.05 using students T-TEST.

FIG. 2A shows the results of qPCR analyses of inguinal (subcutaneous), epidydimal (visceral) or intrascapular brown fat (BAT) depots against indicated genes in mice after three weeks of free wheel running or sedentary controls. Each group had n=10 mice. FIGS. 2B-2C shows the results of qPCR analyses of inguinal (subcutaneous) (FIG. 2B) and epidydimal (visceral)) (FIG. 2C) fat against indicated genes in mice after three weeks of swimming exercise (methods). Each group had n=10 mice. * p<0.05 compared to control using students T-TEST.

FIG. 3A shows the results of qPCR analyses of the indicated genes in skeletal muscle from MCK-PGC1α transgenics or littermate controls (n=7 from each group). FIG. 3B shows the results of qPCR analyses of the indicated genes in skeletal muscle from sedentary mice or mice exercised with three weeks of free wheel running (n=10 from each group). FIG. 3C shows the expression levels of the indicated genes from human muscle biopsies before and after the exercise protocol (8 subjects included). All data points are normalized to baseline levels. FIG. 3D shows gene expression from SVF from the inguinal fat depot, differentiated into adipocytes for 6 days in the presence of Saline or recombinant Fndc5 (20 nM), Il-15 (10 μM) or VEGFβ (50 μM). The graph shows normalized mRNA levels of indicated genes. This experiment was repeated several times with similar results. Data is presented as mean±SEM. * p<0.05 using students T-TEST.

FIG. 5 shows the results of gene expression analyses for all genes significantly altered in gene expression arrays after 6 days of Fndc5 treatment of SVF cells during differentiation compared to saline control. Genes up regulated >4-fold or down regulated to <0.4 fold are shown. FC=fold change and the "p=" column indicates p-value using T-TEST.

FIG. 6A shows 8 genes significantly induced with p<0.05 on gene expression arrays, with highest fold change in SVF treated with Fndc5 for 8 days. Brown fat genes are marked in bold. FIG. 6B shows analyses of SVF from the inguinal fat depot, differentiated into adipocytes for 6 days in the presence of Saline, recombinant Fndc5 (20 nM), or BMP-7 (3.3 μM). The graph shows normalized mRNA levels of indicated genes. Similar results were obtained in more than 10 experiments with the fold induction of UCP1 between 10-500 fold. FIG. 6C shows representative immunohistochemical images against UCP-1 in SVF differentiated into adipocytes for 6 days in the presence of saline or recombinant Fndc5 (20 nM). The right graph shows BioPix® quantification of UCP-1 positive cells in totally 40 random images per group. FIG. 6D shows representative electron microscopy images of SVF differentiated into adipocytes for 6 days in the presence of Saline or recombinant Fndc5 (20 nM). FIG. 6E shows Clark electrode measurements of oxygen consumption in SVF from the inguinal fat depot, differentiated into adipocytes for 6 days in the presence of saline or recombinant Fndc5 (20 nM). Data is representative for three independent experiments. Data is presented as mean±SEM. * p<0.05 compared to control using students T-TEST.

FIG. 7A shows the results of qPCR analyses of SVF from the inguinal fat depot, differentiated into adipocytes for 6 days and treated with 20 nM Fndc5 at different days of differentiation, as indicated. This experiment was repeated once with similar results. FIG. 7B shows the results of qPCR analyses of SVF, differentiated into adipocytes, and treated with Fndc5 or saline for 6 days followed by addition of forskolin for 8 hours. The graph shows qPCR of UCP-1 mRNA. § indicates p<0.05 compared to forskolin treatment. FIG. 7C shows the results of qPCR analyses against PPARα after 6 days of Fndc5 treatment (20 nM) during differentiation of primary SVF. FIG. 7D shows qPCR analyses of SVF, differentiated into adipocytes, and treated with Fndc5 and/or GW6471 for 6 days. The graph shows qPCR of indicated genes, and § indicates p<0.05 compared to Fndc5 treatment. Data is presented as mean±SEM. * p<0.05 compared to control using students T-TEST, or when multiple groups were used; one-way ANOVA.

FIG. 8A shows a schematic representation of the Fndc5 (SEQ ID NO: 2) gene structure (top panel) and two flag-constructs (middle and bottom panels). SP=signal peptide, H=hydrophobic domain, C=C-terminal domain. FIG. 8B shows the results of HEK293 cells transfected with a vector expressing the C-terminal flag tagged Fndc5 (CTF-F5, bottom panel), followed by isolation of cell and media protein. Samples were adjusted for protein content and Western blot was performed against FLAG (left panel) or Fndc5 (right panel). This was repeated in several experiments with similar results. Adjusting for volume also rendered similar results. FIG. 8C shows a representation of the full length Fndc5 (SEQ ID NO: 2) and the media fragment mapped with mass spectrometry (bold and underlined). FIG. 8D shows HEK293 cells transfected with a vector expressing CTF-F5, followed by isolation of cell and media protein. Respective protein fraction were then treated with PNGase F followed by Western blot against Irisin. FIG. 8E shows the results of tagged Irisin purified from cell supernatants, treated with PNGase F, and visualized using Coomassie staining FIG. 8F shows Western blot results against Fndc5 in serum from control or exercised mice. The bottom panel shows a quantification of the bands. FIG. 8G shows Western blot results against Irisin in serum from subjects before and after a period of endurance exercise. Eight subjects were analyzed and quantification after internal normalization is displayed in bottom panel. Data is presented as mean±SEM. * $p<0.05$ compared to control using students T-TEST.

FIG. 9 shows the homology between the mouse and human Fndc5 (SEQ ID NOs: 2 and 54, respectively). Gray underlined bar marks Irisin.

FIG. 10A shows the results of anti-FLAG Western blot analysis against albumin/IgG-cleared and deglycosylated plasma from mice injected with GFP or NTF-Fndc5 expressing adenovirus. FIG. 10B shows the results of anti-Fndc5 Western blot against albumin/IgG-cleared and deglycosylated plasma from PGC1α muscle knockout mice or flox/flox controls. FIG. 10C shows the results of Western blot analyses of four human serum samples where the primary antibody has been pre-incubated with either recombinant Fndc5 (right) or BSA (left).

FIG. 11A shows the results of Western blot analyses against Fndc5 in plasma from Irisin or GFP adenoviral injected mice. FIG. 11B-11D show body weights (FIG. 11B), accumulated food intake (FIG. 11C), and activity measures (FIG. 11D) from mice on high fat diet, 10 days after injection with Fndc5 or GFP expressing adenovirus, as analyzed using the CLAM technique. n=7 mice and * $p<0.05$ compared to control using students T-TEST. These results were observed in one additional mouse cohort.

FIG. 12A shows the results of wild type BALB/c mice injected with $10^{10}$ GFP- or Irisin-expressing adenoviral particles intravenously. Data shows qPCR (FIG. 12A) and protein (FIG. 12B) measurements of the indicated genes in the inguinal fat depot. FIG. 12C shows representative immunohistochemistry images against UCP-1 in inguinal fat. n=14 mice for both groups. FIGS. 12D-12F show in vivo oxygen consumption (FIG. 12D), fasting-insulin (FIG. 12E) and IGTT (FIG. 12F) in B6 mice after 18 weeks of high fat diet (HFD) and intravenous injection of GFP- or Irisin-expressing adenovirus. Seven mice were included in both groups, and all measures were repeated in a separate mouse cohort with similar results. * $p<0.05$ compared to control using students T-TEST.

DETAILED DESCRIPTION OF THE INVENTION

Figure 1:
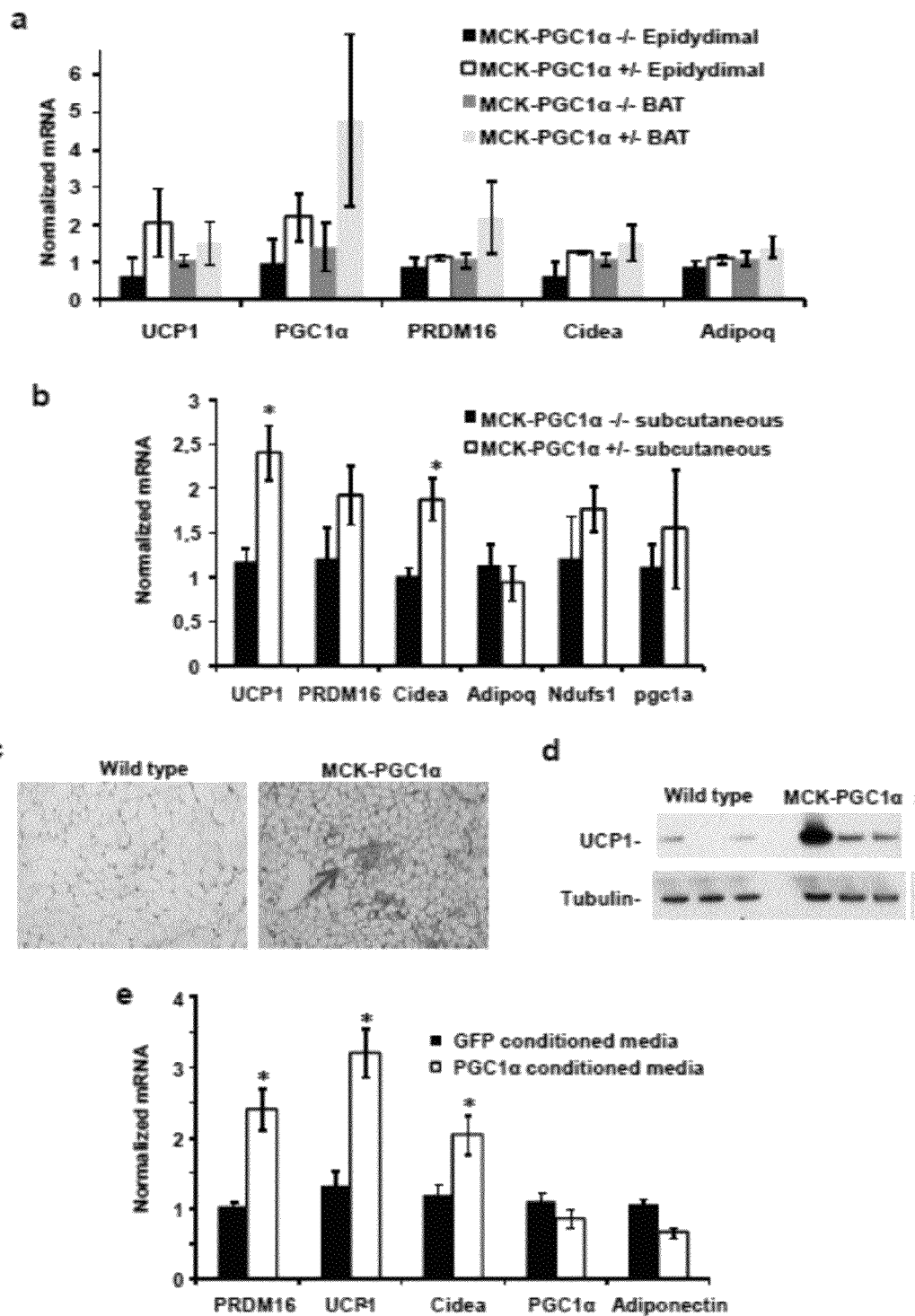
FIGS. 1A-1E show that muscle-specific PGC1α transgenic mice have increased brown fat in the subcutaneous depot.

The present invention is based in part on the discovery that Fndc5 and biologically active fragments thereof are secreted polypeptides that have the ability, even at nanomolar concentrations, to induce significant induction of brown fat cells. Functional brown fat cells can be differentiated from primary adipocyte cells upon expression and/or activity of Fndc5 or biologically active fragments thereof. The compositions described herein are capable of activating a distinct set of target genes (including, for example but not limited to, cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio2) characteristic of brown fat cells or downstream effects of brown fat cells. For example, increased brown fat cell induction in mammals using Fndc5 and biologically active fragments thereof induces the expression of mitochondrial genes (including, for example but not limited to, cytochrome c, cox 4i1, cox III, cox 5b, cox8b, atpase b2, cox II, atp5o and ndufb5); increases cellular respiration (i.e., total and uncoupled respiration); increases insulin sensitivity and thermogenesis of adipose cells; increases insulin sensitivity of muscle and hepatic cells; decreases hepatosteatosis, obesity, type II diabetes, and appetite; increases insulin secretion of pancreatic beta cells; increases cardiac function to combat cardiac hypertrophy; improves muscle hypoplasia; and reduces the growth and effects of obesity-associated cancer, cachexia, and anorexia.

It is demonstrated herein that PGC1α expression in muscle stimulates an increase in expression of Fndc5, a membrane protein that is cleaved and secreted as a novel hormone, Irisin. Irisin can act on cells (e.g., white adipose cells) in culture and in vivo to stimulate UCP1 expression and a broad program of brown fat-like development. Irisin is induced with exercise in both mouse and man, and mildly increased Irisin blood levels cause an increase in energy expenditure in mice with no change in movement or food intake. This results in improvement in metabolic disorders (e.g., obesity, insulin resistance, and glucose homeostasis).

In order that the present invention may be more readily understood, certain terms are first defined. Additional definitions are set forth throughout the detailed description.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intracellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, "obesity" refers to a body mass index (BMI) of 30 kg/m$^2$ or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/m$^2$ or more, 26 kg/m$^2$ or more, 27 kg/m$^2$ or more, 28 kg/m$^2$ or more, 29 kg/m$^2$ or more, 29.5 kg/m$^2$ or more, or 29.9 kg/m$^2$ or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

As used herein, the terms "Fndc5" and "Frcp2" refer to fibronectin type III domain containing 5 protein and are intended to include fragments, variants (e.g., allelic variants) and derivatives thereof. The nucleotide and amino acid sequences of mouse Fndc5, which correspond to Genbank Accession number NM_027402.3 and NP_081678.1 respectively, are set forth in SEQ ID NOs: 1 and 2. At least three splice variants encoding distinct human Fndc5 isoforms exist (isoform 1, NM_001171941.1, NP_001165412.1; isoform 2, NM_153756.2, NP_715637.1; and isoform 3, NM_001171940.1, NP_001165411). The nucleic acid and polypeptide sequences for each isoform is provided herein as SEQ ID NOs: 3-8, respectively. Nucleic acid and polypeptide sequences of FNDC5 orthologs in organisms other than mice and human are well known and include, for example, chicken FNDC5 (XM_417814.2; XP_417814.2) and zebrafish FNDC5 (XM_001335368.1; XP_001335404.1).

In some embodiments, fragments of Fndc5 having one or more biological activities of the full-length Fndc5 protein are described and employed. Such fragments can comprise or consist of at least one fibronectin domain of an Fndc5 protein without containing the full-length Fndc5 protein sequence. In some embodiments, Fndc5 fragments can comprise or consist of a signal peptide, extracellular, fibronectin, hydrophobic, and/or C-terminal domains of an Fndc5 protein without containing the full-length Fndc5 protein sequence. As further indicated in the Examples, Fndc5 orthologs are highly homologous and retain common structural domains well known in the art. In other embodiments, the term "Irisin" refers to the fragment representing residues 30-140 of SEQ ID NO: 2.

TABLE 1

```
SEQ ID NO: 1 Mouse Fndc5 cDNA Sequence
atg ccc cca ggg ccg tgc gcc tgg ccg ccc cgc gcc gcg ctc cgc ctg tgg cta ggc tgc
gtc tgc ttc gcg ctg gtg cag gcg gac agc ccc tca gcc cct gtg aac gtg acc gtc cgg
cac ctc aag gcc aac tct gcc gtg gtc agc tgg gat gtc ctg gag gat gaa gtg gtc att
ggc ttt gcc atc tct cag cag aag aag gat gtg cgg atg ctc cgg ttc att cag gag gtg
```

TABLE 1 -continued

```
aac acc acc acc cgg tcc tgc gct ctc tgg gac ctg gag gag gac aca gaa tat atc gtc
cat gtg cag gcc atc tcc atc cag gga cag agc cca gcc agt gag cct gtg ctc ttc aag
acc cca cgc gag gct gaa aag atg gcc tca aag aac aaa gat gag Gtg acc atg aag gag
atg ggg agg aac cag ctg cga acg (ggg) gag gtg ctg atc att gtt gtg gtc ctc
ttc atg tgg gca ggt gtt ata gct ctc ttc tgc cgc cag tat gat atc Atc aag gac aac
gag ccc aat aac aac aag gag aaa acc aag agc gca tca gaa acc agc Aca ccg gag cat
cag ggt ggg ggt ctc ctc cgc agc aag ata tga
```

SEQ ID NO: 2 Mouse Fndc5 Amino Acid Sequence
M P P G P C A W P P R A A L R L W L G C V C F A L V Q A D S P S A P V N V T V
R H L K A N S A V V S W D V L E D E V V I G F A I S Q Q K K D V R M L R F I Q
E V N T T T R S C A L W D L E E D T E Y I V H V Q A I S I Q G Q S P A S E P V
L F K T P R E A E K M A S K N K D E V T M K E M G R N Q Q L R T G E V L I I V
V V L F M W A G V I A L F C R Q Y D I I K D N E P N N N K E K T K S A S E T S
T P E H Q G G G L L R S K I SEQ ID NO: 3 Human Fndc5 (isoform 1) cDNA Sequence
```
  1 atgctgcgct tcatccagga ggtgaacacc accaccgct catgtgccct ctgggacctg
 61 gaggaggata cggagtacat agtccacgtg caggccatct ccattcaggg ccagagccca
121 gccagcgagc ctgtgctctt caagacccct cgtgaggctg agaagatggc ctccaagaac
181 aaagatgagg taaccatgaa agagatgggg aggaaccaac agctgcggac aggcgaggtg
241 ctgatcatcg tcgtggtcct gttcatgtgg gcaggtgtca ttgccctctt ctgccgccag
301 tatgacatca tcaaggacaa tgaacccaat aacaacaagg aaaaaaccaa gagtgcatca
361 gaaaccagca caccagagca ccagggcggg gggcttctcc gcagcaaggt gagggcaaga
421 cctgggcctg ggtgggccac cctgtgcctc atgctctggt aa
```

SEQ ID NO: 4 Human Fndc5 (isoform 1) Amino Acid Sequence
```
  1 mlrfiqevnt ttrscalwdl eedteyihv qaisiqgqsp asepvlfktp reaekmaskn
 61 kdevtmkemg rnqqlrtgev liivvlfmw agvialfcrq ydiikdnepn nnkektksas
121 etstpehqgg gllrskvrar pgpgwatlcl mlw
```

SEQ ID NO: 5 Human Fndc5 (isoform 2) cDNA Sequence
```
  1 atgctgcgct tcatccagga ggtgaacacc accaccgct catgtgccct ctgggacctg
 61 gaggaggata cggagtacat agtccacgtg caggccatct ccattcaggg ccagagccca
121 gccagcgagc ctgtgctctt caagacccct cgtgaggctg agaagatggc ctccaagaac
181 aaagatgagg taaccatgaa agagatgggg aggaaccaac agctgcggac aggcgaggtg
241 ctgatcatcg tcgtggtcct gttcatgtgg gcaggtgtca ttgccctctt ctgccgccag
301 tatgacatca tcaaggacaa tgaacccaat aacaacaagg aaaaaaccaa gagtgcatca
361 gaaaccagca caccagagca ccagggcggg gggcttctcc gcagcaagat atga
```

SEQ ID NO: 6 Human Fndc5 (isoform 2) Amino Acid Sequence
```
  1 mlrfiqevnt ttrscalwdl eedteyihv qaisiqgqsp asepvlfktp reaekmaskn
 61 kdevtmkemg rnqqlrtgev liivvlfmw agvialfcrq ydiikdnepn nnkektksas
121 etstpehqgg gllrski
```

SEQ ID NO: 7 Human Fndc5 (isoform 3) cDNA Sequence
```
  1 atgctgcgct tcatccagga ggtgaacacc accaccgct catgtgccct ctgggacctg
 61 gaggaggata cggagtacat agtccacgtg caggccatct ccattcaggg ccagagccca
121 gccagcgagc ctgtgctctt caagacccct cgtgaggctg agaagatggc ctccaagaac
181 aaagatgagg taaccatgaa agagatgggg aggaaccaac agctgcggac aggcgaggtg
241 ctgatcatcg tcgtggtcct gttcatgtgg gcaggtgtca ttgccctctt ctgccgccag
301 tatgacatca ttgaagcgtg a
```

SEQ ID NO: 8 Human Fndc5 (isoform 3) Amino Acid Sequence
```
  1 mlrfiqevnt ttrscalwdl eedteyihv qaisiqgqsp asepvlfktp reaekmaskn
 61 kdevtmkemg rnqqlrtgev liivvlfmw agvialfcrq ydiiea
```

SEQ ID NO: 9 Chicken Fndc5 cDNA Sequence
```
   1 atggagaaga cagggacgg ccgcggcccc cctggtgtcc atctggggat ggagaaggaa
  61 gatgatttag agcccggtga cacgccgggg ctgcgcgaag ccctggtggc gagatgtcac
 121 cgctgccgcg cacccgccgg gggtctcacc gggacgggcc ccgtttgctc cttccggcga
 181 tggggagcgg tccgggccga gggctcccgg tcccgcctgg ggaaactga ggcagacggc
 241 ggggccgggc ggggcggggg ccgagccgcc ccggggccgg gggagggacc ggagcggggc
 301 tgcccagcgc tgcagcgggc ggagccgggg ctcggcgggg ccgcctcccg gccgagccga
 361 gccgaaccga gccgcgctgc cgagggccgc cgagcccgca gccgccccg gccgaaccgg
 421 gcggccccgc cggttccggg ccccggagct tcccgcggtg ctgaacggcg ccgccgcgcc
 481 cgcgggacgc cggccccgga gcggctcggc cccggcgcgg cggcggggc cgcgggggga
 541 tggagccctt cctgggctgc accgcgccg cgctcctgct ctgctttcag ctacgccggt
 601 ctgcggccgt ggaggcaga cagcccttcg gctccggtca atgtcacagt caaacacctg
 661 aaggccaact cagctgtagt gacttgggac gttctggagg atgaagttgt cattggattt
 721 gccatttccc agcagaagaa ggacgtgcgg atgctgcgct tcatccagga ggtgaacacc
 781 accaccgct cctgtgccct ctgggaccta gaggaggaca ctgagtacat tgtgcatgtc
 841 caggccatca catccaagg ccagagccct gccagtgagc cagtcctctt caagaccccc
 901 agggaagctg agaaactggc ttctaaaaat aaagatgagg tgacaatgaa ggagatggcg
 961 aagaaaaacc aacagctgcg gcagggaa atactcatca ttgtggtggt gttgtttatg
1021 tgggcagggg tgatcgccct gttctgcagg cagtacgaca tcatcaaaga caacgagccg
1081 aacaacagca aggagaaagc caagagcgcc tcagaatacca gcaccccga gcaccagggt
1141 ggggggctgc tccgcagcaa gttcccaaaa aacaaaccct cagtgaacat cattgaggca
1201 taa
```

TABLE 1 -continued

```
SEQ ID NO: 10 Chicken Fndc5 Amino Acid Sequence
    1 meknrdgrgp pgvhlgmeke ddlepgdtpg lrealvarch rcrapagglt gtgpvcsfrr
   61 wgavraegsr srlgeteadg gagrgggraa pgpgegperg cpalqraepg lggaasrpsr
  121 aepsraaegr rarsrprpnr aappvpgpga lrgaerrrra rgtpaperlg pgaarraagg
  181 wspswaapap rscsafsyag lrpveadsps apvnvtvkhl kansavvtwd vledevvigf
  241 aisqqkkdvr mlrfiqevnt ttrscalwdl eedteyivhv qaisiqgqsp asepvlfktp
  301 reaeklaskn kdevtmkema kknqqlrage iliivvvlfm wagvialfcr qydiikdnep
  361 nnskekaksa senstpehqg ggllrskfpk nkpsvniiea SEQ ID NO: 11 Zebrafish Fndc5 cDNA Sequence
    1 atgagttctt acagtttggc agctccagtg aatgtgtcca tcagggatct gaagagcagc
   61 tcagccgtgg tgacatggga cacgccagac ggagagccag tcatcggctt cgccatcaca
  121 caacagaaga aagatgtccg catgctgcgc tttattcaag aagtgaacac caccacgcgg
  181 agctgtgcat tgtgggatct ggaagctgat acggattaca ttgtgcacgt tcagtctatc
  241 agcatcagcg gggcgagtcc tgttagtgaa gctgtgcact tcaagacccc gacagaagtt
  301 gaaacacagg cctccaagaa caaagacgag gtgacgatgg aggaggtcgg gccgaacgct
  361 cagctcaggg ccggagagtt catcattatt gtggtggtcc tcatcatgtg ggcaggtgtg
  421 atcgcactat tctgccgtca gtatgacatc attaaagaca acgaaccaaa caataacaag
  481 gataaagcca agaactcgtc tgaatgcagc actccagagc acacgtcagg tggcctgctg
  541 cgcagtaagg tataa SEQ ID NO: 12 Zebrafish Fndc5 Amino Acid Sequence
    1 mssyslaapv nvsirdlkss savvtwdtpd gepvigfait qqkkdvrmlr fiqevntttr
   61 scalwdlead tdyivhvqsi sisgaspvse avhfktptev etqasknkde vtmeevgpna
  121 qlragefiii vvvlimwagv ialfcrqydi ikdnepnnnk dkaknssecs tpehtsggll
  181 rskv SEQ ID NO: 13 Fragment of Murine Fndc5 Nucleic Acid Sequence that encodes
amino acid residues 29-140 of murine Fndc5
  104                                                 gacagcc cctcagcccc
  121 tgtgaacgtg accgtccggc acctcaaggc caactctgcc gtggtcagct gggatgtcct
  181 ggaggatgaa gtggtcattg gctttgccat ctctcagcag aagaaggatg tgcggatgct
  241 ccggttcatt caggaggtga acaccaccac ccggtcctgc gctctctggg acctggagga
  301 ggacacagaa tatatcgtcc atgtgcaggc catctccatc cagggacaga gcccagccag
  361 tgagcctgtg ctcttcaaga ccccacgcga ggctgaaaag atggcctcaa agaacaaaga
  421 tgaggtgacc atgaaggag SEQ ID NO: 14 Amino acid sequence of residues 29-140 of murine Fndc5
D S P S A P V N V T V R H L K A N S A V V S W D V L E D E V V I G F A
I S Q Q K K D V R M L R F I Q E V N T T T R S C A L W D L E E D T E Y
I V H V Q A I S I Q G Q S P A S E P V L F K T P R E A E K M A S K N K
D E V T M K E M G R N Q Q L R T G E V L I I V V L F M W A G V I A L
F C R Q Y D I I K D N E P N N N K E K T K S A S E T S T P E H Q G G G
L L R S K I SEQ ID NO: 15: Fragment of Human Fndc5 Nucleic Acid Sequence
  161                                                 gacagtccct cagcccagt
  181 gaacgtcacc gtcaggcacc tcaaggccaa ctctgcagtg gtgagctggg atgttctgga
  241 ggatgaggtt gtcatcggat ttgccatctc ccagcagaag aaggatgtgc ggatgctgcg
  301 cttcatccag gaggtgaaca ccaccacccg ctcatgtgcc ctctgggacc tggaggagga
  361 tacggagtac atagtccacg tgcaggccat ctccattcag ggccagagcc cagccagcga
  421 gcctgtgctc ttcaagaccc cgcgtgaggc tgagaagatg gcctccaaga acaaagatga
  481 ggtaaccatg aaagag
```

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein (e.g., cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio2), are well known in the art and can be used in the embodiments of the invention.

I. Isolated Nucleic Acids

One aspect of the invention pertains to methods utilizing isolated nucleic acid molecules that encode Fndc5 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Fndc5 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO: 1, 3, 5, 7, 9, 11, 13 and 15 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, 5, 7, 9, 11, 13 and 15 or a portion thereof (i.e., 100, 200, 300, 400, 450, 500, or more nucleotides), can be isolated using standard molecular biology techniques and the sequence information provided herein. For example, a human Fndc5 cDNA can be isolated from a human muscle cell line (from Stratagene, LaJolla, Calif., or Clontech, Palo Alto, Calif.) using all or portion of SEQ ID NOs: 1, 3, 5, 7, 9, 11, 13 or 15, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NOs: 1, 3, 5, 7, 9, 11, 13 or 15 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, 5, 7, 9, 11, 13 or 15, or fragment thereof, can be isolated by the polymerase chain reaction using oligonucleotide primers designed based upon the sequence of SEQ ID NOs: 1, 3, 5, 7, 9, 11, 13 or 15, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, 5, 7, 9, 11, 13 or 15, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an Fndc5 nucleotide sequence can be prepared by standard synthetic techniques, i.e., using an automated DNA synthesizer.

Probes based on the Fndc5 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express an Fndc5 protein, such as by measuring a level of an Fndc5-encoding nucleic acid in a sample of cells from a subject, i.e., detecting Fndc5 mRNA levels.

Nucleic acid molecules encoding other Fndc5 members and thus which have a nucleotide sequence which differs from the Fndc5 sequences of SEQ ID NOs: 1, 3, 5, 7, 9, 11, 13 or 15, or fragment thereof, are contemplated. Moreover, nucleic acid molecules encoding Fndc5 proteins from different species, and thus which have a nucleotide sequence which differs from the Fndc5 sequences of SEQ ID NOs: 1, 3 5, 7, 9, 11, 13 or 15 are also intended to be within the scope of the present invention. For example, rat or monkey Fndc5 cDNA can be identified based on the nucleotide sequence of a human and/or mouse Fndc5.

In one embodiment, the nucleic acid molecule(s) of the invention encodes a protein or portion thereof which includes an amino acid sequence which is sufficiently homologous to an amino acid sequence of SEQ ID NO: 2, 4, 6, 8, 10, 12 or 14, or fragment thereof, such that the protein or portion thereof modulates (e.g., enhance), one or more of the following biological activities: 1) it can modulate the expression of cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; and 10) it can treat diseases or disorders characterized by increased PGC-1 expression or activity, e.g., diabetes or obesity.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, 6, 8, 10, 12 or 14, or fragment thereof) amino acid residues to an amino acid sequence of SEQ ID NO: 2, 4, 6, 8, 10, 12 or 14, or fragment thereof, such that the protein or portion thereof modulates (e.g., enhance) one or more of the following biological activities: 1) it can modulate the expression of cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; and 10) it can treat diseases or disorders characterized by increased PGC-1 expression or activity, e.g., diabetes or obesity.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of SEQ ID NO: 2, 4, 6, 8, 10, 12 or 14, or fragment thereof, or a fragment thereof.

Portions of proteins encoded by the Fndc5 nucleic acid molecule of the invention are preferably biologically active portions of the Fndc5 protein. As used herein, the term "biologically active portion of Fndc5" is intended to include a portion, e.g., a domain/motif, of Fndc5 that has one or more of the biological activities of the full-length Fndc5 protein.

Standard binding assays, e.g., immunoprecipitations and yeast two-hybrid assays, as described herein, or functional assays, e.g., RNAi or overexpression experiments, can be performed to determine the ability of an Fndc5 protein or a biologically active fragment thereof to maintain a biological activity of the full-length Fndc5 protein.

The invention further encompasses nucleic acid molecules that differ from the nucleotide sequence shown in SEQ ID NO: 1, 3, 5, 7, 9, 11, 13 or 15, or fragment thereof due to degeneracy of the genetic code and thus encode the same Fndc5 protein as that encoded by the nucleotide sequence shown in SEQ ID NO: 1, 3, 5, 7, 9, 11, 13 or 15, for fragment thereof. In another embodiment, an isolated nucleic acid molecule of the invention has a nucleotide sequence encoding a protein having an amino acid sequence shown in SEQ ID NO: 2, 4, 6, 8, 10, 12 or 14, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of SEQ ID NO: 2, 4, 6, 8, 10, 12 or 14, or fragment thereof, or a fragment thereof, or differs by at least 1, 2, 3, 5 or 10 amino acids but not more than 30, 20, 15 amino acids from SEQ ID NO: 2, 4, 6, 8, 10, 12 or 14. In another embodiment, a nucleic acid encoding an Fndc5 polypeptide consists of nucleic acid sequence encoding a portion of a full-length Fndc5 fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of Fndc5 may exist within a population (e.g., a mammalian population, e.g., a human population). Such genetic polymorphism in the Fndc5 gene may exist among individuals within a population due to natural allelic variation. As used herein, the terms "gene" and "recombinant gene" refer to nucleic acid molecules comprising an open reading frame encoding an Fndc5 protein, preferably a mammalian, e.g., human, Fndc5 protein. Such natural allelic variations can typically result in 1-5% variance in the nucleotide sequence of the Fndc5 gene. Any and all such nucleotide variations and resulting amino acid polymorphisms in Fndc5 that are the result of natural allelic variation and that do not alter the functional activity of Fndc5 are intended to be within the scope of the invention. Moreover, nucleic acid molecules encoding Fndc5 proteins from other species, and thus which have a nucleotide sequence which differs from the human or mouse sequences of SEQ ID NO: 1, 3, 5, or 7, are intended to be within the scope of the invention. Nucleic acid molecules corresponding to natural allelic variants and homologues of the human or mouse Fndc5 cDNAs of the invention can be isolated based on their homology to the human or mouse Fndc5 nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Fndc5 sequence that may exist in the population, the skilled artisan will further appreciate that changes can be introduced by mutation into the nucleotide sequence of SEQ ID NO: 1, 3, 5, 7, 9, 11, 13 or 15, or fragment thereof, thereby leading to changes in the amino acid sequence of the encoded Fndc5 protein, without altering the functional ability of the Fndc5 protein. For example, nucleotide substitutions leading to amino acid substitutions at "non-essential" amino acid residues can be made in the sequence of SEQ ID NO: 1, 3, 5, 7, 9, 11, 13 or 15, or fragment thereof. A "non-essential" amino acid residue is a residue that can be altered from the wild-type sequence of Fndc5 (e.g., the sequence of SEQ ID NO: 2, 4, 6, 8, 10, 12 or 14, or fragment thereof) without altering the activity of Fndc5, whereas an "essential" amino acid residue is required for Fndc5 activity. Other amino acid residues, however, (e.g., those that are not conserved or only semi-conserved between mouse and human) may not be essential for activity and thus are likely to be amenable to alteration without altering Fndc5 activity. Furthermore, amino acid residues that are essential for Fndc5 functions related to thermogenesis and/or adipogenesis, but not essential for Fndc5 functions related to gluconeogenesis, are likely to be amenable to alteration.

Accordingly, another aspect of the invention pertains to nucleic acid molecules encoding Fndc5 proteins that contain changes in amino acid residues that are not essential for Fndc5 activity. Such Fndc5 proteins differ in amino acid sequence from SEQ ID NO: 2, 4, 6, 8, 10, 12 or 14, or fragment thereof, yet retain at least one of the Fndc5 activities described herein. In one embodiment, the isolated nucleic acid molecule comprises a nucleotide sequence encoding a protein, wherein the protein lacks one or more Fndc5 domains (e.g., a fibronectin, extracellular, signal peptide, hydrophobic, and/or C-terminal domain).

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared ×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6.

In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding an Fndc5 protein homologous to the protein of SEQ ID NO: 2, 4, 6, 8, 10, 12 or 14, or fragment thereof, can be created by introducing one or more nucleotide substitutions, additions or deletions into the nucleotide sequence of SEQ ID NO: 1, 3, 5, 7, 9, 11, 13 or 15, or fragment thereof, or a homologous nucleotide sequence such that one or more amino acid substitutions, additions or deletions are introduced into the encoded protein. Mutations can be introduced into SEQ ID NO: 1, 3, 5, 7, 9, 11, 13 or 15, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), bet217-420ranched side chains (e.g., threonine, valine, isoleucine) and aromatic side chains (e.g., tyrosine, phenylalanine, tryptophan, histidine). Thus, a predicted nonessential amino acid residue in Fndc5 is preferably replaced with another amino acid residue from the same side chain family. Alternatively, in another embodiment, mutations can be introduced randomly along all or part of an Fndc5 coding sequence, such as by saturation mutagenesis, and the resultant mutants can be screened for an Fndc5 activity described herein to identify mutants that retain Fndc5 activity. Following mutagenesis of SEQ ID NO: 1, 3, 5, 7, 9, 11, 13 or 15, or fragment thereof, the encoded protein can be expressed recombinantly (as described herein) and the activity of the protein can be determined using, for example, assays described herein.

Fndc5 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Fndc5 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Fndc5 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding Fndc5. Other suitable probes for use in the diagnostic assays of the invention are described herein. Hybridization of an mRNA with the probe indicates that Fndc5 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the Fndc5 mRNA expression levels.

An alternative method for determining the Fndc5 mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the Fndc5 mRNA.

As an alternative to making determinations based on the absolute Fndc5 expression level, determinations may be based on the normalized Fndc5 expression level. Expression levels are normalized by correcting the absolute Fndc5 expression level by comparing its expression to the expression of a non-Fndc5 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of an Fndc5 protein can also be detected and/or quantified by detecting or quantifying the expressed polypeptide. The Fndc5 polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Fndc5.

In addition to the nucleic acid molecules encoding Fndc5 proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Fndc5 coding strand, or to only a portion thereof. In one embodiment, an antisense nucleic acid molecule is antisense to a "coding region" of the coding strand of a nucleotide sequence encoding Fndc5. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Fndc5. The term "noncoding region" refers to 5' and 3' sequences which flank the coding region that are not translated into amino acids (i.e., also referred to as 5' and 3' untranslated regions).

In some embodiments, Fndc5 expression can be reduced using nucleic acid compositions described herein. For example, an "RNA interfering agent," as used herein, is defined as any agent which interferes with or inhibits expression of a target gene, e.g., Fndc5, by RNA interference (RNAi). Such RNA interfering agents include, but are not limited to, nucleic acid molecules including RNA molecules which are homologous to the target gene or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene or protein encoded by the target gene. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501 incorporated be reference herein).

RNA interfering agents, e.g., siRNA molecules, may be administered to a subject having or at risk for a condition described herein mediated by Fndc5, to inhibit expression of Fndc5 to thereby treat, prevent, or inhibit the condition in the subject.

II. Recombinant Expression Vectors and Host Cells

Another aspect of the invention pertains to the use of vectors, preferably expression vectors, containing a nucleic acid encoding Fndc5 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising an Fndc5 nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of Fndc5 in prokaryotic or eukaryotic cells. For example, Fndc5 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the Fndc5 is cloned into a pGEX expression vector to create a vector encoding a fusion protein comprising, from the N-terminus to the C-terminus, and/or GST-thrombin cleavage site-Fndc5. The fusion protein can be purified by affinity chromatography using glutathione-agarose resin. Recombinant Fndc5 unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the Fndc5 expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, Fndc5 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to Fndc5 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Fndc5 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., *Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. An Fndc5 polypeptide or fragment thereof, may be secreted and isolated from a mixture of cells and medium containing the polypeptide. Alternatively, an Fndc5 polypeptide or fragment thereof, may be retained cytoplasmically and the cells harvested, lysed and the protein or protein complex isolated. An Fndc5 polypeptide or fragment thereof, may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of Fndc5 or a fragment thereof. In other embodiments, heterologous tags can be used for purification purposes (e.g., epitope tags and FC fusion tags), according to standards methods known in the art.

Thus, a nucleotide sequence encoding all or a selected portion of an Fndc5 polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant Fndc5 polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the Fndc5 polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Fndc5 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Fndc5 protein. Accordingly, the invention further provides methods for producing Fndc5 protein using the host cells of the invention. In one embodiment, the method comprises culturing the host cell of invention (into which a recombinant expression vector encoding Fndc5 has been introduced) in a suitable medium until Fndc5 is produced. In another embodiment, the method further comprises isolating Fndc5 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which Fndc5 encoding sequences, or fragments thereof, have been introduced. Such host cells can then be used to create non-human transgenic animals in which exogenous Fndc5 sequences have been introduced into their genome or homologous recombinant animals in which endogenous Fndc5 sequences have been altered. Such animals are useful for studying the function and/or activity of Fndc5, or fragments thereof, and for identifying and/or evaluating modulators of Fndc5 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Fndc5 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding Fndc5, or a fragment thereof, into the male pronuclei of a fertilized oocyte, e.g., by microinjection, retroviral infection, and allowing the oocyte to develop in a pseudopregnant female foster animal. The human Fndc5 cDNA sequence can be introduced as a transgene into the genome of a nonhuman animal. Alternatively, a nonhuman homologue of the human Fndc5 gene can be used as a transgene. Intronic sequences and polyadenylation signals can also be included in the transgene to increase the efficiency of expression of the transgene. A tissue-specific regulatory sequence(s) can be operably linked to the Fndc5 transgene to direct expression of Fndc5 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Fndc5 transgene in its genome and/or expression of Fndc5 mRNA in tissues or cells of the animals. A transgenic founder animal can then be used to breed additional animals carrying the transgene. Moreover, transgenic animals carrying a transgene encoding Fndc5 can further be bred to other transgenic animals carrying other transgenes.

To create a homologous recombinant animal, a vector is prepared which contains at least a portion of an Fndc5 gene into which a deletion, addition or substitution has been introduced to thereby alter, e.g., functionally disrupt, the Fndc5 gene. The Fndc5 gene can be a human gene, but more preferably, is a nonhuman homologue of a human Fndc5 gene. For example, a mouse Fndc5 gene can be used to construct a homologous recombination vector suitable for altering an endogenous Fndc5 gene, respectively, in the mouse genome. In a preferred embodiment, the vector is designed such that, upon homologous recombination, the endogenous Fndc5 gene is functionally disrupted (i.e., no longer encodes a functional protein; also referred to as a "knock out" vector). Alternatively, the vector can be designed such that, upon homologous recombination, the endogenous Fndc5 gene is mutated or otherwise altered but still encodes functional protein (e.g., the upstream regulatory region can be altered to thereby alter the expression of the endogenous Fndc5 protein). In the homologous recombination vector, the altered portion of the Fndc5 gene is flanked at its 5' and 3' ends by additional nucleic acid of the Fndc5 gene to allow for homologous recombination to occur between the exogenous Fndc5 gene carried by the vector and an endogenous Fndc5 gene in an embryonic stem cell. The additional flanking Fndc5 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Fndc5 gene has homologously recombined with the endogenous Fndc5 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Fndc5 Polypeptides and Anti-Fndc5 Antibodies

The present invention provides soluble, purified and/or isolated forms of Fndc5, or fragments thereof.

In one aspect, an Fndc5 polypeptide may comprise a full-length Fndc5 amino acid sequence or a full-length Fndc5 amino acid sequence with 1 to about 20 conservative amino acid substitutions. Amino acid sequence of any Fndc5 polypeptide described herein can also be at least 50, 55, 60, 65, 70, 75, 80, 85, 90, 91, 92, 93, 94, 95, 96, 97, 98, 99, or 99.5% identical to an Fndc5 polypeptide sequence of interest, described herein, well known in the art, or a fragment thereof. In addition, any Fndc5 polypeptide, or fragment thereof, described herein has modulates (e.g., enhance) one or more of the following biological activities: 1) it can modulate the expression of cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; and 10) it can treat diseases or disorders characterized by increased PGC-1 expression or activity, .g., diabetes or obesity. In another aspect, the present invention contemplates a composition comprising an isolated Fndc5 polypeptide and less than about 25%, or alternatively 15%, or alternatively 5%, contaminating biological macromolecules or polypeptides.

The present invention further provides compositions related to producing, detecting, or characterizing an Fndc5 polypeptide, or fragment thereof, such as nucleic acids, vectors, host cells, and the like. Such compositions may serve as compounds that modulate an Fndc5 polypeptide's expression and/or activity, such as antisense nucleic acids.

In certain embodiments, an Fndc5 polypeptide of the invention may be a fusion protein containing a domain which increases its solubility and bioavailability and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, an Fndc5 polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 8, 9, 10, 15, 20 amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG (SEQ ID NO: 16). In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, Fndc5 polypeptides, or fragments thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et. al., 2001 Immunity 14:123 133. Fusion to an Fc polypeptide offers the additional advantage of facilitating purification by affinity chromatography over Protein A or Protein G columns.

In still another embodiment, an Fndc5 polypeptide may be labeled with a fluorescent label to facilitate their detection, purification, or structural characterization. In an exemplary embodiment, an Fndc5 polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated Fndc5 proteins, and biologically active portions thereof, as well as peptide fragments suitable for use as immunogens to raise anti-Fndc5 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Fndc5 protein in which the protein is separated from cellular components of the cells in which it is naturally or recombinantly produced. In one embodiment, the language "substantially free of cellular material" includes preparations of Fndc5 protein having less than about 30% (by dry weight) of non-Fndc5 protein (also referred to herein as a "contaminating protein"), more preferably less than about 20% of non-Fndc5 protein, still more preferably less than about 10% of non-Fndc5 protein, and most preferably less than about 5% non-Fndc5 protein. When the Fndc5 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Fndc5 protein in which the protein is separated from chemical precursors or other chemicals which are involved in the synthesis of the protein. In one embodiment, the language "substantially free of chemical precursors or other chemicals" includes preparations of Fndc5 protein having less than about 30% (by dry weight) of chemical precursors of non-Fndc5 chemicals, more preferably less than about 20% chemical precursors of non-Fndc5 chemicals, still more preferably less than about 10% chemical precursors of non-Fndc5 chemicals, and most preferably less than about 5% chemical precursors of non-Fndc5 chemicals. In preferred embodiments, isolated proteins or biologically active portions thereof lack contaminating proteins from the same animal from which the Fndc5 protein is derived. Typically, such proteins are produced by recombinant expression of, for example, a human Fndc5 protein in a nonhuman cell.

In preferred embodiments, the protein or portion thereof comprises an amino acid sequence which is sufficiently homologous to an amino acid sequence of SEQ ID NO: 2, 4, 6, 8, 10, 12 or 14, or fragment thereof, such that the protein or portion thereof maintains one or more of the following biological activities or, in complex, modulates (e.g., enhance) one or more of the following biological activities: 1) it can modulate the expression of cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; and 10) it can treat diseases or disorders characterized by increased PGC-1 expression or activity, e.g., diabetes or obesity. The portion of the protein is preferably a biologically active portion as described herein. In another preferred embodiment, the Fndc5 protein has an amino acid sequence shown in SEQ ID NO: 2, 4, 6, 8, 10, 12 or 14, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO: 2, 4, 6, 8, 10, 12 or 14, or fragment thereof. In yet another preferred embodiment, the Fndc5 protein has an amino acid sequence which is encoded by a nucleotide sequence which hybridizes, e.g., hybridizes under stringent conditions, to the nucleotide sequence of SEQ ID NO:1, 3, 5, 7, 9, 11, 13 or 15, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO: 1, 3, 5, 7, 9, 11, 13 or 15, or fragment thereof. The preferred Fndc5 proteins of the present invention also preferably possess at least one of the Fndc5 biological activities, or activities associated with the complex, described herein. For example, a preferred Fndc5 protein of the present invention includes an amino acid sequence encoded by a nucleotide sequence which hybridizes, e.g., hybridizes under stringent conditions, to the nucleotide sequence of SEQ ID NO:1, 3, 5, 7, 9, 11, 13 or 15, or fragment thereof and which can maintain one or more of the following biological activities or, in complex, modulates (e.g., enhance) one or more of the following biological activities: 1) it can modulate the expression of cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; and 10) it can treat diseases or disorders characterized by increased PGC-1 expression or activity, e.g., diabetes or obesity.

Biologically active portions of the Fndc5 protein include peptides comprising amino acid sequences derived from the amino acid sequence of the Fndc5 protein, e.g., the amino acid sequence shown in SEQ ID NO: 2, 4, 6, 8, 10, 12 or 14, or fragment thereof, or the amino acid sequence of a protein homologous to the Fndc5 protein, which include fewer amino acids than the full length Fndc5 protein or the full length protein which is homologous to the Fndc5 protein, and exhibit at least one activity of the Fndc5 protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., signal peptide, extracellular domain, fibronectin domain, hydrophobic, and/or C-terminal domain). In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the Fndc5 protein include one or more selected domains/motifs or portions thereof having biological activity. In an exemplary embodiment, an Fndc5 fragment comprises and/or consists of about amino acids 29-140, 29-150, 30-140, 30-150, 73-140, 73-150, 1-140, 1-150, or any range in between residues 1 and 150 of SEQ ID NO:2. In another embodiment, an Fndc5 fragment consists of a portion of a full-length Fndc5 fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

Fndc5 proteins can be produced by recombinant DNA techniques. For example, a nucleic acid molecule encoding the protein is cloned into an expression vector (as described above), the expression vector is introduced into a host cell (as described above) and the Fndc5 protein is expressed in the host cell. The Fndc5 protein can then be isolated from the cells by an appropriate purification scheme using standard protein purification techniques. Alternative to recombinant expression, an Fndc5 protein, polypeptide, or peptide can be synthesized chemically using standard peptide synthesis techniques. Moreover, native Fndc5 protein can be isolated from cells (e.g., brown adipocytes), for example using an anti-Fndc5 antibody (described further below).

The invention also provides Fndc5 chimeric or fusion proteins. As used herein, an Fndc5 "chimeric protein" or "fusion protein" comprises an Fndc5 polypeptide operatively linked to a non-Fndc5 polypeptide. A "Fndc5 polypeptide" refers to a polypeptide having an amino acid sequence corresponding to Fndc5, whereas a "non-Fndc5 polypeptide" refers to a polypeptide having an amino acid sequence corresponding to a protein which is not substantially homologous to the Fndc5 protein, respectively, e.g., a protein which is different from the Fndc5 protein and which is derived from the same or a different organism. Within the fusion protein, the term "operatively linked" is intended to indicate that the Fndc5 polypeptide and the non-Fndc5 polypeptide are fused in-frame to each other. The non-Fndc5 polypeptide can be fused to the N-terminus or C-terminus of the Fndc5 polypeptide, respectively. For example, in one embodiment the fusion protein is a Fndc5-GST and/or Fndc5-Fc fusion protein in which the Fndc5 sequences, respectively, are fused to the N-terminus of the GST or Fc sequences. Such fusion proteins can facilitate the purification, expression, and/or bioavailability of recombinant Fndc5. In another embodiment, the fusion protein is an Fndc5 protein containing a heterologous signal sequence at its C-terminus. In certain host cells (e.g., mammalian host cells), expression and/or secretion of Fndc5 can be increased through use of a heterologous signal sequence.

Preferably, an Fndc5 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An Fndc5-encoding nucleic acid can be cloned into such an expression vector such that the fusion moiety is linked in-frame to the Fndc5 protein.

The present invention also pertains to homologues of the Fndc5 proteins which function as either an Fndc5 agonist (mimetic) or an Fndc5 antagonist. In a preferred embodiment, the Fndc5 agonists and antagonists stimulate or inhibit, respectively, a subset of the biological activities of the naturally occurring form of the Fndc5 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Fndc5 protein.

Homologues of the Fndc5 protein can be generated by mutagenesis, e.g., discrete point mutation or truncation of the Fndc5 protein. As used herein, the term "homologue" refers to a variant form of the Fndc5 protein which acts as an agonist or antagonist of the activity of the Fndc5 protein. An agonist of the Fndc5 protein can retain substantially the same, or a subset, of the biological activities of the Fndc5 protein. An antagonist of the Fndc5 protein can inhibit one or more of the activities of the naturally occurring form of the Fndc5 protein, by, for example, competitively binding to a downstream or upstream member of the Fndc5 cascade which includes the Fndc5 protein. Thus, the mammalian Fndc5 protein and homologues thereof of the present invention can be, for example, either positive or negative regulators of adipocyte differentiation and/or thermogenesis in brown adipocytes.

In an alternative embodiment, homologues of the Fndc5 protein can be identified by screening combinatorial libraries of mutants, e.g., truncation mutants, of the Fndc5 protein for Fndc5 protein agonist or antagonist activity. In one embodiment, a variegated library of Fndc5 variants is generated by combinatorial mutagenesis at the nucleic acid level and is encoded by a variegated gene library. A variegated library of Fndc5 variants can be produced by, for example, enzymatically ligating a mixture of synthetic oligonucleotides into gene sequences such that a degenerate set of potential Fndc5 sequences is expressible as individual polypeptides, or alternatively, as a set of larger fusion proteins (e.g., for phage display) containing the set of Fndc5 sequences therein. There are a variety of methods which can be used to produce libraries of potential Fndc5 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Fndc5 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Fndc5 protein coding can be used to generate a variegated population of Fndc5 fragments for screening and subsequent selection of homologues of an Fndc5 protein. In one embodiment, a library of coding sequence fragments can be generated by treating a double stranded PCR fragment of an Fndc5 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Fndc5 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Fndc5 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Fndc5 homologues (Arkin and Youvan (1992) *Proc. Natl. Acad. Sci. USA* 89:7811-7815; Delagrave et al. (1993) *Protein Engineering* 6(3):327-331).

In another aspect, an isolated Fndc5 protein, or a fragment thereof, can be used as an immunogen to generate antibodies that bind Fndc5, or the complex thereof, using standard techniques for polyclonal and monoclonal antibody preparation. The full-length Fndc5 protein can be used or, alternatively, antigenic peptide fragments of Fndc5, or peptides in complex, can be used as immunogens. An Fndc5 immunogen typically is used to prepare antibodies by immunizing a suitable subject, (e.g., rabbit, goat, mouse or other mammal) with the immunogen. An appropriate immunogenic preparation can contain, for example, recombinantly expressed Fndc5 protein or a chemically synthesized Fndc5 peptide. The preparation can further include an adjuvant, such as Freund's complete or incomplete adjuvant, or similar immunostimulatory agent. Immunization of a suitable subject with an immunogenic Fndc5 preparation induces a polyclonal anti-Fndc5 antibody response.

Accordingly, another aspect of the invention pertains to the use of anti-Fndc5 antibodies. The term "antibody" as used herein refers to immunoglobulin molecules and immunologically active portions of immunoglobulin molecules, i.e., molecules that contain an antigen binding site which specifically binds (immunoreacts with) an antigen, such as Fndc5. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Fndc5. The term "monoclonal antibody" or "monoclonal antibody composition", as used herein, refers to a population of antibody molecules that contain only one species of an antigen binding site capable of immunoreacting with a particular epitope of Fndc5. A monoclonal antibody composition thus typically displays a single binding affinity for a particular Fndc5 protein with which it immunoreacts.

Polyclonal anti-Fndc5 antibodies can be prepared as described above by immunizing a suitable subject with an Fndc5 immunogen, or fragment thereof. The anti-Fndc5 antibody titer in the immunized subject can be monitored over time by standard techniques, such as with an enzyme linked immunosorbent assay (ELISA) using immobilized Fndc5. If desired, the antibody molecules directed against Fndc5 can be isolated from the mammal (e.g., from the blood) and further purified by well known techniques, such as protein A chromatography to obtain the IgG fraction. At an appropriate time after immunization, i.e., when the anti-Fndc5 antibody titers are highest, antibody-producing cells can be obtained from the subject and used to prepare monoclonal antibodies by standard techniques, such as the hybridoma technique originally described by Kohler and Milstein (1975) *Nature* 256: 495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an Fndc5 immunogen as described above, and the culture supernatants of the resulting hybridoma cells are screened to identify a hybridoma producing a monoclonal antibody that binds Fndc5.

Any of the many well-known protocols used for fusing lymphocytes and immortalized cell lines can be applied for the purpose of generating an anti-Fndc5 monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag-4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Fndc5, i.e., using a standard ELISA assay.

As an alternative to preparing monoclonal antibody-secreting hybridomas, a monoclonal anti-Fndc5 antibody can be identified and isolated by screening a recombinant combinatorial immunoglobulin library (e.g., an antibody phage display library) with Fndc5 to thereby isolate immunoglobulin library members that bind Fndc5. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-Fndc5 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-Fndc5 antibody (e.g., monoclonal antibody) can be used to isolate Fndc5 by standard techniques, such as affinity chromatography or immunoprecipitation. An anti-Fndc5 antibody can facilitate the purification of natural Fndc5 from cells and of recombinantly produced Fndc5 expressed in host cells. Moreover, an anti-Fndc5 antibody can be used to detect Fndc5 protein (e.g., in a cellular lysate or cell supernatant) in order to evaluate the abundance and pattern of expression of the Fndc5 protein. Anti-Fndc5 antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In vivo techniques for detection of Fndc5 protein include introducing into a subject a labeled antibody directed against the protein. For example, the antibody can be labeled with a radioactive marker whose presence and location in a subject can be detected by standard imaging techniques.

IV. Identification of Compounds that Modulate Fndc5

The Fndc5 nucleic acid and polypeptide molecules described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In one aspect, modulators, inhibitors, or antagonists against the polypeptides of the invention, biological complexes containing them, or orthologues thereof, may be used to treat any disease or other treatable condition of a patient (including humans and animals), including, for example, metabolic disorders.

Modulators of Fndc5 nucleic acid and polypeptide molecules, may be identified and developed as set forth below using techniques and methods known to those of skill in the art. The modulators of the invention may be employed, for instance, to inhibit and treat Fndc5-mediated diseases or disorders. The modulators of the invention may elicit a change in one or more of the following activities: (a) a change in the level and/or rate of formation of an Fndc5-receptor complex, (b) a change in the activity of an Fndc5 nucleic acid and/or polypeptide, (c) a change in the stability of an Fndc5 nucleic acid and/or polypeptide, (d) a change in the conformation of an Fndc5 nucleic acid and/or polypeptide, or (e) a change in the activity of at least one polypeptide contained in an Fndc5 complex. A number of methods for identifying a molecule which modulates an Fndc5 nucleic acid and/or polypeptide are known in the art. For example, in one such method, an Fndc5 nucleic acid and/or polypeptide, is contacted with a test compound, and the activity of the Fndc5 nucleic acid and/or polypeptide is determined in the presence of the test compound, wherein a change in the activity of the Fndc5 nucleic acid and/or polypeptide in the presence of the compound as compared to the activity in the absence of the compound (or in the presence of a control compound) indicates that the test compound modulates the activity of the Fndc5 nucleic acid and/or polypeptide.

Compounds to be tested for their ability to act as modulators of Fndc5 nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of an Fndc5 polypeptide (e.g., a dominant negative form that binds to, but does not activate, an Fndc5 receptor).

A variety of assay formats will suffice and, in light of the present disclosure, those not expressly described herein may nevertheless be comprehended by one of ordinary skill in the art based on the teachings herein. Assay formats for analyzing Fndc5-receptor complex formation and/or activity of an Fndc5 nucleic acid and/or polypeptide, may be generated in many different forms, and include assays based on cell-free systems, e.g. purified proteins or cell lysates, as well as cell-based assays which utilize intact cells. Simple binding assays can also be used to detect agents which modulate an Fndc5, for example, by enhancing the formation of an Fndc5, by enhancing the binding of an Fndc5 to a substrate, and/or by enhancing the binding of an Fndc5 polypeptide to a substrate. Another example of an assay useful for identifying a modulator of an Fndc5 is a competitive assay that combines one or more Fndc5 polypeptides with a potential modulator, such as, for example, polypeptides, nucleic acids, natural substrates or ligands, or substrate or ligand mimetics, under appropriate conditions for a competitive inhibition assay. Fndc5 polypeptides can be labeled, such as by radioactivity or a colorimetric compound, such that Fndc5-receptor complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting Fndc5es, or complex polypeptides, as described above.

Complex formation between an Fndc5 polypeptide, or fragment thereof, and a binding partner (e.g., Fndc5 receptor) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying Fndc5-receptor complexes described above may be incorporated into the detection methods.

In certain embodiments, it may be desirable to immobilize an Fndc5 polypeptide to facilitate separation of Fndc5 complexes from uncomplexed forms of one or both of the proteins, as well as to accommodate automation of the assay. Binding of an Fndc5 polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of Fndc5 polypeptides found in the bead fraction quantified from the gel using standard electrophoretic techniques such as described in the appended examples.

Other techniques for immobilizing proteins on matrices are also available for use in the subject assay. For instance, an Fndc5 polypeptide may be immobilized utilizing conjugation of biotin and streptavidin. For instance, biotinylated polypeptide molecules may be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the Fndc5 polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of Fndc5 polypeptide trapped in the Fndc5 complex may be assessed with a chromogenic substrate of the enzyme, e.g. 3,3'-diamino-benzadine tetrahydrochloride or 4-chloro-1-naphthol. Likewise, a fusion protein comprising the Fndc5 polypeptide and glutathione-S-transferase may be provided, and Fndc5 complex formation quantified by detecting the GST activity using 1-chloro-2,4-dinitrobenzene (Habig et al (1974) J Biol Chem 249:7130).

Antibodies against the Fndc5 polypeptide can be used for immunodetection purposes. Alternatively, the Fndc5 polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, an Fndc5 polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a DN217-420inding domain of a transcriptional activator may be fused in frame to the coding sequence for a "bait" protein, e.g., an Fndc5 polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a DN217-420inding domain that recognizes the responsive element on the reporter gene in the host cell, and (b) a bait protein (e.g., an Fndc5 polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DN217-420inding domain of the first hybrid protein and the transcriptional activation domain of the second hybrid protein may be derived from transcriptional activators having separable DN217-420inding and transcriptional activation domains. For instance, these separate DN217-420inding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DN217-420inding domains may be used in the subject constructs; such as domains of ACE1, λcI, lac repressor, jun or fos. In another embodiment, the DN217-420inding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the Fndc5, or complex polypeptide, of interest may be generated in whole cells, taking advantage of cell culture techniques to support the subject assay. For example, the Fndc5, or complex polypeptide, may be constituted in a prokaryotic or eukaryotic cell culture system. Advantages to generating the Fndc5, or complex polypeptide, in an intact cell includes the ability to screen for modulators of the level and/or activity of the Fndc5, or complex polypeptide, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The Fndc5 nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of Fndc5 may be detected in a cell-free assay generated by constitution of a functional Fndc5 in a cell lysate. In an alternate format, the assay can be derived as a reconstituted protein mixture which, as described below, offers a number of benefits over lysate-based assays.

The activity of an Fndc5 or an Fndc5 polypeptide may be identified and/or assayed using a variety of methods well known to the skilled artisan. For example, the activity of an Fndc5 nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of an Fndc5 nucleic acid and/or polypeptide may be assessed by monitoring changes in the phenotype of a targeted cell. For example, the detection means can include a reporter gene construct which includes a transcriptional regulatory element that is dependent in some form on the level and/or activity of an Fndc5 nucleic acid and/or polypeptide. The Fndc5 nucleic acid and/or polypeptide may be provided as a fusion protein with a domain that binds to a DNA element of a reporter gene construct. The added domain of the fusion protein can be one which, through its DN217-420inding ability, increases or decreases transcription of the reporter gene. Whichever the case may be, its presence in the fusion protein renders it responsive to an FNDC5 nucleic acid and/or polypeptide. Accordingly, the level of expression of the reporter gene will vary with the level of expression of an Fndc5 nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of an Fndc5 nucleic acid and/or polypeptide present in the cell. Such embodiments of the subject assay are particularly amenable to high through-put analysis in that proliferation of the cell can provide a simple measure of inhibition of the Fndc5 nucleic acid and/or polypeptide.

V. Methods of the Invention

The methods of the invention relate to the expression and/or activity of Fndc5 sufficient to modulate (e.g., induce or repress) brown fat cell differentiation, wherein increases in differentiated brown fat cells increase energy expenditure and can therefor be used to treat metabolic disorders such as obesity, cardiac hypertrophy, type II diabetes, and in need of more exercise; and, wherein decreases in differentiated brown fat cells decrease energy expenditure and can therefore be used to treat the effects of such conditions as cachexia, anorexia, and obesity-associated cancer.

The invention also relates to methods for increasing energy expenditure in a mammal comprising inducing expression and/or activity of Fndc5 sufficient to activate brown fat cell differentiation in the mammal, wherein the differentiated brown fat cells promote energy expenditure thereby increasing energy expenditure in the mammal.

The term "sufficient to activate" is intended to encompass any increase in expression and/or activity of Fndc5 that promotes, activates, stimulates, enhances, or results in brown fat induction.

In another aspect, the invention relates to methods for treating metabolic disorders in a subject comprising administering to the subject an agent that induces expression and/or activity of Fndc5, wherein expression and/or activity of Fndc5 increases respiration and energy expenditure to thereby treat the metabolic disorder. In one embodiment, total respiration is increased following the expression and/or activity of Fndc5. In another embodiment, uncoupled respiration is increased following the expression and/or activity of Fndc5. Uncoupled respiration dissipates heat and thereby increases energy expenditure in the subject.

As used herein, the term "agent" and "therapeutic agent" is defined broadly as anything that cells from a subject having a metabolic disorder may be exposed to in a therapeutic protocol. In one embodiment, the agent is a recombinant Fndc5 protein, or fragment thereof, or nucleic acid molecule encoding such a polypeptide. In another embodiment, the agent is an anti-sense nucleic acid molecule having a sequence complementary to Fndc5 (e.g., an RNAi, siRNA, or other RNA inhibiting nucleic acid molecule).

The term "administering" is intended to include routes of administration which allow the agent to perform its intended function of modulating (e.g., increasing or decreasing) expression and/or activity of Fndc5. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term "effective amount" of an agent that induces expression and/or activity of Fndc5 is that amount necessary or sufficient to modulate (e.g., increase or decrease) expression and/or activity of Fndc5 in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular respiration agent to treat a metabolic disorder can be monitored by comparing two or more samples obtained from a subject undergoing anti-obesity or obesity-related disorder treatment. In general, it is preferable to obtain a first sample from the subject prior to beginning therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

Another aspect of the invention relates to a method for inducing brown fat cell differentiation in a mammal comprising expressing Fndc5 nucleic acid and/or polypeptide molecules in a mammal and monitoring the differentiation of brown fat cells in the mammal. Increased brown adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by analyzing 1) the expression of cidea, adiponectin (adipoq), adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, and dio; 2) increases in cellular respiration (i.e., total and uncoupled respiration); 3) increases in thermogenesis of adipose cells; 4) increases in insulin sensitivity of adipose, muscle and/or hepatic cells; 5) decreases in hepatosteatosis, obesity, type II diabetes, and/or appetite; 6) increases in insulin secretion of pancreatic beta cells; 7) increases in cardiac function to combat cardiac hypertrophy; 8) improved muscle hypoplasia; 9) reduction in growth and effects of obesity-associated cancer, cachexia, and anorexia; and/or 10) treatment of diseases or disorders characterized by increased PGC-1 expression or activity, e.g., diabetes or obesity.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant Fndc5 polypeptides, and fragments thereof, can be administered to subjects. In some embodiments, fusion proteins can be constructed and administered which have enhanced biological properties (e.g., Fc fusion proteins discussed above). In addition, the Fndc5 polypeptides, and fragment thereof, can be modified according to well known pharmacological methods in the art (e.g., pegylation, glycosylation, oligomerization, etc.) in order to further enhance desirable biological activities, such as increased bioavailability and decreased proteolytic degradation.

VI. Pharmaceutical Compositions

In another aspect, the present invention provides pharmaceutically acceptable compositions which comprise a therapeutically-effective amount of an agent that modulates (e.g., increases or decreases) Fndc5 expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) Fndc5 expression and/or activity, or expression and/or activity of the complex, or composition comprising an agent that modulates (e.g., enhances) Fndc5 expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) Fndc5 expression and/or activity, or expression and/or activity of the complex encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) Fndc5 expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) Fndc5 expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) Fndc5 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) Fndc5 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) Fndc5 expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) Fndc5 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1

Materials and Methods for Examples 10

A. Materials

Antibodies against UCP-1, tubulin and Fndc5 were obtained from Abcam, Inc. Forskolin, insulin, dexamethasone, rosliglitazone, GW6471 and antibody against flag were obtained from Sigma Corp. Primers for all qPCR experiments are listed in Table 3 below. Recombinant Fndc5, Lrg1, 11-15, VEGFβ and TIMP4 were from obtained from ABNOVA, Inc. (Taiwan). Coomassie staining kit and Lipofectamine 2000 was from Invitrogen Corp. In addition, exemplary references to human and mouse nucleic acid, protein, and gene sequences for markers analyzed in the Examples are listed in Table 4 below. In some embodiments, a polypeptide of the present invention maintains the ability to promote one or more biological activities of a marker described herein and/or listed in Table 4. In other embodiments, a polypeptide of the present invention maintains the ability to promote one or more biological activities of such a marker directly or indirectly. In some embodiments where a biological activity of the marker is directly affected, the polypeptide of the present invention can do so at a transcriptional (e.g., transcriptional enhancer or regulator) or translational level.

TABLE 3

(Table 3 discloses the forward primers as SEQ ID NOS 17-34 and the reverse primers as SEQ ID NOS 35-52, respectively, in order of appearance)

| Gene | Forward primer | Reverse primer |
| --- | --- | --- |
| m18s | TCAAGAACGAAAGTCGGAGG | GGACATCTAAGGGCATCAC |
| mFndc5 1 UTR | ggactcttggaaaacaccactg | tccacacagatgatctcaccac |
| mFndc5 2 | atgaaggagatggggaggaa | gcggcagaagagagctataaca |
| mAp2 | ACA CCG AGA TTT CCT TCA AAC TG | CCA TCT AGG GTT ATG ATG CTC TTC A |
| mCidea | TGC TCT TCT GTA TCG CCC AGT | GCC GTG TTA AGG AAT CTG CTG |
| mPGC1a | CCC TGC CAT TGT TAA GAC C | TGC TGC TGT TCC TGT TTT C |
| mPRDM16 | CAG CAC GGT GAA GCC ATT C | GCG TGC ATC CGC TTG TG |
| mTBP | GAA GCT GCG GTA CAA TTC CAG | CCC CTT GTA CCC TTC ACC AAT |
| mUCP1 | ACT GCC ACA CCT CCA GTC ATT | CTT TGC CTC ACT CAG GAT TGG |
| MAdiponectin | GCA CTG GCA AGT TCT ACT GCA A | GTA GGT GAA GAG AAC GGC CTT GT |
| mVEGFb | tatctcccagagctgccatcta | agccagaagatgctcacttgac |
| mIl15 | gaggccaagaagagttctggat | tgcccaggtaagagcttcaa |
| mTIMP4 | gaccctgctgacactcaaaaac | ggaagagtcaaatggcgtgtag |
| mLrg1 | cctcaaggaatgcctgatactg | ttggagaattccaccgacag |
| hTIMP4 | caggtcctcagtgatggaaaag | gtgatttggcagccacagtt |
| hFndc5 | aagcacaaggactgactcaagc | catgtccttgatggctggat |
| hLrg1 | ctagaacacacgatgggctttc | tcagctggaaggaaggacaa |
| hIL-15 | tcagtgcagggcttcctaaa | tggggtgaacatcactttcc |

TABLE 4

| Gene Symbol | Gene Name | GenBank Gene Accession Number | GenBank Protein Accession Number | Gene ID |
| --- | --- | --- | --- | --- |
| adipsia | complement factor D | e.g., NM_013459.2 and NM_001928.2 | e.g., NP_038487.1 and NP_001919.2 | e.g., 11537 and 1675 |
| fatty acid transporter cd36 | fatty acid transporter/cd36 | e.g., NM_007643.3 and NM_000072.3 and NM_001001547.2 and NM_001001548.2 and NM_001127443.1 and NM_001127444.1 | e.g., NP_031669.2 and NP_000063.2 and NP_001001547.1 and NP_001001548.1 and NP_001120915.1 and NP_001120916.1 | e.g., 12491 and 948 |
| adiponectin | adiponectin | e.g., NM_009605.4 and NM_004797.2 | e.g., NP_0033735.3 and NP_004788.1 | e.g., 11450 and 9370 |
| UCP-1 | uncoupling protein 1 | e.g., NM_009463.3 and NM_021833.4 | e.g., NP_033489.1 and NP_068605.1 | e.g., 22227 and 7350 |
| cidea | cell death-inducing DFFA-like effector a | e.g., NM_007702.2 and NM_001279.3 and NM_198289.2 | e.g., NP_031728.1 and NP_001270.1 and NP_938031.1 | e.g., 12683 and 1149 |
| PGC1a | Peroxisome porliferative activated receptor, gamma, coactivator 1 alpha | e.g., NM_008904.2 and NM_013261.3 | e.g., NP_032930.1 and NP_037393.1 | e.g., 19017 and 10891 |
| Elovl3 | elongation of very long chain fatty acids (FEN1/Elo2, | e.g., NM_007703.2 and NM_152310.1 | e.g., NP_031729.1 and NP_689523.1 | e.g., 12686 and 83401 |

TABLE 4-continued

| Gene Symbol | Gene Name | GenBank Gene Accession Number | GenBank Protein Accession Number | Gene ID |
|---|---|---|---|---|
| | SUR4/Elo3, yeast)-like 3 | | | |
| C/EBPbeta | CCAAT/enhancer binding protein beta | e.g., NM_009883.3 and NM_005194.2 | e.g., NP_034013.1 and NP_005185.2 | e.g., 12608 and 1051 |
| Cox7a1 | cyotchrome c oxidase subunit VIIa polypeptide 1 | e.g., NM_009944.3 and NM_001864.2 | e.g., NP_034074.1 and NP_001855.1 | e.g., 12865 and 1346 |
| Otopetrin | Otopetrin 1 | e.g., NM_172709.3 and NM_177998.1 | e.g., NP_766297.2 and NP_819056.1 | e.g., 21906 and 133060 |
| Type II deiodinase | Deiodinase, iodothyronine, type II | e.g., NM_010050.2 and NM_000793.4 and NM_001007023.2 and NM_013989.3 | e.g., NP_034180.1 and NP_000784.2 and NP_001007024.1 and NP_054644.1 | e.g., 13371 and 1734 |
| cytochrome C | cytochrome c | e.g., NM_009989.2 and NM_018947.4 | e.g., NP_034119.1 and NP_061820.1 | e.g., 13067 and 54205 |
| cox4i1 | cytochrome c oxidase subunit IV isoform 1 | e.g., NM_009941.2 and NM_001861.2 | e.g., NP_034071.1 and NP_001852.1 | e.g., 12857 and 1327 |
| coxIII | mitochondrially encoded cytochrome c oxidase III | e.g., NC_005089.1 and ENST00000362079 | e.g., NP_904334.1 and ENSP00000354982 | e.g., 17705 and 4514 |
| cox5b | cytochrome c oxidase subunit Vb | e.g., NM_009942.2 and NM_001862.2 | e.g., NP_034072.2 and NP_001853.1 | e.g., 12859 and 1329 |
| cox8b | cytochrome c oxidase subunit 8B, mitochondrial precursor | e.g., NM_007751.3 | e.g., NP_031777.1 | e.g., 12869 and 404544 |
| glut4 | solute carrier family 2 (facilitated glucose transporter), member 4 | e.g., NM_009204.2 and NM_001042.2 | e.g., NP_033230.2 and NP_001033.1 | e.g., 20528 and 6517 |
| atpase b2 | ATPase, H+ transportying, lysosomal 56/58 kDa, V1 subunit B2 | e.g., NM_057213.2 and NM_001693.3 | e.g., NP_476561.1 and NP_001684.2 | e.g., 117596 and 526 |
| coxII | mitochondrially encoded cytochrome c oxidase II | e.g., NC_005089.1 and ENST00000361739 | e.g., NP_904331 and ENSP00000354876 | e.g., 17709 and 4513 |
| atp5o | ATP synthase, H+ transporting, mitochondrial F1 complex, O subunit | e.g., NM_138597.2 and NM_001697.2 | e.g., NP_613063.1 and NP_001688.1 | e.g., 28080 and 539 |
| ndufb5 | NADH dehydrogenase (ubiquinone) 1 beta subcomplex, 5, 16 kDa | e.g., NM_025316.2 and NM_002492.2 | e.g., NP_079592.2 and NP_002483.1 | e.g., 66046 and 4711 |
| Rarres2 | retinoic acid receptor responder (tazarotene induced) 2 | e.g., NM_027852.2 and NM_002889.3 | e.g., NP_082128.1 and NP_002880.1 | e.g., 71660 and 5919 |
| Car3 | carbonic anhydrase 3 | e.g., NM_007606.3 and NM_005181.3 | e.g., NP_031632.2 and NP_005172.1 | e.g., 12350 and 761 |
| Peg10 | paternally expressed 10 | e.g., NM_001040611.1 and NM_001040152.1 and NM_001172437.1 and NM_001172438.1 and NM_015068.3 | e.g., NP_001035701.1 and NP_001035242.1 and NP_001165908.1 and NP_001165909.1 and NP_055883.2 | e.g., 170676 and 23089 |
| Cidec | Cidec cell death-inducing DFFA-like effector c | e.g., NM_178373.3 and NM_022094.2 | e.g., NP_848460.1 and NP_071377.2 | e.g., 14311 and 63924 |
| Cd24a | CD24a antigen | e.g., NM_009846.2 and NM_013230.2 | e.g., NP_033976.1 and NP_037362.1 | e.g., 12484 and 100133941 |
| Nr1d2 | nuclear receptor subfamily 1, group D, member 2 | e.g., NM_011584.4 and NM_001145425.1 and NM_005126.4 | e.g., NP_035714.3 and NP_001138897.1 and NP_005117.3 | e.g., 353187 and 9975 |
| Ddx17 | DEAD (Asp-Glu-Ala-Asp) box polypeptide 17 | e.g., NM_001040187.1 and NM_001098504.1 and NM_001098505.1 and NM_006386.4 and NM_030881.3 | e.g., NP_001035277.1 and NP_001091974.1 and NP_001091975.1 and NP_006377.2 and NP_112020.1 | e.g., 67040 and 10521 |
| Ap1p2 | amyloid beta (A4) precursor-like protein 2 | e.g., NM_001102455.1 and NM_001142276.1 and NM_001142277.1 and NM_001142278.1 and NM_001642.2 | e.g., NP_001095925.1 and NP_001135748.1 and NP_001135749.1 and NP_001135750.1 and NP_001633.1 | e.g., 11804 and 334 |
| Nr3c1 | nuclear receptor subfamily 3, group C, member 1 | e.g., NM_008173.3 and NM_000176.2 and NM_001018074.1 and | e.g., NP_032199.3 and NP_000167.1 and NP_001018084.1 | e.g., 14815 and 2908 |

TABLE 4-continued

| Gene Symbol | Gene Name | GenBank Gene Accession Number | GenBank Protein Accession Number | Gene ID |
|---|---|---|---|---|
| | | NM_001018075.1 and NM_001018076.1 and NM_001018077.1 and NM_001020825.1 and NM_001024094.1 | and NP_001018085.1 and NP_001018086.1 and NP_001018087.1 and NP_001018661.1 and NP_001019265.1 | |
| Rybp | RING1 and YY1 binding protein | e.g., NM_019743.3 and NM_012234.4 | e.g., NP_062717.2 and NP_036366.3 | e.g., 56353 and 23429 |
| Txnip | thioredoxin interacting protein | e.g., NM_001009935.2 and NM_006472.3 | e.g., NP_001009935.1 and NP_006463.3 | e.g., 56338 and 10628 |
| Cig30 | Elongation of very long chain fatty acids-like 3 | e.g., NM_152310.1 and NM_007703.1[1] | e.g., NP_689523.1 and NP_031729.1[1] | e.g., 83401 and 12686 |
| Ppar gamma 2 | Peroxisome proliferator-activated receptor gamma 2 | e.g., NM_015869.4 and NM_011146.2[1] | e.g., NP_056953 and NP_035276.1[1] | e.g., 5468 and 19016 |
| Prdm16 | PR domain containing 16 protein | e.g., NM_022114.3 and NM_199454.2 and NM_027504.3 | e.g., NP_071397.3 and NP_955533.2 and NP_081780.3 | e.g., 63976 and 70673 |
| Ap2 | Fatty acid binding protein 4 | e.g., NM_001442.2 and NM_024406.1 | e.g., NP_001433.1 and NP_077717.1 | e.g., 2167 and 11770 |
| Ndufs2 | NADH dehydrogenase (ubiquinone) Fe—S protein 2, 49 kDa (NADH-coenzyme Q reductase | e.g., NM_001166159.1 and NM_004550.4 and NM_153064.4 | e.g., NP_001159631.1 and NP_004541.1 and NP_694704.1 | e.g., 4720 and 226646 |
| Grp109A | Hydroxycarboxylic acid receptor 2 | e.g., NM_177551 and NM_030701.3 | e.g., NP_808219 and NP_109626.1 | e.g., 338442 and 80885 |
| AcylCoA-thioesterase 4 | Acyl-coenzyme A thioesterase 4 | e.g., NM_152331 and NM_134247.3 | e.g., NP_689544 and NP_599008.3 | e.g., 122970 and 171282 |
| Claudin1 | Claudin1 | e.g., NM_021101.4 and NM_016674.4 | e.g., NP_066924.1 and NP_057883.1 | e.g., 9076 and 12737 |
| PEPCK | Phosphoenolpyruvate carboxykinase (mitochondrial) | e.g., NM_001018073.1 and NM_004563.2 and NM_028994.2 | e.g., NP_001018083.1 and NP_004554.2 and NP_083270.1 | e.g., 5106 and 74551 |
| Fgf21 | Fibroblast growth factor 21 | e.g., NM_019113 and NM_020013.4 | e.g., NP_061986 and NP_064397.1 | e.g., 26291 and 56636 |
| AcyCoA-thioesterase 3 | Acyl-coenzyme A thioesterase 4 | e.g., NM_001037161.1 and NM_134246.3 | e.g., NP_001032238.1 and NP_599007.1 | e.g., 641371 and 171281 |
| Dio2 | Type II iodothyronine deiodinase | e.g., NM_00793.5 and NM_010050.2 | e.g., NP_000784.2 and NP_034180.1 | e.g., 1734 and 13371 |

B. Bioinformatic Identification of PGC1α-Dependent Signal-Peptide Proteins

All PGC1α-induced genes, as judged from gene expression analysis in MCK-PGC1α muscle with a fold change of at least 2 and $p<0.05$, were subjected to the following analysis. The protein sequence of the longest transcript were analyzed in the SignalP-software (Emanuelsson et al. (2007) *Nat. Protoc.* 2, 953-971; available on the world wide web at cbs.dtu.dk/services/SignalP/). Sequences with positive S, C, Y and D-score were considered positive for a signal sequence. All positive proteins were then screened for mitochondrial target sequences using the TargetP software suite (available on the world wide web at cbs.dtu.dk/services/TargetP/), whereas positive sequences were removed. All remaining hit proteins were then analyzed using qPCR in muscle from MCK-PGC1α mice and myocytes over expressing PGC1α.

C. Primary Cell Cultures and Recombinant Protein Treatment

The SVF from inguinal fat depots of 8-12 week old BALB/C mice were prepared and differentiated for 6 days as described in Kajimura et al. (2009) *Nature* 460, 1154-1158. Rosiglitazone was used at the two first days of differentiation. For all experiments, unless otherwise indicated, recombinant Fndc5 was added to the culture media at a concentration of 1 μg/ml the last 4 days of differentiation. Primary myoblasts were cultured and differentiated as described in Rasbach et al. (2010) *Proc. Natl. Acad. Sci. USA* 107, 21866-21871.

D. Preparation of Protein Fractions from Cells and Media

293HEK or primary myocytes were transfected with standard protocol or transduced with adenovirus at a MOI of 20 as indicated. 24 hours after transfection, media was removed, and cells were washed in large volumes of PBS five times, followed by incubation in Freestyle serum-free media (GIBCO) for 24 hours. The cells and media were then collected separately, and media centrifuged ×3 at 3000 rpm to pellet debris. Thereafter, ¼ volume of ice-cold TCA was added and precipitated protein was pelleted at 14000 rpm and washed three times in acetone. The pellet was then dried and resuspended in SDS-containing lysis buffer. Protein concentration was measured in both cell and media fraction and adjusted either by protein or volume as indicated.

E. RT-PCR

QPCR was carried out after Trizol-based RNA extraction using RNAeasy (Invitrogen) and thereafter SYBR green. All data was normalized to TBP, 18S or indicted in-house gene and quantitative measures obtained using the delta-delta-CT method.

F. Western Blot and Quantification

Protein amounts from all samples were assessed using the BCA-kit (Thermo Scientific) followed by protein concentration normalization prior to all western blot experiments. Western blot was carried out following standard procedure and final band intensity (QL-BG) was quantified using BioPix iQ (Bostrom et al. (2010) *Diabetes* 59, 1870-1878). All data was normalized to background and loading controls.

G. Additional Methods

Figure 14:
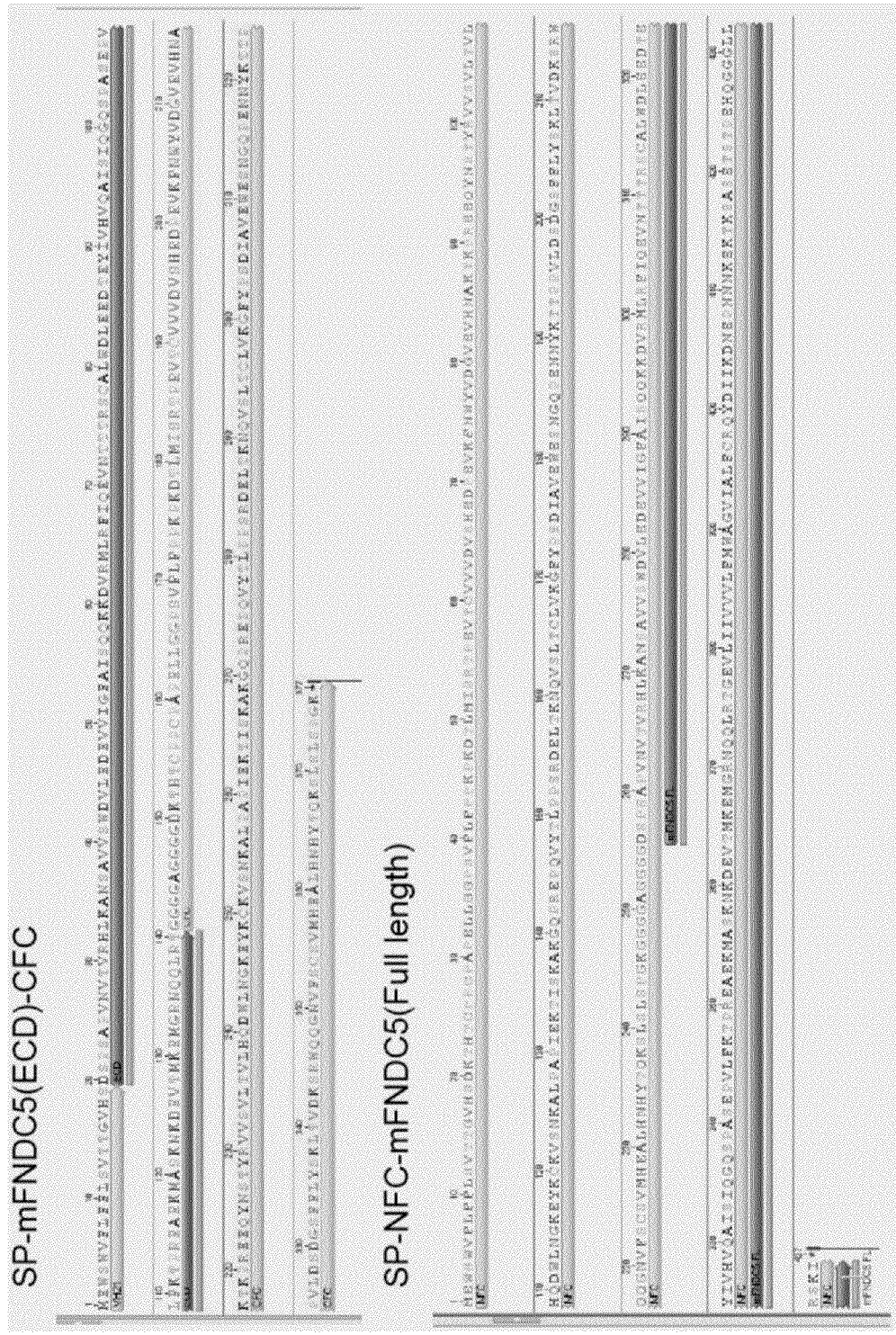
FIG. 14 shows representative sequences of FNDC5-Fc fusion constructs. mFNDC5(ECD) corresponds to amino acids 29-149 of SEQ ID NO: 2 and mFNDC5 (Full length) correspond to amino acids 29-209 of SEQ ID NO: 2.

CLARK electrode measurements, energy expenditure in vivo, IGTT and immunohistochemistry against UCP-1 were performed as described in Seale et al. (2011) *J. Clin. Invest.* 121, 96-105. FC-fusion construction and protein purification was performed by LakePharma (Ca) and representative sequences are shown in FIG. 14.

H. Mass Spectrometry and Peptide Fingerprinting of Purified, Secreted Fndc5

Gel bands were digested with sequencing grade trypsin (Promega) or ASP-N (Sigma-Aldrich) as per manufactures' instructions. Extracted in-gel protein digests were resuspended in 8 μL 5% formic acid/5% acetonitrile, and 4 μL were analyzed by microcapillary liquid chromatography electrospray ionization tandem mass spectrometry (LC-MS/MS). Analyses were done on a LTQ Orbitrap Velos mass spectrometer (Thermo Fisher Scientific, Germany) equipped with a Thermo Fisher Scientific nanospray source, an Agilent 1100 Series binary HPLC pump, and a Famos autosampler. Peptides were separated on a 100 μm×16 cm fused silica microcapillary column with an in-house made needle tip. The column was packed with MagicC18AQ $C_{18}$ reversed-phase resin (particle size, 5 μm; pore size, 200 Å; Michrom Bioresources). Separation was achieved through applying a 30 min gradient from 0 to 28% acetonitrile in 0.125% formic acid. The mass spectrometer was operated in a data dependent mode essentially as described previously in Villen and Gygi (2008) *Nat. Protoc.* 3, 1630-1638 with a full MS scan acquired with the Orbitrap, followed by up to 10 LTQ MS/MS spectra on the most abundant ions detected in the MS scan. Mass spectrometer settings were: full MS (AGC, $1\times10^6$; resolution, $6\times10^4$; m/z range, 375-1500; maximum ion time, 1000 ms); MS/MS (AGC, $5\times10^3$; maximum ion time, 120 ms; minimum signal threshold, $4\times10^3$; isolation width, 2 Da; dynamic exclusion time setting, 30 sec). Following mass spectrometry data acquisition, RAW files were converted into mzXML format and processed using a suite of software tools developed in-house for analysis. All precursors selected for MS/MS fragmentation were confirmed using algorithms to detect and correct errors in monoisotopic peak assignment and refine precursor ion mass measurements. All MS/MS spectra were then exported as individual DTA files and searched with no enzyme using the Sequest algorithm. These spectra were then searched against a database containing sequence of mouse Fndc5 in both forward and reversed orientations. The following parameters were selected to identify Fndc5: 10 ppm precursor mass tolerance, 0.8 Da product ion mass tolerance, fully tryptic or ASP-N digestion, and up to two missed cleavages. Variable modifications were set for methionine (+15.994915). In addition, a fixed modification for the carbamidomethylation for cysteine (+57.021464) was used as well. C-terminal fragment for Fndc5 was identified (KDEVTMKE) (SEQ ID NO: 53) by trypsin digestion and reconfirmed by a separate ASP-N digestion.

I. Preparation of Plasma Samples for Western Blot Analyses

Thirty-five μl of mouse or human plasma was precleared for albumin/IgG using the ProteoExtract-kit (CalBiochem) as recommended by the manufacturer. Samples were then concentrated to approximately 100 μl and >8 μg/μl, followed by deglycosylation of 150 μg using PNGase F (New England Biolabs). Eighty μl in total were then prepared containing 1× sample buffer with reducing agent and 1.7 μg/μl protein, sonicated, boiled and analyzed using Western blot analyses against Fndc5 or indicated antibody.

J. Construction of the C- and N-Terminal Flag Fusion Proteins (CTF and NTF) Containing Adenoviral Constructs The Fndc5 expression vector was purchased with a C-terminal FLAG-tag from OriGene, Inc. The QuickChange Multi Site XL™ Directed Mutagenesis Kit (Aligent Technologies) was used to introduce a FLAG tag downstream of the signal sequence and to mutate the c-terminal flag tag, thus resulting in the NTF-Fndc5 construct. The NTF and CTF Fndc5 constructs were then subcloned into the pENTR1a vector (Invitrogen Corp.) and recombined into the pAd-CMV-DEST-V5 vector (Invitrogen Corp.) and adenovirus was produced using the virapower system (Invitrogen Corp.), including three rounds of amplification. Thereafter, virus was concentrated using the Vivapure adenopack 100 (Sartorius Stedim Biotech) and buffer exchanges to saline reaching a concentration of 9-10 ifu/μl. A GFP-containing adenovirus previously used was prepared in parallel.

K. Transgenic Mice

The MCK-PGC1α transgenic and muscle-specific PGC1α knockout mice have been described previously in Handschin et al. (2007) *J. Biol. Chem.* 282, 30014-30021.

L. Exercise Protocols

Twelve week old B6 mice were either exercised using swimming as described in Bostrom et al. (2010) *Cell* 143, 1072-1083, or using free wheel running as described in Chinsomboon et al. (2009) *Proc. Natl. Acad. Sci. USA* 106, 21401-21406.

Example 2

Figure 2:
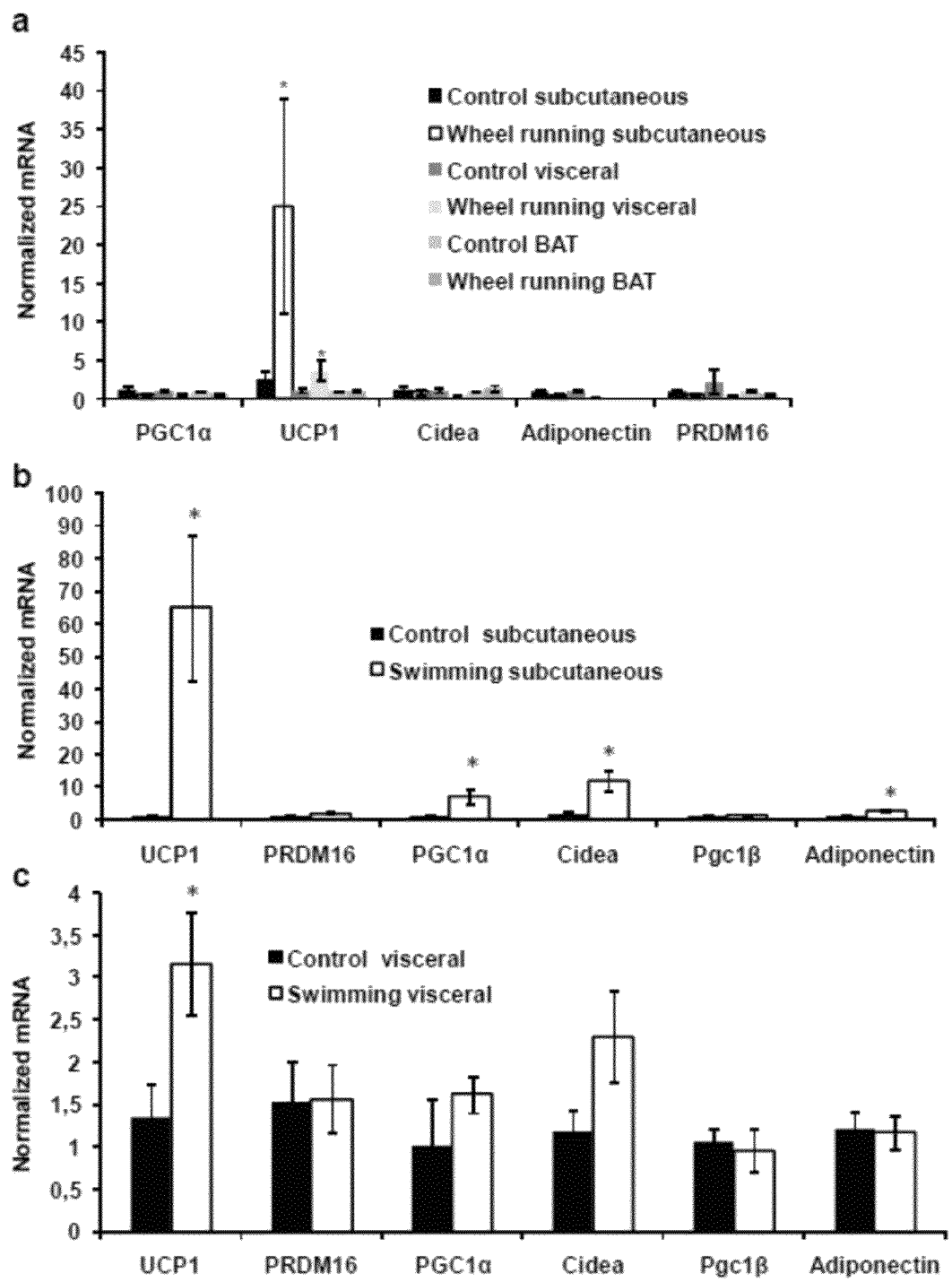
FIGS. 2A-2C show brown fat gene expression after exercise.

Transgenic PGC1α in Skeletal Muscle Induces Browning of Subcutaneous Adipose Tissue Mice with enhanced PGC1α in muscle are resistant to age-related obesity and diabetes (Wenz et al. (2009) *Proc. Natl. Acad. Sci. USA* 106, 20405-20410), suggesting that these animals have a fundamental alteration in systemic energy balance. Accordingly, adipose tissue of PGC1α transgenic mice was analyzed for expression of genes related to a thermogenic gene program and genes characteristic of brown fat development. No detectable alterations of the expression of brown fat-selective genes, such as UCP1, Cidea and PRDM16 in the interscapular brown adipose tissue or in the visceral (epidydimal) white adipose tissue were identified (FIG. 1A). However, the subcutaneous fat layer (inguinal), a white adipose tissue which is particularly prone to "browning," had significantly increased levels of UCP1 and Cidea mRNAs (FIG. 1B). Increased UCP1 protein levels and UCP1-positive multilocular cells using immunohistochemistry were also observed in the transgenic mice compared to controls (FIGS. 1C-1D). There are recent reports that exercise causes a mild increase in the expression of a thermogenic gene program in the visceral adipose depot, a depot that has minimal expression of these genes (Xu et al. (2011) *Am. J. Physiol. Regul. Integr. Comp. Physiol.* 300, R1115-1125). Since it is the subcutaneous white adipose depot that has the greatest tendency to turn on a powerful brown/thermogenic gene program and alter the systemic energy balance of mice (Seale et al. (2011) *J. Clin. Invest.* 121, 96-105), browning of the white adipose tissues was analyzed within the context of two types of exercise. Similar to what has been reported, a 2-fold increase in UCP1 mRNA expression was observed in the visceral, epididymal fat with three weeks of wheel running (FIG. 2). However, a much larger change (approximately 25-fold) was seen in the same mice in the subcutaneous inguinal fat depot. No change was observed in UCP1 expression in the classical interscapular brown fat under these conditions. Similarly, a small increase in UCP1 mRNA expression was seen with repeated bouts of swimming in warm (32° C.) water (FIG. 2). However, a large increase (65-fold) was observed in the inguinal white depot upon swimming. Thus, muscle-specific expression of PGC1α drives browning of subcutaneous white adipose tissue, possibly recapitulating part of the exercise program.

Example 3

Conditioned Media from PGC1α-Expressing Myocytes Induce Browning of Adipocytes in Culture The effect on browning of the adipose tissues from PGC1α-expressing muscle could be due to either direct muscle-fat signaling or to a more complicated signaling system. Treatment of primary adipocytes derived from the subcutaneous inguinal depot with serum-free, conditioned media from PGC1α-expressing myocytes increased the expression of several brown fat genes, such as UCP1, Cidea and PRDM16 (FIG. 1E). This suggested secretion of molecule(s) from these muscle cells that can affect a thermogenic gene program in the fat cells.

Example 4

Prediction of Several Candidate Secreted Proteins Controlled by PGC1α

Figure 3:
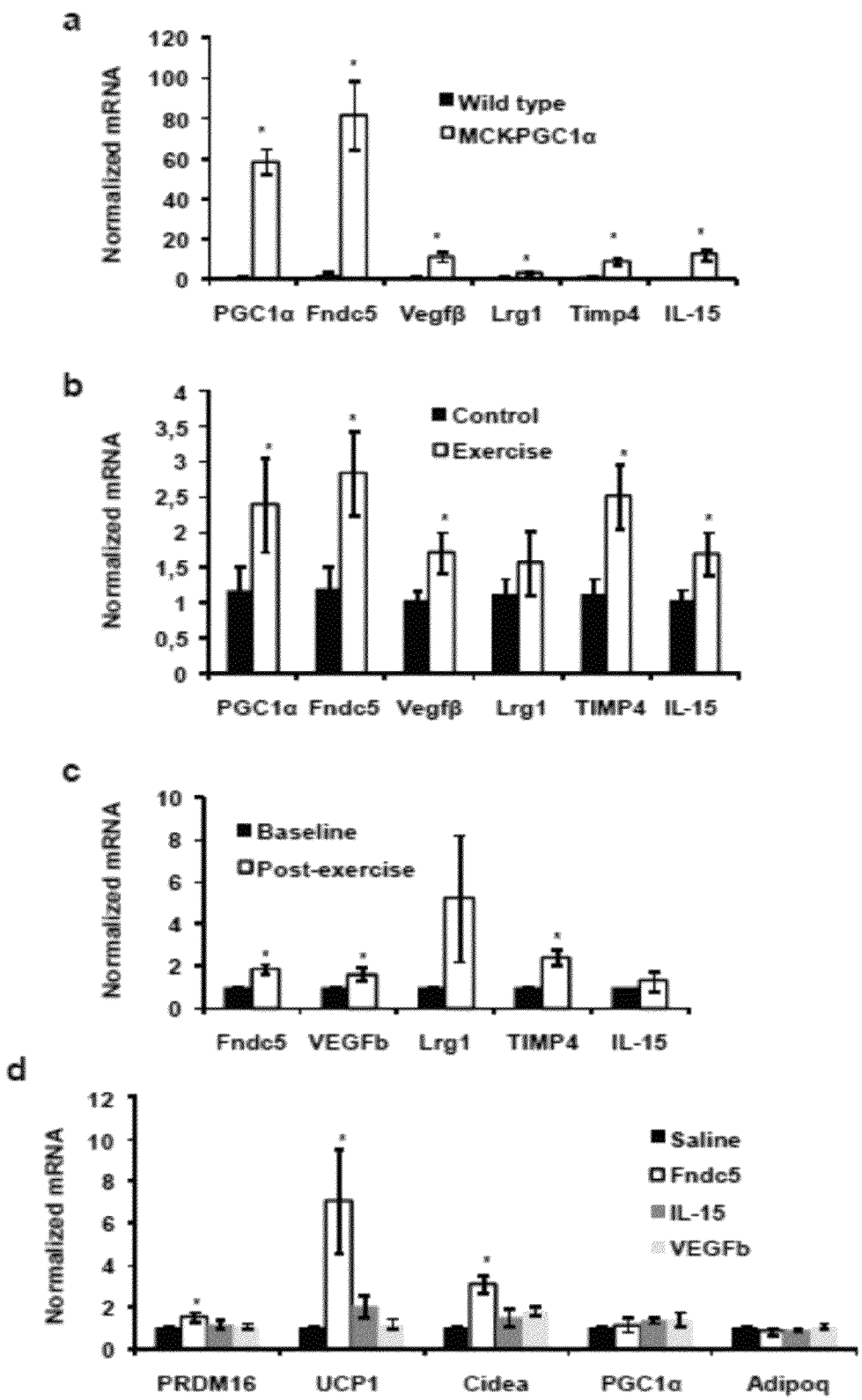
FIGS. 3A-3D show that Fndc5, VEGFβ, IL-15 and TIMP4 are induced with PGC1α over expression or exercise, and that Fndc5 induces brown fat gene expression.
Figure 4:
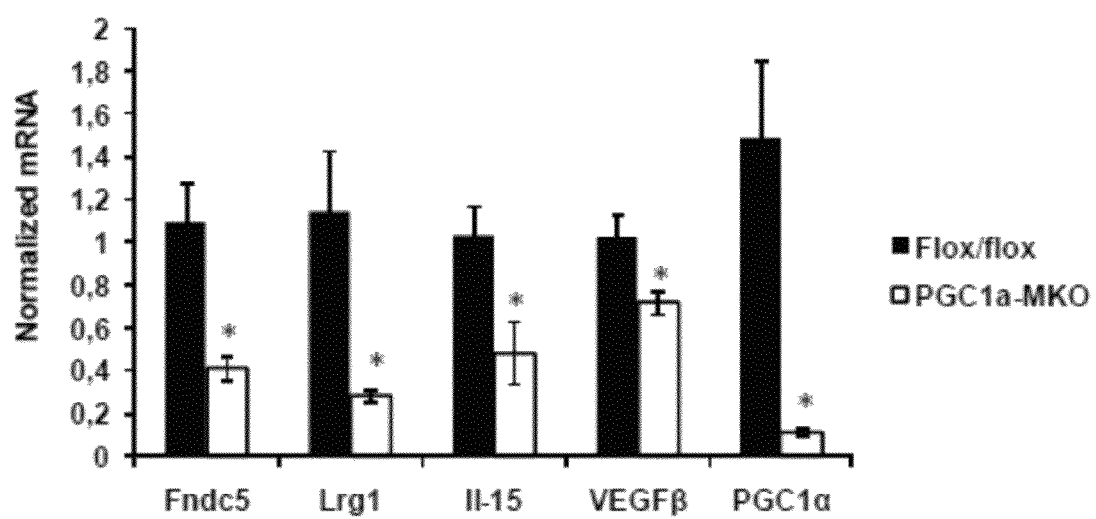
FIG. 4 shows the results of qPCR analyses of the indicated genes from PGC1α muscle-specific knockout mice or respective flow/flow controls. Each group had n=5 mice. * p<0.05 compared to control using students T-TEST.

A combination of Affymetrix-based gene expression arrays and an algorithm that predicts protein secretion was then used to search for proteins that could mediate the browning of adipose tissues under the control of muscle PGC1α. Proteins with mitochondrial targeting sequences were excluded, and all candidate proteins were validated in gain-of-function systems for PGC1α both in vitro and in vivo. Five proteins were identified as PGC1α target genes and likely to be secreted: IL-15, Fndc5, VEGFβ, Lrg1 and TIMP4 (FIG. 3A). Expression of these genes were reduced in mice with muscle-specific deletion of the PGC1α gene (FIG. 4). Furthermore, these genes were also found to be increased at the RNA level these in muscle from exercised mice (FIG. 3B). The expression of these genes was also examined in muscle biopsies from human subjects before and after a controlled period of endurance exercise (Vind et al. (2011) *Diabetologia* 54, 157-167; FIG. 3C). Fndc5, VEGFβ and TIMP4 were all significantly induced at the mRNA level in humans with exercise. IL-15 has previously been reported as being secreted from muscle under the influence of exercise (Nielsen and Pedersen (2007) *Appl. Physiol. Nutr. Metab.* 32, 833-839), while the regulation of Fndc5, VEGFβ, Lrg-1 and TIMP4 by exercise has not been described.

Example 5

Fndc5 Robustly Induces a Brown Fat Gene Program in Cultured White Adipose Cells

Figure 6:
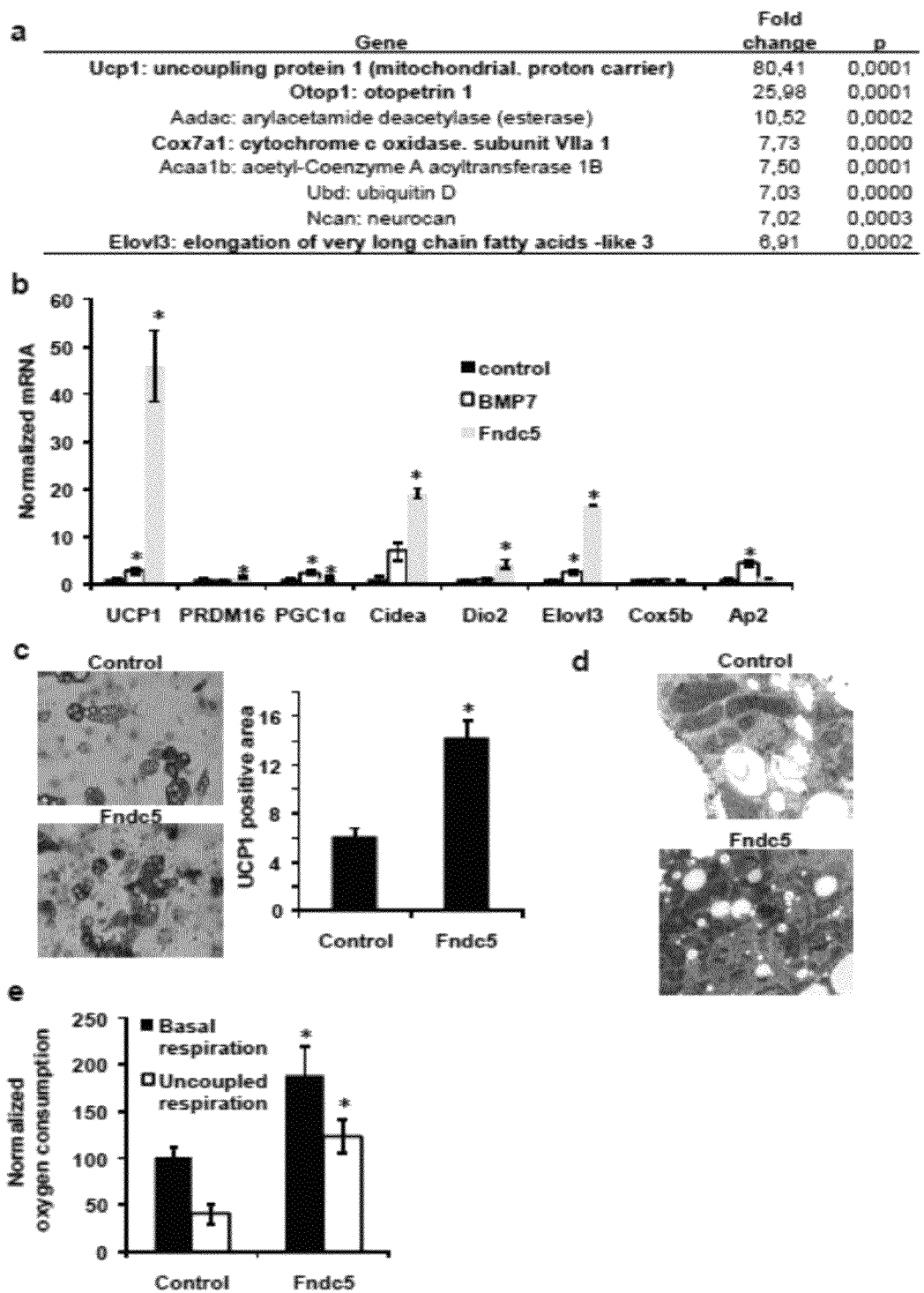
FIGS. 6A-6E show that Fndc5 is a potent inducer of the brown fat program.

Several commercially available versions of these proteins were applied directly to primary subcutaneous white adipocytes during differentiation. Most of these factors, such as IL-15, or VEGFβ, had no or minimal effects on the expression of UCP1 or the other brown fat genes at a concentration of 200 nM or higher. Fndc5 promoted a 10-fold induction of UCP1 (FIG. 3D) at a concentration of 20 nM. The transcriptional changes in cells treated with Fndc5 were addressed on a global scale using gene expression arrays (FIG. 5). UCP1 and three other known brown fat genes, including Elovl3, Cox7a and Otop1, were found among the top 8 up-regulated genes (FIG. 6A). Conversely, many genes characteristic of white fat development were down regulated, such as leptin (FIG. 5). These data show that the activation of browning and thermogenic genes by Fndc5 is a major part of the action of this polypeptide on these cells.

The effects of Fndc5 treatment were remarkably robust, as UCP1 mRNA was increased 10-500-fold by doses of 1-50 nM (FIG. 6B). In contrast, BMP-7, reported as a potent inducer of browning (Tseng et al. (2008) *Nature* 454, 1000-1004), had a much smaller effect (maximal of 2-fold) on the same cells at similar doses. This effect of BMP-7 is minimal if the overall increase in adipose differentiation and adipose gene expression is taken into account (compared relative to aP2 expression).

Immunohistochemistry analyese were also conducted to study cells treated with Fndc5 and a robust increase in UCP-1 positive adipocytes with multilocular lipid droplets was observed (FIG. 6C). Electron microscopic analysis showed numerous small lipid droplets and a high density of mitochondria compared to control cells, consistent with a brown fat-like phenotype. The sizes of mitochondria, however, were similar between groups (FIG. 6D). Lastly, measurements of oxygen consumption with a Clark electrode provided functional evidence of increased energy expenditure with Fndc5 exposure. Total oxygen consumption was increased by 100% by 20 nM of Fndc5 and the majority was uncoupled respiration (FIG. 6E). Thus, Fndc5 potently induces thermogenesis and a brown fat-like gene program in cultured adipocytes.

Figure 7:
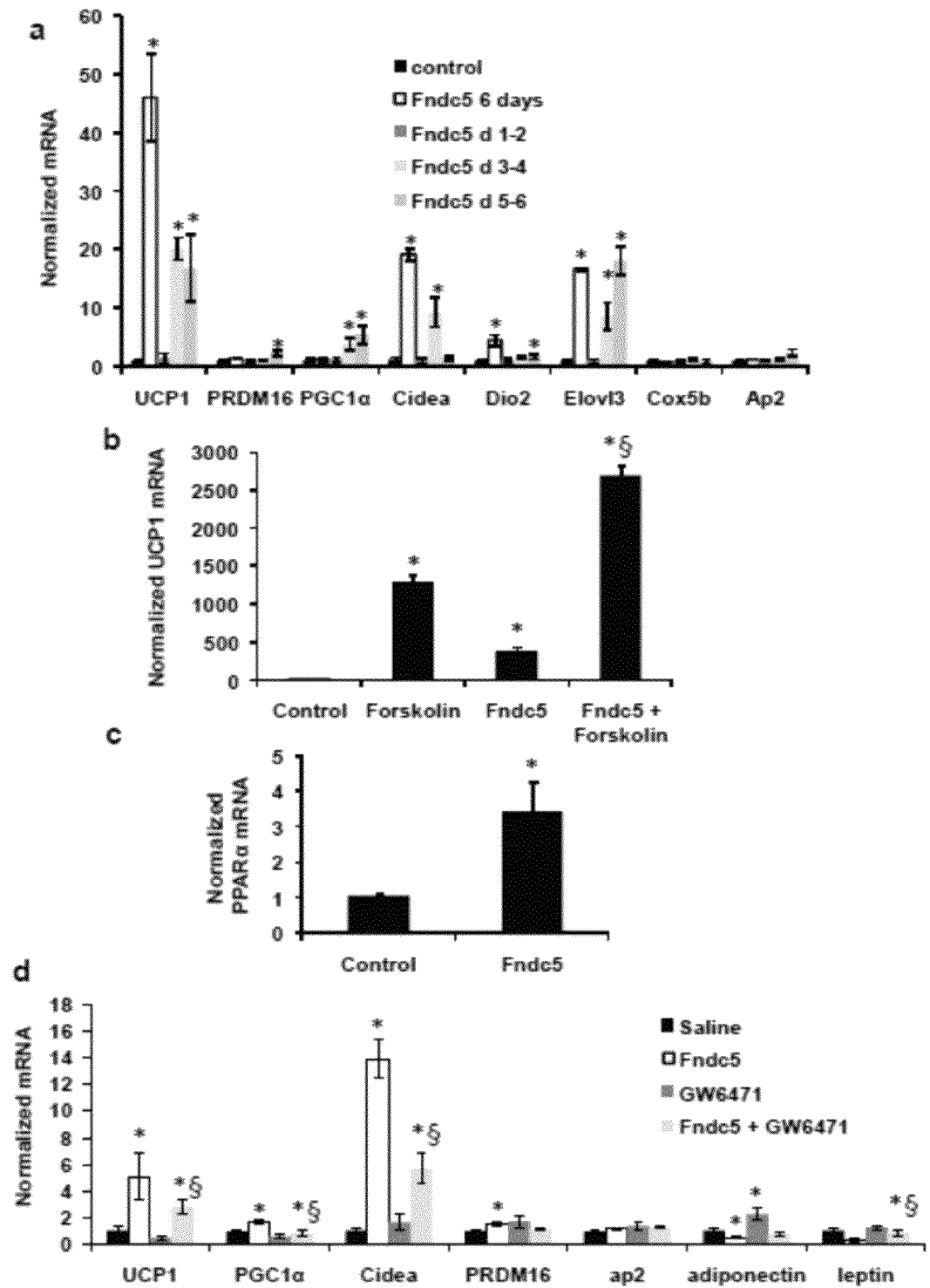
FIGS. 7A-7D show that Fndc5 acts on brown fat development during adipocytes differentiation, in a PPARα-dependent manner.

Next, the time frame in the differentiation process when Fndc5 was effective in activating the expression of UCP1 and other thermogenic genes was determined. Fndc5 was applied to cells in 2 day windows from day 0-6, and this was compared to cells where the protein was added during the entire 6 day differentiation process. As shown in FIG. 7A, treatment during days 3-4 and 5-6 are effective at inducing UCP1 mRNA, though not as effectively as if the Fndc5 was present throughout the differentiation process. Furthermore, treatment during the initial two days had no effect on UCP1 levels. Norepinephrine release from sympathetic nerve terminals is an important influence on thermogenic gene expression on both classical brown fat the brown-like program in white fat cells. Accordingly, it was asked whether Fndc5 effects were additive or redundant with cAMP signaling. As shown in FIG. 7B, Fndc5-exposed cells increase UCP1 expression in an additive way when exposed to forskolin, an adenyl cyclase activator.

Example 6

PPARα Acts Downstream of Fndc5 to Promote a Thermogenic/Brown Fat Program

A key question is how Fndc5 is able to stimulate a thermogenic gene program. One potentially important transcription factor induced by Fndc5, identified using gene expression arrays, was PPARα. This transcription factor has been shown to drive UCP1 expression and other genes involved in browning (Komatsu et al. (2010) *Genes Cells* 15, 91-100). PPARα is increased 3.5-fold at the RNA level by Fndc5 treatment (FIG. 7C). Importantly, the Fndc5-mediated increase in UCP-1 was significantly reduced when cells was subjected to the selective PPARα antagonist GW6471 (FIG. 7D). By contrast, the PPARα antagonist normalized the reduction seen in white adipose genes leptin and adiponectin after Fndc5-treatment. Together, these data indicate that Fndc5 acts, in part, via activation of expression PPARα.

Example 7

Figure 8:
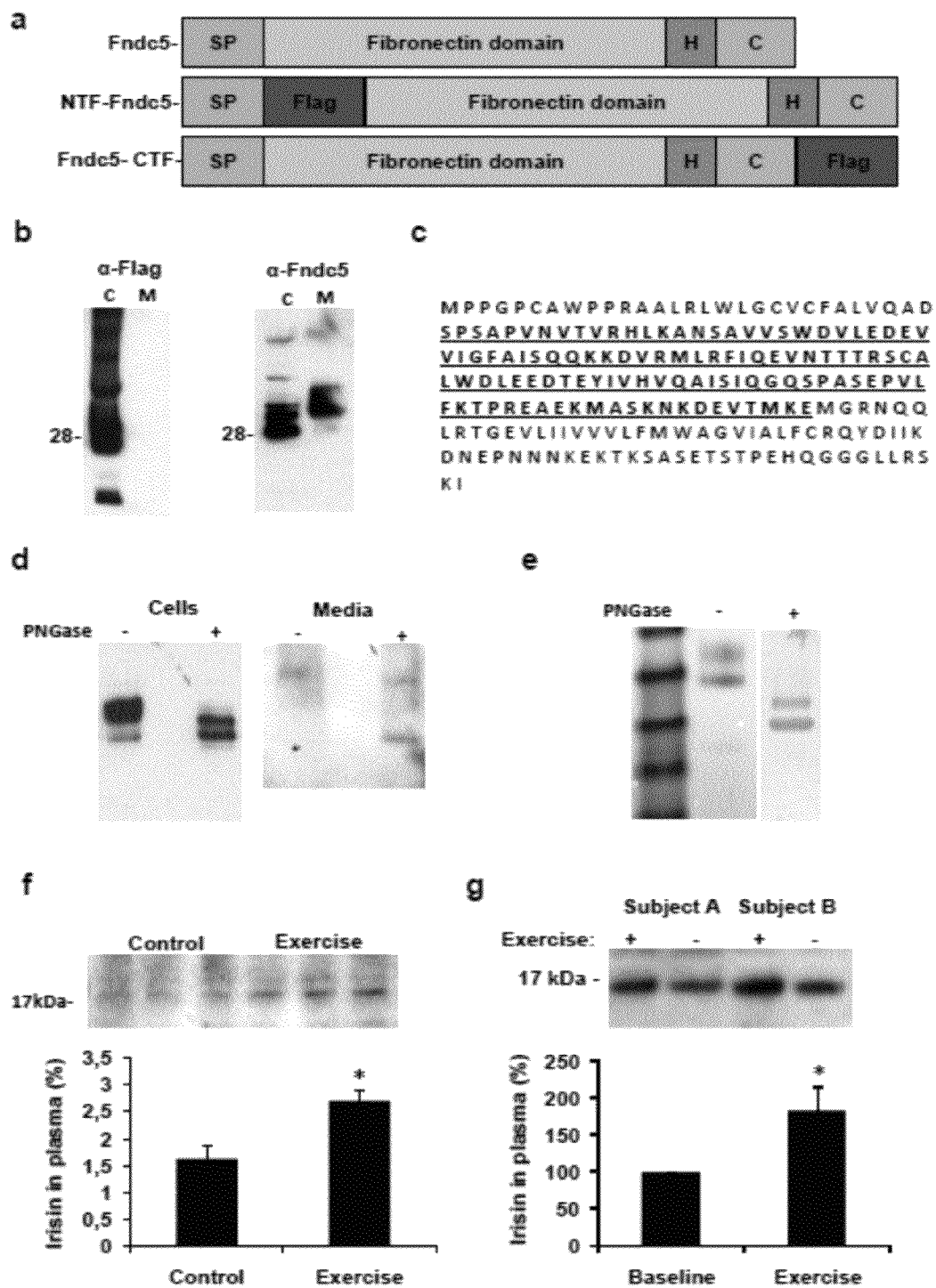
FIGS. 8A-8G show that Fndc5 is proteolytically cleaved and secreted from muscle cells.

Irisin is a Cleaved and Secreted Fragment of Fndc5, Found in Mouse and Human Plasma Fndc5/Frcp2, also known as PeP, was previously shown to have a signal peptide, two fibronectin domains and one hydrophobic domain likely to be membrane-inserted (Teufel et al. (2002) Gene 297, 79-83; FIG. 8A). These studies did not investigate whether part of this protein might be secreted (Teufel et al. (2002) Gene 297, 79-83; Ferrer-Martinez et al. (2002) Dev. Dyn. 224, 154-167). Considering this structure, it was hypothesized that Fndc5 might be synthesized as a type I membrane protein, followed by proteolytic cleavage, releasing the N-terminal part of the protein into the extracellular space. Thus, any C- or N-terminal tags would be lost during processing of the mature protein or interfere with the appropriate processing. Indeed, expression of a C-terminally FLAG-tagged Fndc5 (FIG. 8A), did not result in any FLAG-immunoreactivity in the medium from cells expressing this construct (FIG. 8B). However, when the same samples were immunoblotted with an antibody that recognizes the endogenous Fndc5 protein, substantial amounts of Fndc5 were detected in the media (FIG. 8B). This indicates that Fndc5 is C-terminally cleaved and secreted.

Mass spectrometry (MS) was used to determine the sequence of the Fndc5-derived polypeptide found in the media. To do this, the N-terminus of full-length Fndc5 (without the signal peptide) was fused to the C-terminus of the Fc-domain of IgG. After purification of the secreted material, MS analyses indicated that Fndc5 was truncated as shown in FIG. 8C. This secreted portion of Fndc5 has remarkable conservation between species, with 100% identity between mice and humans (FIG. 9).

Western blot analyses of media fractions with antibodies against wild-type Fndc5 showed multiple bands, suggestive of glycosylation. Treatment of cell supernatants from Fndc5-expressing cells with Peptide N-Glycosidase F (PNGase F) resulted in a significant size decrease by SDS-gel electrophoresis (FIG. 8D). A similar shift was also seen with a purified, Fc-tagged Fndc5 (FIG. 8D), demonstrating that the secreted version of Fndc5 is glycosylated. Thus, a substantial proportion of the FNDC5 gene product is proteolytically cleaved, glycosylated and secreted. Since this distinct polypeptide has not been previously described and it signals from muscle to other tissues, the novel polypeptide was named Irisin, after Iris, the Greek messenger goddess.

Figure 10:
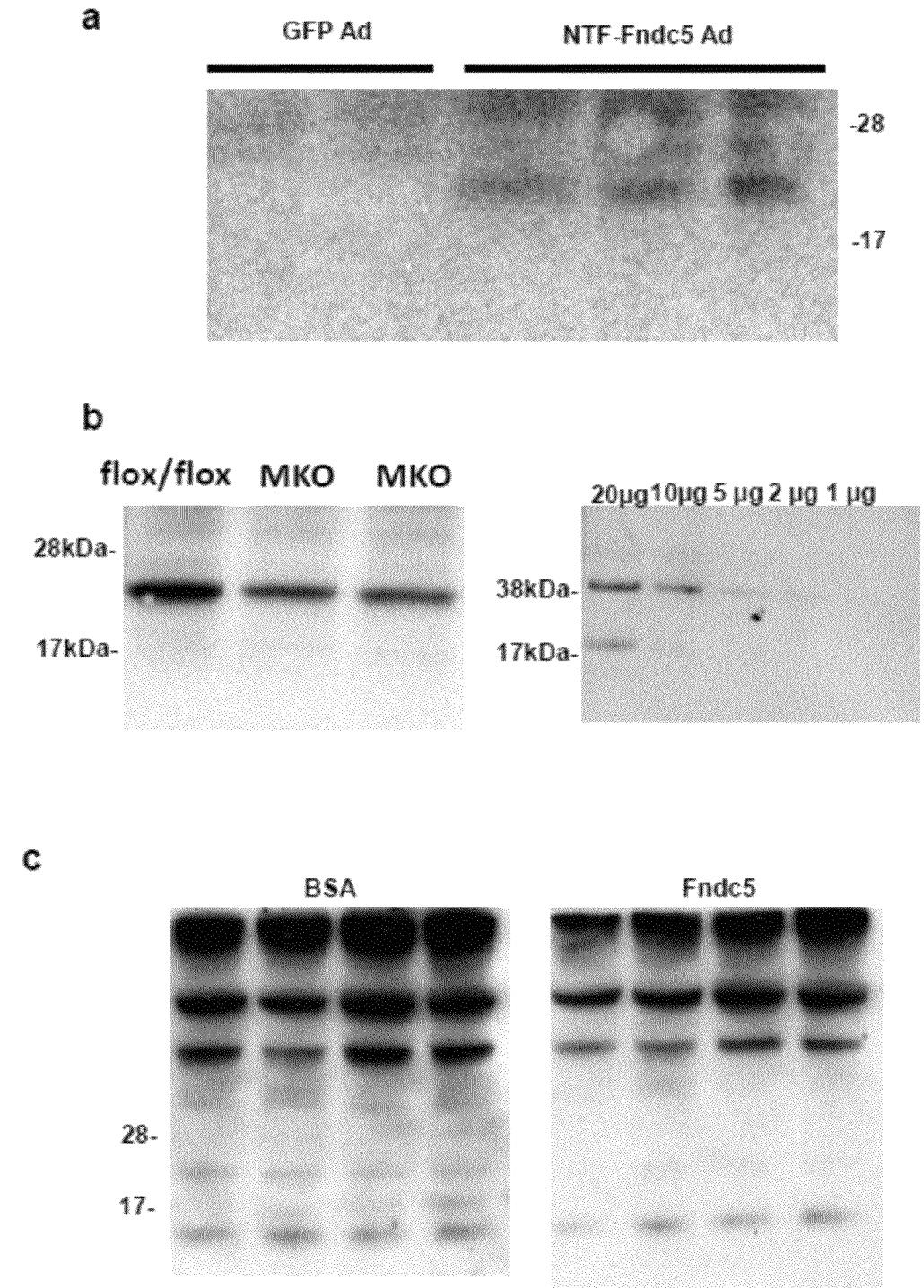
FIGS. 10A-10C show the results of Western blot analyses.

Next, Irisin levels within plasma of wild-type mice were analyzed. This was done using Western blots after albumin/IgG pre-clearing and deglycosylation. As a positive control, the N-terminally flag-tagged Fndc5 expressed in mice via adenoviral injections was used. In addition, plasma of PGC1α muscle-specific knockout mice was used as a negative control. Both approaches identified Irisin with an apparent molecular mass of approximately 20 kDa (FIG. 10). This observation was definitively confirmed as an Fndc5-derived polypeptide via an antigen neutralization of antibody (FIG. 10). Mice had significantly elevated plasma concentrations of Irisin after they were subjected to three weeks of free wheel running (FIG. 8F). Semi-quantitative measurements indicated plasma levels of approximately 40 nM before exercise and 80 nM after this protocol (FIG. 10). Similar analyses conducted using human plasma obtained from subjects subjected to supervised exercise for 8 weeks, revealed a 2-fold increase in Fndc5 plasma levels with exercise (FIG. 8G). Thus, Irisin circulates in blood from mice and humans, and is increased with exercise.

Example 8

Irisin Improves Diet-Induced Obesity and Insulin Resistance In Vivo

Figure 11:
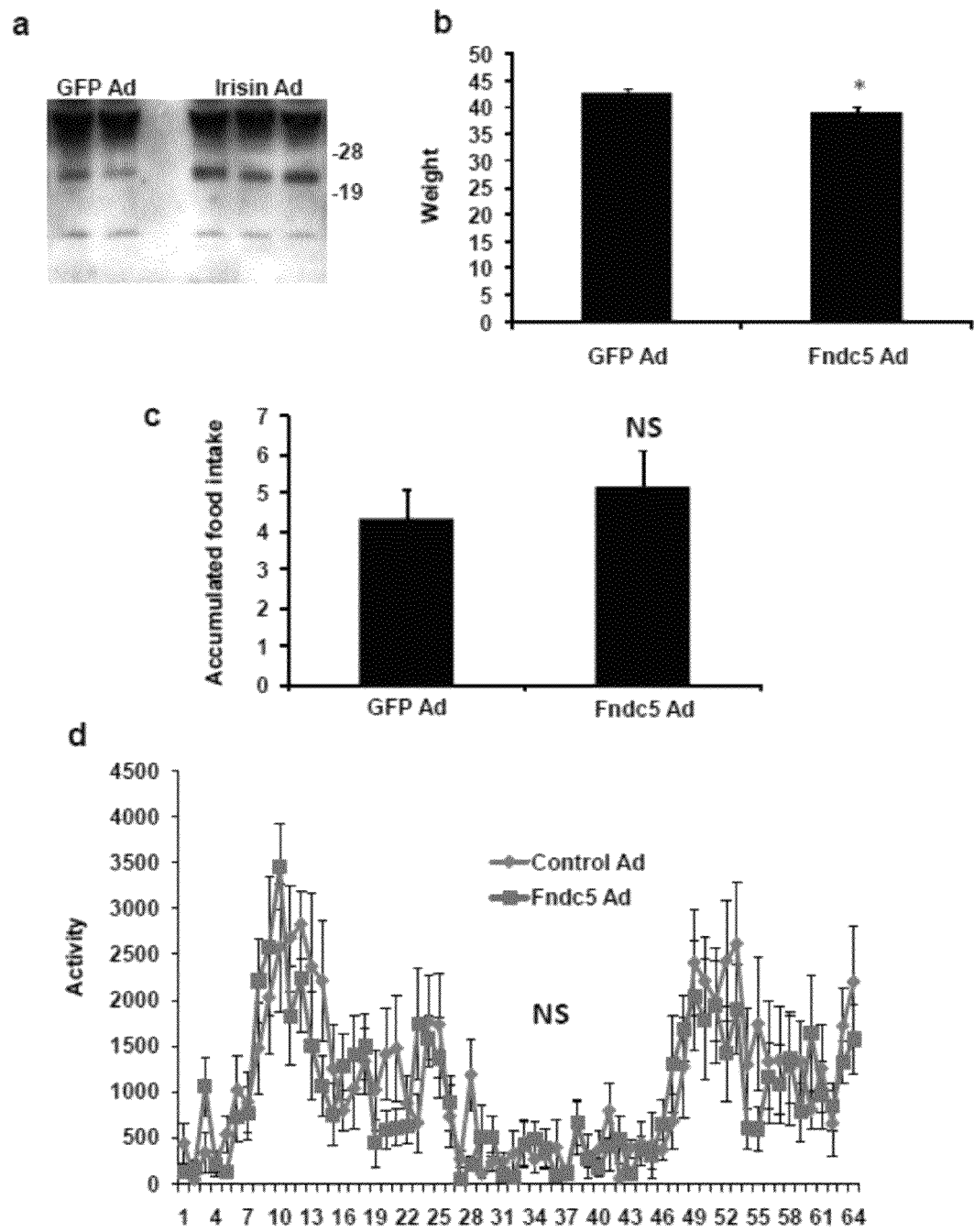
FIGS. 11A-11D show the results of analyzing mice exogenously expressing Fndc5.
Figure 12:
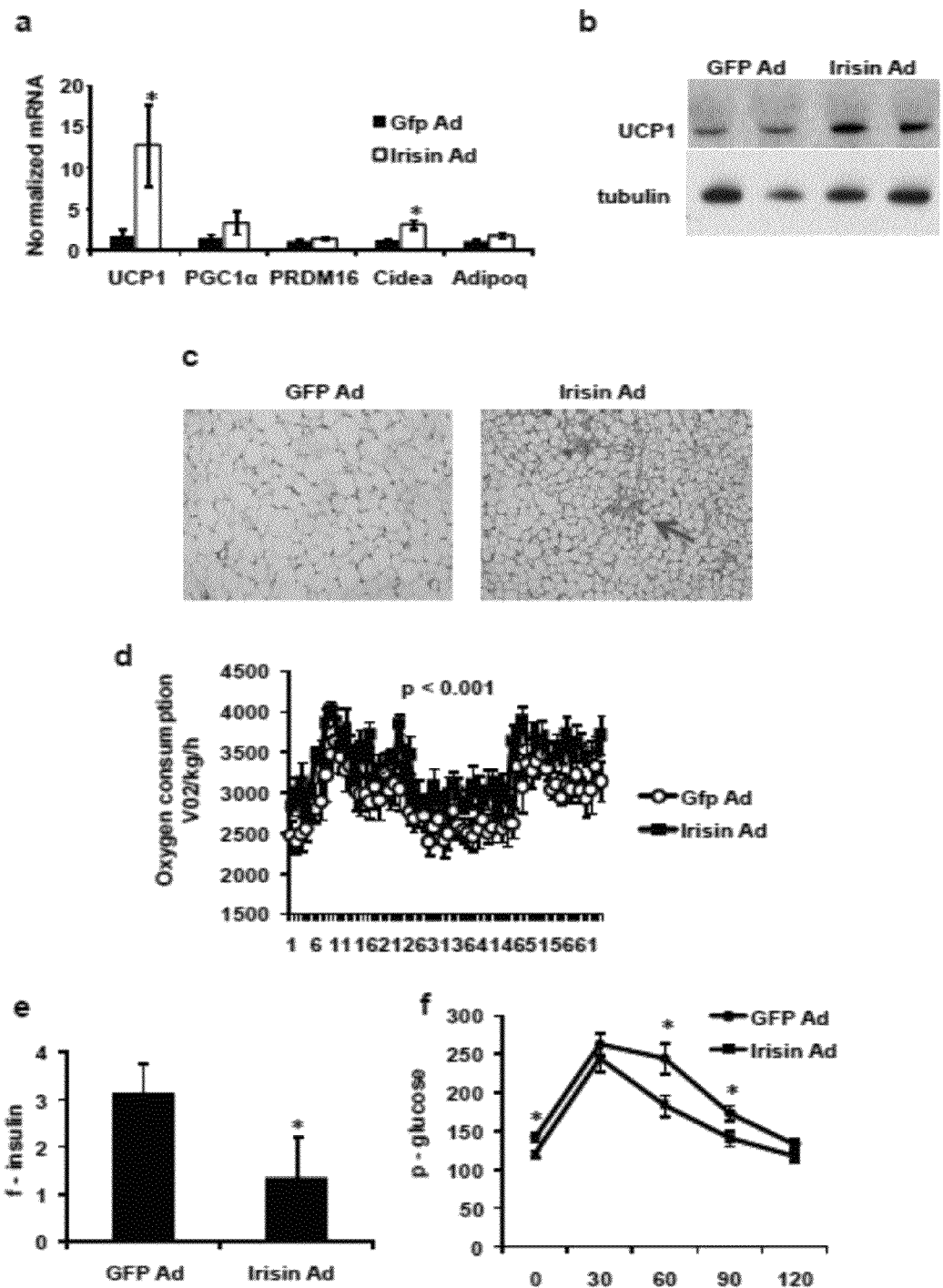
FIGS. 12A-12F show that Irisin induces the browning in vivo and protects against diet induced obesity and diabetes.
Figure 13:
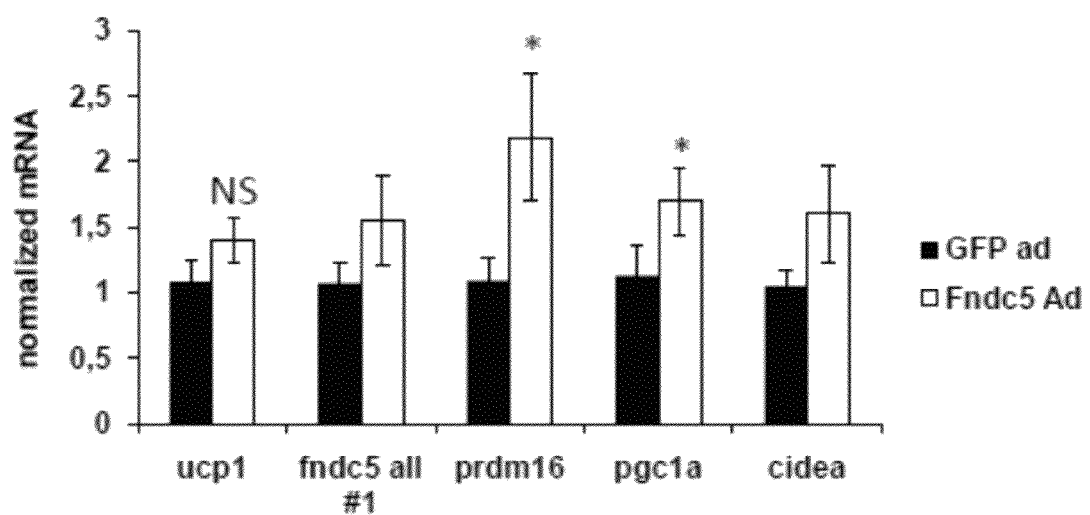
FIG. 13 shows the results of qPCR analyses of the indicated genes in epidydimal (visceral) or intrascapular brown fat (BAT) depots of high-fat diet treated mice 10 days after injection with Fndc5- or GFP-expressing adenovirus. * $p<0.05$ compared to control using students T-TEST.

Adenoviral vectors injected into the blood of mice are taken up and predominantly expressed from the liver. This method was used to express full-length Fndc5 (or Green Fluorescent Protein as a control) and Irisin levels in blood were subsequently measured. Adenoviral expression resulted in a 15-fold increase in liver Fndc5 mRNA, despite the fact that the liver expresses very low endogenous levels of this mRNA. Plasma levels were increased 3-4 fold (FIG. 11). The mice did not display any adverse reaction, and upon pathological examination, no apparent toxicity in any major organ system was observed. Ten days after injection, UCP1 was increased by 13-fold in the subcutaneous depot relative to injections with the control virus expressing GFP (FIGS. 12A-12B). Cidea expression levels were also significantly up-regulated (FIG. 12A). There were no changes in expression of UCP1 in the interscapular BAT, but a minor elevation in Cidea and PGC1α mRNA was observed (FIG. 13). The changes in gene expression in the subcutaneous adipose tissues were accompanied by a clear increase in the number of UCP1-positive, multilocular adipocytes. (FIG. 12C). Thus, moderate increases in circulating Irisin can induce browning of white adipose tissues in vivo, including increased expression of UCP1.

Since activation of the classical brown fat or browning of white fat has been shown to improve obesity and glucose homeostasis in vivo (Seale et al. (2011) J. Clin. Invest. 121, 96-105), Irisin-expressing adenoviruses were delivered to mice rendered obese and insulin-resistance by feeding a high fat diet. The Irisin-expressing virus increased UCP1 expression to the same degree as in lean mice. Notably, these changes occurred with only moderately increased Irisin blood levels (3-fold compared to GFP-expressing mice). This effect was accompanied with a very large increase in oxygen consumption and thermogenesis (FIG. 12D), consistent with the browning of the fat. Importantly, there were no changes in food intake or physical activity (FIG. 11), but body weights of the Irisin expressing mice were reduced significantly after 10 days compared to GFP-expressing controls (FIG. 11).

The Irisin-expressing mice had improved glucose tolerance when subjected to glucose tolerance tests, and fasting insulin was reduced (FIGS. 12E-12F). Thus, even moderately increased levels of circulating Irisin potently increases energy expenditure, reduces body weight and improves diet-induced insulin resistance.

Exercise has the capacity to improve metabolic status in obesity and type II diabetes via poorly understood mechanisms. Importantly, exercise increases whole body energy expenditure beyond the calories used in the actual work performed during exercise (Speakman and Selman (2003) Proc. Nutr. Soc. 62, 621-634). Since transgenic mice expressing PGC1α selectively in muscle showed a remarkable resistance to age-related obesity and diabetes (Wenz et al. (2009) Proc. Natl. Acad. Sci. USA 106, 20405-20410), factors secreted from muscle under control of this coactivator that might increase whole body energy expenditure were sought to be identified. These analyses resulted in the discovery of a new polypeptide hormone, Irisin, which is regulated by PGC1α, secreted from muscle into blood, and activates thermogenic function in adipose tissues.

Irisin is remarkable in several respects. First, it has very powerful effects on the browning of certain white adipose tissues, both in culture and in vivo. Nanomolar levels of this protein increases UCP1 in cultures of primary white fat cells by 50-fold or more, resulting in large increases in respiration. Perhaps more remarkable, viral delivery of Irisin that causes only a moderate increase (~3-fold) in circulating levels stimulates a 10-20 fold increase in UCP1, increased energy expenditure and an improvement in glucose tolerance of high fat fed mice. Since this is within the range of increases seen with exercise in mouse and man, Irisin mediates at least some of the beneficial effects of exercise on the browning of adipose tissues and increases in energy expenditure.

Second, the cleaved and secretion of portion of Fndc5, the hormone Irisin, is extremely highly conserved in all mammalian species. Mouse and human Irisin are 100% identical, compared to 85% identity seen for insulin, 90% for glucagon and 83% identity seen for leptin. This certainly implies a highly conserved function that is likely to be mediated by a cell surface receptor.

Finally, Irisin action is very selective for the browning of white adipose tissues. It is now appreciated that there are two different types of adipose tissues that are considered brown: the classical brown fat (such as the interscapular depot) that expresses UCP1 and is thermogenic even under ambient conditions. This fat is derived from a myf5, muscle-like cell lineage (Seale, 2008). In addition, certain white fat depots, especially subcutaneous fat, can turn on UCP1 and other thermogenic genes under prolonged cold or adrenergic stimuli. These cells, which are not derived from a myf-5 lineage, have been called beige cells or brite cells. It has been demonstrated herein that Irisin specifically activates thermogenic function in beige cells. It is important to note that unbiased global gene expression analysis indicated that activation of UCP1 expression and other thermogenic genes is the most prominent change caused by Irisin in these cells.

Fndc5/Frcp2/PeP was previously described as a peroxisomal protein, displaying increased expression with myocyte differentiation. Another report, however, suggested that Fndc5 was localized to the endoplasmic reticulum. Beyond these two studies, no further reports regarding the protein have been made and no protein function had been described. Based on the gene structure, with a signal peptide that was evidently missed in the studies of Ferrer-Martinez, et al. (2002), it was determined herein that Fndc5 is a secreted protein. Indeed, it was observed that the signal peptide is removed and the mature protein is further proteolytically cleaved and glycosylated, to release the 112 aa long polypeptide, Irisin. The cleavage and secretion of Irisin is similar to the release/shedding of other transmembrane polypeptide hormones and hormone-like molecules such as the epidermal growth factor (EGF).

Since the conservation of calories would provide an overall survival advantage for mammals, it appears somewhat paradoxical that exercise would stimulate the secretion of a polypeptide hormone that increases thermogenesis and energy expenditure. Two ideas might explain this. First, the increase observed in Irisin expression with exercise in mouse and man may have evolved as a response to muscle contraction during shivering. Shivering, which is involuntary muscle contraction, occurs in mammals as an acute thermogenic response to cold temperatures. Muscle secretion of a hormone that activates adipose thermogenesis during this process might provide a broader, more robust defense against hypothermia. Secondly, exercise invariably results in release of metabolites such as lactate into the blood and it is possible that the accumulation of such metabolites could alter the function of other tissues. Thermogenesis based on mitochondrial uncoupling can serve as a highly effective "sink" (Bartelt, 2011), whereby such metabolites are reduced to carbon dioxide, water and heat.

Exogenously administered Irisin induces formation/activation of brown fat and thermogenesis and may be prepared and delivered as an injectable polypeptide. Increased brown fat formation and activation has been clearly shown to have anti-obesity, anti-diabetic effects in multiple murine models (Seale, 2011), and adult humans have significant deposits of brown fat (Enerback, 2010). Indeed, even the relatively short treatments of obese mice with Irisin described herein improved glucose homeostasis and caused weight loss.

Another important aspect of the present invention relates to other beneficial effects of exercise, especially for diseases for which no effective treatment exists. Heart failure and neurodegenerative diseases, such as Parkinson's disease and Alzheimer's disease, are devastating disorders for which exercise has shown promise. However, it is very difficult or impossible for many of these patients to undertake vigorous exercise. Treating such patients with the compositions and methods of the present invention may therefore provide novel approaches for treating these types of diseases and disorders.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide which:
comprises amino acid residues 30-140 of SEQ ID NO:2, wherein said polypeptides does not include an Fndc5 signal peptide and amino acid residues 141-209 of SEQ ID NO: 2 or fragments thereof.

2. The isolated polypeptide of claim 1, which comprises amino acid residues 29-140 of SEQ ID NO:2.

3. The isolated polypeptide of claim 1, having a molecular weight of about 20 kilodaltons.

4. The isolated polypeptide of claim 3, wherein the molecular weight is as determined by gel electrophoresis under deglycosylated, reduced, and denatured conditions.

5. The isolated polypeptide of claim 1, wherein the polypeptide has the ability to promote one or more biological activities selected from the group consisting of:
a) expression of a marker selected from the group consisting of: cidea, adiponectin, adipsin, otopetrin, type II deiodinase, cig30, ppar gamma 2, pgc 1 o, ucp1, elovl3, cAMP, Prdm16, cytochrome C, cox4i1, coxIII, cox5b, cox7a1, cox8b, glut4, atpase b2, cox II, atpSo, ndufb5, ap2, ndufs1, GRPI09A, acylCoA-thioesterase 4, EARA1, claudin1, PEPCK, fgf21, acylCoA-thioesterase 3, and dio'Z;
b) thermogenesis in adipose cells;
c) differentiation of adipose cells;
d) insulin sensitivity of adipose cells;
e) basal respiration or uncoupled respiration;
f) hepatosteatosis reduction;
g) appetite reduction;
h) insulin secretion of pancreatic beta cells;
i) cardiac function reduction;
j) cardiac hypertrophy; and
k) muscle hypoplasia reduction.

6. The isolated polypeptide of claim 1, wherein said polypeptide has the ability to promote the expression of fgf21.

7. The isolated polypeptide of claim 1, wherein said polypeptide has the ability to promote the expression of ucp1.

8. The isolated polypeptide of claim 1, wherein said polypeptide has the ability to promote the expression of fgf21 and ucp1.

9. The isolated polypeptide of claim 1, wherein the polypeptide has the ability to induce brown fat differentiation.

10. The isolated polypeptide of claim 1, wherein the polypeptide is less than 195 amino acids in length.

11. The isolated polypeptide of claim 1, wherein the polypeptide is between 110 and 125 amino acids in length.

12. The isolated polypeptide of claim 1, wherein the polypeptide is more than 110 amino acids in length and less than 135 amino acids in length.

13. The isolated polypeptide of claim 1, wherein at least one amino acid residue is glycosylated.

14. The isolated polypeptide of claim 1, wherein at least one amino acid residue is pegylated.

15. The isolated polypeptide of claim 1, wherein the polypeptide is secreted by a mammalian cell.

16. The isolated polypeptide of claim 1, further comprising a heterologous polypeptide.

17. The isolated polypeptide of claim 16, wherein the heterologous polypeptide comprises a dimerization or oligomerization domain.

18. The isolated polypeptide of claim 16, wherein the heterologous polypeptide is an agent that promotes plasma solubility.

19. The isolated polypeptide of claim 16, wherein the heterologous polypeptide comprises an Fc domain.

20. The isolated polypeptide of claim 1, wherein the polypeptide is at least 75% pure.

* * * * *

SEQUENCE LISTING

<160> NUMBER OF SEQ ID NOS: 56

<210> SEQ ID NO 1
<211> LENGTH: 630
<212> TYPE: DNA
<213> ORGANISM: Mus sp.

<400> SEQUENCE: 1

```
atgcccccag gaccgtgcgc ctggccgccc cgcgccgcgc tccgcctgtg gctaggctgc      60
gtctgcttcg cgctggtgca ggcggacagc ccctcagccc ctgtgaacgt gaccgtccgg     120
cacctcaagg ccaactctgc cgtggtcagc tgggatgtcc tggaggatga agtggtcatt     180
ggctttgcca tctctcagca agagaaggat gtgcggatgc tccggttcat tcaggaggtg     240
aacaccacca cccggtcctg cgctctctgg gacctggagg aggacacaga atatatcgtc     300
catgtgcagg ccatctccat ccagggacag agcccagcca gtgagcctgt gctcttcaag     360
accccacgcg aggctgaaaa gatggcctca aagaacaaag atgaggtgac catgaaggag     420
atggggagga accagcagct gcgaacgggg gaggtgctga tcattgttgt ggtcctcttc     480
atgtgggcag gtgttatagc tctcttctgc cgccagtatg atatcatcaa ggacaacgag     540
cccaataaca acaaggagaa aaccaagagc gcatcagaaa ccagcacacc ggagcatcag     600
ggtgggggtc tcctccgcag caagatatga                                     630
```

<210> SEQ ID NO 2
<211> LENGTH: 209
<212> TYPE: PRT
<213> ORGANISM: Mus sp.

<400> SEQUENCE: 2

```
Met Pro Pro Gly Pro Cys Ala Trp Pro Pro Arg Ala Ala Leu Arg Leu
1               5                   10                  15

Trp Leu Gly Cys Val Cys Phe Ala Leu Val Gln Ala Asp Ser Pro Ser
            20                  25                  30

Ala Pro Val Asn Val Thr Val Arg His Leu Lys Ala Asn Ser Ala Val
        35                  40                  45

Val Ser Trp Asp Val Leu Glu Asp Glu Val Val Ile Gly Phe Ala Ile
    50                  55                  60

Ser Gln Gln Lys Lys Asp Val Arg Met Leu Arg Phe Ile Gln Glu Val
65                  70                  75                  80

Asn Thr Thr Thr Arg Ser Cys Ala Leu Trp Asp Leu Glu Glu Asp Thr
                85                  90                  95

Glu Tyr Ile Val His Val Gln Ala Ile Ser Ile Gln Gly Gln Ser Pro
            100                 105                 110

Ala Ser Glu Pro Val Leu Phe Lys Thr Pro Arg Glu Ala Glu Lys Met
        115                 120                 125

Ala Ser Lys Asn Lys Asp Glu Val Thr Met Lys Glu Met Gly Arg Asn
    130                 135                 140

Gln Gln Leu Arg Thr Gly Glu Val Leu Ile Ile Val Val Val Leu Phe
145                 150                 155                 160

Met Trp Ala Gly Val Ile Ala Leu Phe Cys Arg Gln Tyr Asp Ile Ile
                165                 170                 175

Lys Asp Asn Glu Pro Asn Asn Asn Lys Glu Lys Thr Lys Ser Ala Ser
            180                 185                 190

Glu Thr Ser Thr Pro Glu His Gln Gly Gly Gly Leu Leu Arg Ser Lys
        195                 200                 205

Ile
```

<210> SEQ ID NO 3
<211> LENGTH: 462
<212> TYPE: DNA
<213> ORGANISM: Homo sapiens

<400> SEQUENCE: 3

```
atgctgcgct tcatccagga ggtgaacacc accaccogct catgtgccct ctgggacctg    60
gaggaggata cggagtacat agtccacgtg caggccatct ccattcaggg ccagagccca   120
gccagcgagc ctgtgctctt caagacccog cgtgaggctg agaagatggc ctccaagaac   180
aaagatgagg taaccatgaa agagatgggg aggaaccaac agctgcggac aggcgaggtg   240
ctgatcatcg tcgtggtcct gttcatgtgg gcaggtgtca ttgccctctt ctgccgccag   300
tatgacatca tcaaggacaa tgaacccaat aacaacaagg aaaaaaccaa gagtgcatca   360
gaaaccagca caccagagca ccagggcggg gggcttctcc gcagcaaggt gagggcaaga   420
cctgggcctg gtgggccac cctgtgcctc atgctctggt aa                      462
```

<210> SEQ ID NO 4
<211> LENGTH: 153
<212> TYPE: PRT
<213> ORGANISM: Homo sapiens

<400> SEQUENCE: 4

```
Met Leu Arg Phe Ile Gln Glu Val Asn Thr Thr Arg Ser Cys Ala
1               5                  10                  15

Leu Trp Asp Leu Glu Glu Asp Thr Glu Tyr Ile Val His Val Gln Ala
            20                  25                  30

Ile Ser Ile Gln Gly Gln Ser Pro Ala Ser Glu Pro Val Leu Phe Lys
        35                  40                  45

Thr Pro Arg Glu Ala Glu Lys Met Ala Ser Lys Asn Lys Asp Glu Val
    50                  55                  60

Thr Met Lys Glu Met Gly Arg Asn Gln Gln Leu Arg Thr Gly Glu Val
65                  70                  75                  80

Leu Ile Ile Val Val Val Leu Phe Met Trp Ala Gly Val Ile Ala Leu
                85                  90                  95

Phe Cys Arg Gln Tyr Asp Ile Ile Lys Asp Asn Glu Pro Asn Asn Asn
            100                 105                 110

Lys Glu Lys Thr Lys Ser Ala Ser Glu Thr Ser Thr Pro Glu His Gln
        115                 120                 125

Gly Gly Gly Leu Leu Arg Ser Lys Val Arg Ala Arg Pro Gly Pro Gly
    130                 135                 140

Trp Ala Thr Leu Cys Leu Met Leu Trp
145                 150
```

<210> SEQ ID NO 5
<211> LENGTH: 414
<212> TYPE: DNA
<213> ORGANISM: Homo sapiens

<400> SEQUENCE: 5

```
atgctgcgct tcatccagga ggtgaacacc accaccogct catgtgccct ctgggacctg    60
gaggaggata cggagtacat agtccacgtg caggccatct ccattcaggg ccagagccca   120
gccagcgagc ctgtgctctt caagacccog cgtgaggctg agaagatggc ctccaagaac   180
aaagatgagg taaccatgaa agagatgggg aggaaccaac agctgcggac aggcgaggtg   240
ctgatcatcg tcgtggtcct gttcatgtgg gcaggtgtca ttgccctctt ctgccgccag   300
tatgacatca tcaaggacaa tgaacccaat aacaacaagg aaaaaaccaa gagtgcatca   360
gaaaccagca caccagagca ccagggcggg gggcttctcc gcagcaagat atga         414
```

<210> SEQ ID NO 6

<211> LENGTH: 137
<212> TYPE: PRT
<213> ORGANISM: Homo sapiens

<400> SEQUENCE: 6

Met Leu Arg Phe Ile Gln Glu Val Asn Thr Thr Thr Arg Ser Cys Ala
1               5                   10                  15
Leu Trp Asp Leu Glu Glu Asp Thr Glu Tyr Ile Val His Val Gln Ala
            20                  25                  30
Ile Ser Ile Gln Gly Gln Ser Pro Ala Ser Glu Pro Val Leu Phe Lys
        35                  40                  45
Thr Pro Arg Glu Ala Glu Lys Met Ala Ser Lys Asn Lys Asp Glu Val
50                  55                  60
Thr Met Lys Glu Met Gly Arg Asn Gln Gln Leu Arg Thr Gly Glu Val
65                  70                  75                  80
Leu Ile Ile Val Val Val Leu Phe Met Trp Ala Gly Val Ile Ala Leu
                85                  90                  95
Phe Cys Arg Gln Tyr Asp Ile Ile Lys Asp Asn Glu Pro Asn Asn Asn
            100                 105                 110
Lys Glu Lys Thr Lys Ser Ala Ser Glu Thr Ser Thr Pro Glu His Gln
        115                 120                 125
Gly Gly Gly Leu Leu Arg Ser Lys Ile
    130                 135

<210> SEQ ID NO 7
<211> LENGTH: 321
<212> TYPE: DNA
<213> ORGANISM: Homo sapiens

<400> SEQUENCE: 7
atgctgcgct tcatccagga ggtgaacacc accacccgct catgtgccct ctgggacctg      60
gaggaggata cggagtacat agtccacgtg caggccatct ccattcaggg ccagagccca     120
gccagcgagc ctgtgctctt caagacccccg cgtgaggctg agaagatggc ctccaagaac    180
aaagatgagg taaccatgaa agagatgggg aggaaccaac agctgcggac aggcgaggtg     240
ctgatcatcg tcgtggtcct gttcatgtgg gcaggtgtca ttgccctctt ctgccgccag     300
tatgacatca ttgaagcgtg a                                               321

<210> SEQ ID NO 8
<211> LENGTH: 106
<212> TYPE: PRT
<213> ORGANISM: Homo sapiens

<400> SEQUENCE: 8

Met Leu Arg Phe Ile Gln Glu Val Asn Thr Thr Thr Arg Ser Cys Ala
1               5                   10                  15
Leu Trp Asp Leu Glu Glu Asp Thr Glu Tyr Ile Val His Val Gln Ala
            20                  25                  30
Ile Ser Ile Gln Gly Gln Ser Pro Ala Ser Glu Pro Val Leu Phe Lys
        35                  40                  45
Thr Pro Arg Glu Ala Glu Lys Met Ala Ser Lys Asn Lys Asp Glu Val
50                  55                  60
Thr Met Lys Glu Met Gly Arg Asn Gln Gln Leu Arg Thr Gly Glu Val
65                  70                  75                  80
Leu Ile Ile Val Val Val Leu Phe Met Trp Ala Gly Val Ile Ala Leu
                85                  90                  95

Phe Cys Arg Gln Tyr Asp Ile Ile Glu Ala
            100                 105

<210> SEQ ID NO 9
<211> LENGTH: 1203
<212> TYPE: DNA
<213> ORGANISM: Gallus gallus

<400> SEQUENCE: 9

| | | | | | |
|---|---|---|---|---|---|
| atggagaaga | acagggacgg | ccgcggcccc | cctggtgtcc | atctggggat | ggagaaggaa | 60 |
| gatgatttag | agcccggtga | cacgccgggg | ctgcgcgaag | ccctggtggc | gagatgtcac | 120 |
| cgctgccgcg | cacccgccgg | gggtctcacc | gggacgggcc | ccgtttgctc | cttccggcga | 180 |
| tggggagcgg | tccgggccga | gggctcccgg | tcccgcctgg | gggaaactga | ggcagacggc | 240 |
| ggggccgggc | ggggcggggg | ccgagccgcc | cccgggccgg | gggagggacc | ggagcggggc | 300 |
| tgcccagcgc | tgcagcgggc | ggagccgggg | ctcggcgggg | ccgcctcccg | gccgagccga | 360 |
| gccgaaccga | gccgcgctgc | cgagggccgc | cgagcccgca | gccgcccccg | gccgaaccgg | 420 |
| gcggccccgc | cggttccggg | ccccggagct | ctccgcggtg | ctgaacggcg | ccgccgcgcc | 480 |
| cgcgggacgc | cggccccgga | gcggctcggc | cccggcgcgg | cgcggcgggc | cgcgggggga | 540 |
| tggagccctt | cctgggctgc | accggcgccg | cgctcctgct | ctgctttcag | ctacgccggt | 600 |
| ctgcggccgg | tggaggcaga | cagcccttcg | gctccggtca | atgtcacagt | caaacacctg | 660 |
| aaggccaact | cagctgtagt | gacttgggac | gttctggagg | atgaagttgt | cattggattt | 720 |
| gccatttccc | agcagaagaa | ggacgtgcgg | atgctgcgct | tcatccagga | ggtgaacacc | 780 |
| accacccgct | cctgtgccct | ctgggaccta | gaggaggaca | ctgagtacat | tgtgcatgtc | 840 |
| caggccatca | gcatccaagg | ccagagccct | gccagtgagc | cagtcctctt | caagaccccc | 900 |
| agggaagctg | agaaactggc | ttctaaaaat | aaagatgagg | tgacaatgaa | ggagatggcg | 960 |
| aagaaaaacc | aacagctgcg | cgcaggggaa | atactcatca | ttgtggtggt | gttgtttatg | 1020 |
| tgggcagggg | tgatcgccct | gttctgcagg | cagtacgaca | tcatcaaaga | caacgagccg | 1080 |
| aacaacagca | aggagaaagc | caagagcgcc | tcagagaaca | gcaccccga | gcaccagggt | 1140 |
| gggggggctgc | tccgcagcaa | gttcccaaaa | aacaaaccct | cagtgaacat | cattgaggca | 1200 |
| taa | | | | | | 1203 |

<210> SEQ ID NO 10
<211> LENGTH: 400
<212> TYPE: PRT
<213> ORGANISM: Gallus gallus

<400> SEQUENCE: 10

Met Glu Lys Asn Arg Asp Gly Arg Gly Pro Gly Val His Leu Gly
1               5                   10                  15

Met Glu Lys Glu Asp Asp Leu Glu Pro Gly Asp Thr Pro Gly Leu Arg
            20                  25                  30

Glu Ala Leu Val Ala Arg Cys His Arg Cys Arg Ala Pro Ala Gly Gly
        35                  40                  45

Leu Thr Gly Thr Gly Pro Val Cys Ser Phe Arg Arg Trp Gly Ala Val
    50                  55                  60

Arg Ala Glu Gly Ser Arg Ser Arg Leu Gly Glu Thr Glu Ala Asp Gly
65                  70                  75                  80

Gly Ala Gly Arg Gly Gly Arg Ala Ala Pro Gly Pro Gly Glu Gly
                85                  90                  95

```
Pro Glu Arg Gly Cys Pro Ala Leu Gln Arg Ala Glu Pro Gly Leu Gly
            100                 105                 110

Gly Ala Ala Ser Arg Pro Ser Arg Ala Glu Pro Ser Arg Ala Ala Glu
        115                 120                 125

Gly Arg Arg Ala Arg Ser Arg Pro Arg Pro Asn Arg Ala Ala Pro Pro
    130                 135                 140

Val Pro Gly Pro Gly Ala Leu Arg Gly Ala Glu Arg Arg Arg Arg Ala
145                 150                 155                 160

Arg Gly Thr Pro Ala Pro Glu Arg Leu Gly Pro Gly Ala Ala Arg Arg
                165                 170                 175

Ala Ala Gly Gly Trp Ser Pro Ser Trp Ala Pro Ala Pro Arg Ser
            180                 185                 190

Cys Ser Ala Phe Ser Tyr Ala Gly Leu Arg Pro Val Glu Ala Asp Ser
        195                 200                 205

Pro Ser Ala Pro Val Asn Val Thr Val Lys His Leu Lys Ala Asn Ser
    210                 215                 220

Ala Val Val Thr Trp Asp Val Leu Glu Asp Glu Val Val Ile Gly Phe
225                 230                 235                 240

Ala Ile Ser Gln Gln Lys Lys Asp Val Arg Met Leu Arg Phe Ile Gln
                245                 250                 255

Glu Val Asn Thr Thr Arg Ser Cys Ala Leu Trp Asp Leu Glu Glu
            260                 265                 270

Asp Thr Glu Tyr Ile Val His Val Gln Ala Ile Ser Ile Gln Gly Gln
        275                 280                 285

Ser Pro Ala Ser Glu Pro Val Leu Phe Lys Thr Pro Arg Glu Ala Glu
    290                 295                 300

Lys Leu Ala Ser Lys Asn Lys Asp Glu Val Thr Met Lys Glu Met Ala
305                 310                 315                 320

Lys Lys Asn Gln Gln Leu Arg Ala Gly Glu Ile Leu Ile Val Val
                325                 330                 335

Val Leu Phe Met Trp Ala Gly Val Ile Ala Leu Phe Cys Arg Gln Tyr
            340                 345                 350

Asp Ile Ile Lys Asp Asn Glu Pro Asn Asn Ser Lys Glu Lys Ala Lys
        355                 360                 365

Ser Ala Ser Glu Asn Ser Thr Pro Glu His Gln Gly Gly Leu Leu
    370                 375                 380

Arg Ser Lys Phe Pro Lys Asn Lys Pro Ser Val Asn Ile Ile Glu Ala
385                 390                 395                 400

<210> SEQ ID NO 11
<211> LENGTH: 555
<212> TYPE: DNA
<213> ORGANISM: Danio rerio

<400> SEQUENCE: 11
atgagttctt acagtttggc agctccagtg aatgtgtcca tcagggatct gaagagcagc      60
tcagccgtgg tgacatggga cacgccagac ggagagccag tcatcggctt cgccatcaca     120
caacagaaga aagatgtccg catgctgcgc tttattcaag aagtgaacac caccacgcgg     180
agctgtgcat tgtgggatct ggaagctgat acgattaca ttgtgcacgt tcagtctatc      240
agcatcagcg gggcgagtcc tgttagtgaa gctgtgcact caagacccc gacagaagtt      300 gaaacacagg cctccaagaa caagacgag gtgacgatgg aggaggtcgg gccgaacgct      360
cagctcaggg ccggagagtt catcattatt gtggtggtcc tcatcatgtg ggcaggtgtg      420
```

```
atcgcactat tctgccgtca gtatgacatc attaaagaca acgaaccaaa caataacaag    480
gataaagcca agaactcgtc tgaatgcagc actccagagc acacgtcagg tggcctgctg    540
cgcagtaagg tataa                                                    555
```

<210> SEQ ID NO 12
<211> LENGTH: 184
<212> TYPE: PRT
<213> ORGANISM: Danio rerio

<400> SEQUENCE: 12

Met Ser Ser Tyr Ser Leu Ala Ala Pro Val Asn Val Ser Ile Arg Asp
1               5                   10                  15

Leu Lys Ser Ser Ala Val Val Thr Trp Asp Thr Pro Asp Gly Glu
            20                  25                  30

Pro Val Ile Gly Phe Ala Ile Thr Gln Gln Lys Lys Asp Val Arg Met
        35                  40                  45

Leu Arg Phe Ile Gln Glu Val Asn Thr Thr Thr Arg Ser Cys Ala Leu
    50                  55                  60

Trp Asp Leu Glu Ala Asp Thr Asp Tyr Ile Val His Val Gln Ser Ile
65                  70                  75                  80

Ser Ile Ser Gly Ala Ser Pro Val Ser Glu Ala Val His Phe Lys Thr
                85                  90                  95

Pro Thr Glu Val Glu Thr Gln Ala Ser Lys Asn Lys Asp Glu Val Thr
            100                 105                 110

Met Glu Glu Val Gly Pro Asn Ala Gln Leu Arg Ala Gly Glu Phe Ile
        115                 120                 125

Ile Ile Val Val Val Leu Ile Met Trp Ala Gly Val Ile Ala Leu Phe
    130                 135                 140

Cys Arg Gln Tyr Asp Ile Ile Lys Asp Asn Pro Asn Asn Asn Lys
145                 150                 155                 160

Asp Lys Ala Lys Asn Ser Ser Glu Cys Ser Thr Pro Glu His Thr Ser
                165                 170                 175

Gly Gly Leu Leu Arg Ser Lys Val
            180

<210> SEQ ID NO 13
<211> LENGTH: 336
<212> TYPE: DNA
<213> ORGANISM: Mus sp.

<400> SEQUENCE: 13

```
gacagcccct cagcccctgt gaacgtgacc gtccggcacc tcaaggccaa ctctgccgtg    60
gtcagctggg atgtcctgga ggatgaagtg gtcattggct tgccatctc tcagcagaag    120 aaggatgtgc ggatgctccg gttcattcag gaggtgaaca ccaccacccg gtcctgcgct    180
ctctgggacc tggaggagga cacagaatat atcgtccatg tgcaggccat ctccatccag    240
ggacagagcc cagccagtga gcctgtgctc ttcaagaccc cacgcgaggc tgaaaagatg    300
gcctcaaaga acaaagatga ggtgaccatg aaggag                              336
```

<210> SEQ ID NO 14
<211> LENGTH: 181
<212> TYPE: PRT
<213> ORGANISM: Mus sp.

<400> SEQUENCE: 14

Asp Ser Pro Ser Ala Pro Val Asn Val Thr Val Arg His Leu Lys Ala

```
                1               5                   10                  15
            Asn Ser Ala Val Val Ser Trp Asp Val Leu Glu Asp Glu Val Ile
                        20                  25                  30
            Gly Phe Ala Ile Ser Gln Gln Lys Lys Asp Val Arg Met Leu Arg Phe
                        35                  40                  45
            Ile Gln Glu Val Asn Thr Thr Thr Arg Ser Cys Ala Leu Trp Asp Leu
                50                  55                  60
            Glu Glu Asp Thr Glu Tyr Ile Val His Val Gln Ala Ile Ser Ile Gln
            65                  70                  75                  80
            Gly Gln Ser Pro Ala Ser Glu Pro Val Leu Phe Lys Thr Pro Arg Glu
                        85                  90                  95
            Ala Glu Lys Met Ala Ser Lys Asn Lys Asp Glu Val Thr Met Lys Glu
                        100                 105                 110
            Met Gly Arg Asn Gln Gln Leu Arg Thr Gly Val Leu Ile Ile Val
                        115                 120                 125
            Val Val Leu Phe Met Trp Ala Gly Val Ile Ala Leu Phe Cys Arg Gln
            130                 135                 140
            Tyr Asp Ile Ile Lys Asp Asn Glu Pro Asn Asn Asn Lys Glu Lys Thr
            145                 150                 155                 160
            Lys Ser Ala Ser Glu Thr Ser Thr Pro Glu His Gln Gly Gly Gly Leu
                        165                 170                 175
            Leu Arg Ser Lys Ile
                        180
```

<210> SEQ ID NO 15
<211> LENGTH: 336
<212> TYPE: DNA
<213> ORGANISM: Homo sapiens

<400> SEQUENCE: 15

```
gacagtccct cagccccagt gaacgtcacc gtcaggcacc tcaaggccaa ctctgcagtg    60
gtgagctggg atgttctgga ggatgaggtt gtcatcggat ttgccatctc ccagcagaag   120
aaggatgtgc ggatgctgcg cttcatccag gaggtgaaca ccaccacccg ctcatgtgcc   180
ctctgggacc tggaggagga tacggagtac atagtccacg tgcaggccat ctccattcag   240
ggccagagcc cagccagcga gcctgtgctc ttcaagaccc cgcgtgaggc tgagaagatg   300
gcctccaaga caaagatga ggtaaccatg aaagag                              336
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

```
Gly Gly Gly Gly Ala Gly Gly Gly Gly
1               5
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tcaagaacga aagtcggagg                                        20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggactcttgg aaaacaccac tg                                     22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgaaggaga tggggaggaa                                        20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaccgagat tccttcaaa ctg                                     23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgctcttctg tatcgcccag t                                      21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccctgccatt gttaagacc                                         19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

-continued cagcacggtg aagccattc                                             19

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaagctgcgg tacaattcca g                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actgccacac ctccagtcat t                                          21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcactggcaa gttctactgc aa                                         22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tatctcccag agctgccatc ta                                         22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaggccaaga agagttctgg at                                         22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaccctgctg acactcaaaa ac                                         22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 30
cctcaaggaa tgcctgatac tg                                    22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 31
caggtcctca gtgatggaaa ag                                    22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 32
aagcacaagg actgactcaa gc                                    22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 33
ctagaacaca cgatgggctt tc                                    22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 34
tcagtgcagg gcttcctaaa                                       20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 35
ggacatctaa gggcatcac                                        19

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tccacacaga tgatctcacc ac                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcggcagaag agagctataa ca                                              22

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatctaggg ttatgatgct cttca                                           25

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gccgtgttaa ggaatctgct g                                               21

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgctgctgtt cctgttttc                                                  19

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcgtgcatcc gcttgtg                                                    17
```

```
<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccccttgtac ccttcaccaa t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctttgcctca ctcaggattg g                                              21

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtaggtgaag agaacggcct tgt                                            23

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agccagaaga tgctcacttg ac                                             22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgcccaggta agagcttcaa                                                20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaagagtca aatggcgtgt ag                                             22

<210> SEQ ID NO 48
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttggagaatt ccaccgacag                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtgatttggc agccacagtt                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
catgtccttg atggctggat                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcagctggaa ggaaggacaa                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tggggtgaac atcactttcc                                               20

<210> SEQ ID NO 53
<211> LENGTH: 8
<212> TYPE: PRT
<213> ORGANISM: Unknown
<220> FEATURE:
<223> OTHER INFORMATION: Description of Unknown: Fndc5
      C-terminal fragment peptide

<400> SEQUENCE: 53

Lys Asp Glu Val Thr Met Lys Glu
1               5

<210> SEQ ID NO 54
```

-continued

```
<211> LENGTH: 196
<212> TYPE: PRT
<213> ORGANISM: Homo sapiens

<400> SEQUENCE: 54

Met Arg Arg Trp Leu Gly Cys Val Cys Phe Ala Leu Val Gln Ala Asp
1               5                   10                  15

Ser Pro Ser Ala Pro Val Asn Val Thr Val Arg His Leu Lys Ala Asn
            20                  25                  30

Ser Ala Val Val Ser Trp Asp Val Leu Glu Asp Glu Val Ile Gly
        35                  40                  45

Phe Ala Ile Ser Gln Gln Lys Lys Asp Val Arg Met Leu Arg Phe Ile
50                  55                  60

Gln Glu Val Asn Thr Thr Thr Arg Ser Cys Ala Leu Trp Asp Leu Glu
65                  70                  75                  80

Glu Asp Thr Glu Tyr Ile Val His Val Gln Ala Ile Ser Ile Gln Gly
                85                  90                  95

Gln Ser Pro Ala Ser Glu Pro Val Leu Phe Lys Thr Pro Arg Glu Ala
            100                 105                 110

Glu Lys Met Ala Ser Lys Asn Lys Asp Glu Val Thr Met Lys Glu Met
        115                 120                 125

Gly Arg Asn Gln Gln Leu Arg Thr Gly Glu Val Leu Ile Ile Val Val
130                 135                 140

Val Leu Phe Met Trp Ala Gly Val Ile Ala Leu Phe Cys Arg Gln Tyr
145                 150                 155                 160

Asp Ile Ile Lys Asp Asn Glu Pro Asn Asn Asn Lys Glu Lys Thr Lys
                165                 170                 175

Ser Ala Ser Glu Thr Ser Thr Pro Glu His Gln Gly Gly Gly Leu Leu
            180                 185                 190

Arg Ser Lys Ile
        195

<210> SEQ ID NO 55
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Glu Trp Ser Trp Val Phe Leu Phe Phe Leu Ser Val Thr Thr Gly
1               5                   10                  15

Val His Ser Asp Ser Pro Ser Ala Pro Val Asn Val Thr Val Arg His
            20                  25                  30

Leu Lys Ala Asn Ser Ala Val Val Ser Trp Asp Val Leu Glu Asp Glu
        35                  40                  45

Val Val Ile Gly Phe Ala Ile Ser Gln Gln Lys Lys Asp Val Arg Met
50                  55                  60

Leu Arg Phe Ile Gln Glu Val Asn Thr Thr Thr Arg Ser Cys Ala Leu
65                  70                  75                  80

Trp Asp Leu Glu Glu Asp Thr Glu Tyr Ile Val His Val Gln Ala Ile
                85                  90                  95

Ser Ile Gln Gly Gln Ser Pro Ala Ser Glu Pro Val Leu Phe Lys Thr
            100                 105                 110

Pro Arg Glu Ala Glu Lys Met Ala Ser Lys Asn Lys Asp Glu Val Thr
        115                 120                 125
```

Met Lys Glu Met Gly Arg Asn Gln Gln Leu Arg Thr Gly Gly Gly
130                 135                 140

Ala Gly Gly Gly Asp Lys Thr His Thr Cys Pro Pro Cys Pro Ala
145                 150                 155                 160

Pro Glu Leu Leu Gly Gly Pro Ser Val Phe Leu Phe Pro Pro Lys Pro
            165                 170                 175

Lys Asp Thr Leu Met Ile Ser Arg Thr Pro Glu Val Thr Cys Val Val
                180                 185                 190

Val Asp Val Ser His Glu Asp Pro Glu Val Lys Phe Asn Trp Tyr Val
            195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Asp Glu Leu Thr
        275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375

<210> SEQ ID NO 56
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Glu Trp Ser Trp Val Phe Leu Phe Phe Leu Ser Val Thr Thr Gly
1               5                   10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp

|  |  |  | 100 |  |  | 105 |  |  |  | 110 |  |
|---|---|---|---|---|---|---|---|---|---|---|---|
| Leu | Asn | Gly<br>115 | Lys | Glu | Tyr | Lys<br>120 | Cys | Lys | Val | Ser<br>125 | Asn Lys Ala Leu Pro |

Ala Pro Ile Glu Lys Thr Ile Ser Lys Ala Lys Gly Gln Pro Arg Glu
130 135 140

Pro Gln Val Tyr Thr Leu Pro Pro Ser Arg Asp Glu Leu Thr Lys Asn
145 150 155 160

Gln Val Ser Leu Thr Cys Leu Val Lys Gly Phe Tyr Pro Ser Asp Ile
165 170 175

Ala Val Glu Trp Glu Ser Asn Gly Gln Pro Glu Asn Asn Tyr Lys Thr
180 185 190

Thr Pro Pro Val Leu Asp Ser Asp Gly Ser Phe Phe Leu Tyr Ser Lys
195 200 205

Leu Thr Val Asp Lys Ser Arg Trp Gln Gln Gly Asn Val Phe Ser Cys
210 215 220

Ser Val Met His Glu Ala Leu His Asn His Tyr Thr Gln Lys Ser Leu
225 230 235 240

Ser Leu Ser Pro Gly Lys Gly Gly Gly Ala Gly Gly Gly Gly Asp
245 250 255

Ser Pro Ser Ala Pro Val Asn Val Thr Val Arg His Leu Lys Ala Asn
260 265 270

Ser Ala Val Val Ser Trp Asp Val Leu Glu Asp Glu Val Val Ile Gly
275 280 285

Phe Ala Ile Ser Gln Gln Lys Lys Asp Val Arg Met Leu Arg Phe Ile
290 295 300

Gln Glu Val Asn Thr Thr Thr Arg Ser Cys Ala Leu Trp Asp Leu Glu
305 310 315 320

Glu Asp Thr Glu Tyr Ile Val His Val Gln Ala Ile Ser Ile Gln Gly
325 330 335

Gln Ser Pro Ala Ser Glu Pro Val Leu Phe Lys Thr Pro Arg Glu Ala
340 345 350

Glu Lys Met Ala Ser Lys Asn Lys Asp Glu Val Thr Met Lys Glu Met
355 360 365

Gly Arg Asn Gln Gln Leu Arg Thr Gly Glu Val Leu Ile Ile Val Val
370 375 380

Val Leu Phe Met Trp Ala Gly Val Ile Ala Leu Phe Cys Arg Gln Tyr
385 390 395 400

Asp Ile Ile Lys Asp Asn Glu Pro Asn Asn Asn Lys Glu Lys Thr Lys
405 410 415

Ser Ala Ser Glu Thr Ser Thr Pro Glu His Gln Gly Gly Gly Leu Leu
420 425 430

Arg Ser Lys Ile
435